(12) United States Patent
Plummer et al.

(10) Patent No.: US 11,746,111 B2
(45) Date of Patent: Sep. 5, 2023

(54) SIDEROPHORE CONJUGATED PYRAZOLIDINONES, AND ANALOGUES THEREOF

(71) Applicant: YALE UNIVERSITY, New Haven, CT (US)

(72) Inventors: Mark Plummer, Westbrook, CT (US); Denton Hoyer, West Haven, CT (US); Elizabeth Spencer, Southbury, CT (US)

(73) Assignee: YALE UNIVERSITY, New Haven, CT (US)

( * ) Notice: Subject to any disclaimer, the term of this patent is extended or adjusted under 35 U.S.C. 154(b) by 333 days.

(21) Appl. No.: 17/260,856

(22) PCT Filed: Jul. 19, 2019

(86) PCT No.: PCT/US2019/042643
§ 371 (c)(1),
(2) Date: Jan. 15, 2021

(87) PCT Pub. No.: WO2020/018929
PCT Pub. Date: Jan. 23, 2020

(65) Prior Publication Data
US 2021/0269449 A1    Sep. 2, 2021

Related U.S. Application Data

(60) Provisional application No. 62/701,249, filed on Jul. 20, 2018.

(51) Int. Cl.
*C07D 487/04* (2006.01)
*A61P 31/04* (2006.01)
(Continued)

(52) U.S. Cl.
CPC .......... *C07D 487/04* (2013.01); *A61K 9/0019* (2013.01); *A61K 31/427* (2013.01); *A61K 31/4439* (2013.01); *A61P 31/04* (2018.01)

(58) Field of Classification Search
CPC .............. A61K 31/427; A61K 31/4439; A61K 9/0019; A61P 31/04; C07D 487/04
See application file for complete search history.

(56) References Cited

U.S. PATENT DOCUMENTS

2004/0186087 A1* 9/2004 Grafe .................. A61K 41/0071
514/3.3

OTHER PUBLICATIONS

Ternansky et al., Structure-activity relationship within a series of pyrazolidinone antibacterial agents. 2. Effect of side-chain modification on in-vitro activity and pharmacokinetic parameters, Journal of Medicinal Chemistry, vol. 36, 3224-3229, 1993 (Year: 1993).*

(Continued)

*Primary Examiner* — Kortney L. Klinkel
*Assistant Examiner* — Padmaja S Rao
(74) *Attorney, Agent, or Firm* — Saul Ewing LLP; Kathryn Doyle; Domingos J. Silva

(57) ABSTRACT

In one aspect, the invention provides compounds and methods that are useful for treating bacterial infections:

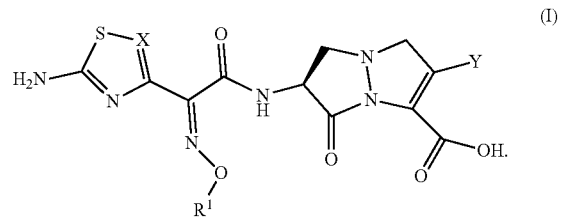

17 Claims, 12 Drawing Sheets

(51) Int. Cl.
*A61K 9/00* (2006.01)
*A61K 31/427* (2006.01)
*A61K 31/4439* (2006.01)

(56) References Cited

OTHER PUBLICATIONS

Page, Siderophore conjugates, Annals of the New York Academy of Sciences, Antimicrobial Therapeutics Reviews, vol. 1277, 115-126, 2013 (Year: 2013).*

* cited by examiner

Synthesis of Pyridone-Based Siderophore Mimetics

FIG. 3A

| Organism | MMX[1] ATCC[2] No. | Phenotype | MIC (μg/mL) | | | | | |
|---|---|---|---|---|---|---|---|---|
| | | | MSP2-128 | MSP2-128 (no Iron) | MSP2-133 | MSP2-133 (no Iron) | MSP2-147 | MSP2-147 (no Iron) |
| E. coli | 102 25922 | QC | >128 | >128 | 16 | 8 | 8 | 4 |
| E. coli | 5684 13352 | TEM-10; BLA | >128 | >128 | 8 | 8 | 16 | 2 |
| E. coli [4] | 6839 BAA-2326 | CTX-M-15; BLA | >128 | >128 | 8 | 8 | 8 | 1 |
| E. coli | 5980 | NDM-1 carbapenemase | >128 | >128 | 64 | 32 | 32 | 4 |
| E. coli | 119 | Parent TolC knockout | >128 | >128 | 8 | 8 | 8 | 1 |
| E. coli | 121 | TolC knockout; outer membrane protein that efflux pumps use to pump drugs out | 16 | 32 | 1 | 2 | 0.015 | 0.03 |
| K. pneumoniae | 537 700063 | SHV-1; BLA | >128 | >128 | 8 | 8 | 16 | 4 |
| K. pneumoniae | 4683 | KPC-2 carbapenemase | >128 | >128 | 32 | 8 | 32 | 2 |
| E. cloacae [4] | 7941 | AmpC; BLA | >128 | >128 | 64 | 16 | >128 | 8 |
| E. cloacae [4] | 5981 | NDM-1 | >128 | >128 | >128 | >128 | >128 | >128 |
| P. aeruginosa [4] | 103 27853 | QC | >128 | >128 | 32 | >128 | >128 | >128 |
| P. aeruginosa [4] | 3476 | Parent mexAB/oprM knockout | >128 | >128 | 32 | >128 | >128 (2)[2] | 4 [3] |
| P. aeruginosa | 3477 | mexAB/oprM knockout; mexAB pump deleted, also oprM outer membrane protein | >128 | >128 | 4 | 1 | >128 (1)[2] | 2 |
| P. aeruginosa | 4698 | VIM-2; metallo-beta lactamase | >128 | >128 | 32 | >128 | >128 | >128 |
| P. aeruginosa | 4654 | IMP-7; metallo-beta lactamase | >128 | >128 | >128 | >128 | >128 | >128 |
| A. baumannii | 1630 19606 | Wild type | >128 | >128 | 32 | >128 | 16 | 8 |
| A. baumannii | 4651 | OXA-27; metallo-beta lactamase | >128 | >128 | 16 | >128 | 16 | 1 |

FIG. 3B

| Organism | MMX[1] ATCC[2] No. | Phenotype | MIC (µg/mL) | | | | | | | |
|---|---|---|---|---|---|---|---|---|---|---|
| | | | MSP2-154 | MSP2-154 (no Iron) | Meropenem | Meropenem (no Iron) | Ceftazidime | Ceftazidime (no Iron) | Aztreonam | Aztreonam (no Iron) |
| E. coli | 102 25922 | QC | 64 | 128 | 0.015 (0.008-0.06)[1] | 0.015 | 0.5 (0.06-0.5) | 0.25 | 0.12 (0.06-0.25) | 0.25 |
| E. coli | 5684 13352 | TEM-10; BLA | >128 | 128 | 0.03 | 0.06 | >32 | 32 | 8 | 8 |
| E. coli [4] | 6839 BAA-2326 | CTX-M-15; BLA | >128 | 16 | 0.015 | 0.015 | 32 | 32 | 16 | 16 |
| E. coli | 5980 | NDM-1 carbapenemase | >128 | >128 | 16 | 16 | >32 | >32 | 16 | 8 |
| E. coli | 119 | Parent TolC knockout | 64 | 16 | 0.015 | 0.015 | 0.25 | 0.12 | 0.12 | 0.12 |
| E. coli | 121 | TolC knockout; outer membrane protein that efflux pumps use to pump drugs out | 4 | 1 | 0.03 | 0.03 | 0.25 | 0.25 | 0.12 | 0.12 |
| K. pneumoniae | 537 700063 | SHV-1; BLA | 64 | 64 | 0.015 | 0.03 | 32 | 32 | 16 | 32 |
| K. pneumoniae | 4683 | KPC-2 carbapenemase | 64 | 8 | 16 | 16 | >32 | >32 | >32 | >32 |
| E. cloacae [4] | 7941 | AmpC; BLA | 128 | 32 | 0.12 | 0.12 | >32 | >32 | >32 | >32 |
| E. cloacae [4] | 5981 | NDM-1 | >128 | >128 | >32 | >32 | >32 | >32 | >32 | 32 |
| P. aeruginosa [4] | 103 27853 | QC | 32 | >128 | 0.5 (0.25-1) | 0.25 | 2 (1-4) | 1 | 4 (2-8) | 8 |
| P. aeruginosa [4] | 3476 | Parent mexAB/oprM knockout | 32 | >128 | 0.5 | 0.25 | 1 | 1 | 2 | 2 |
| P. aeruginosa | 3477 | mexAB/oprM knockout; mexAB pump deleted, also oprM outer membrane protein | 8 | 128 | 0.12 | 0.12 | 0.5 | 0.5 | 0.25 | 0.25 |
| P. aeruginosa | 4698 | VIM-2; metallo-beta lactamase | >128 | >128 | >32 | >32 | 32 | 32 | 8 | 8 |
| P. aeruginosa | 4654 | IMP-7; metallo-beta lactamase | >128 | >128 | >32 | >32 | >32 | >32 | 16 | 8 |
| A. baumannii | 1630 19606 | Wild type | >128 | >128 | 1 | 1 | 8 | 8 | 32 | 32 |
| A. baumannii | 4651 | OXA-27; metallo-beta lactamase | >128 | >128 | 32 | 16 | >32 | >32 | 32 | 32 |

FIG. 7

| Bacterial Species | β-Lactamase Genes | VU253434-Susceptible* | Ceftazidime-Susceptible* | Imipenem-Susceptible* |
|---|---|---|---|---|
| E. coli | all contain combinations of $bla_{SHV}$, $bla_{KPC}$, $bla_{CTX-M}$, $bla_{AmpC}$ and $bla_{TEM}$ | 11/15 | 6/15 | 3/15 |
| K. pneumoniae | all contain combinations of $bla_{SHV}$, $bla_{KPC}$, $bla_{CTX-M}$ and $bla_{TEM}$ | 13/15 | 2/15 | 6/15 |
| P. aeruginosa | all contain combinations of $bla_{KPC}$, $bla_{AmpC}$, and $bla_{OXA}$ | 10/15 | 0/15 | 0/15 |

*Susceptibilities: VU253434 arbitrarily used ceftazidime breakpoints: $\leq 4$ μg/mL for Enterobacteriaceae and $\leq 8$ μg/mL for P. aeruginosa; imipenem: $\leq 1$ μg/mL for Enterobacteriaceae and $\leq 2$ μg/mL for P. aeruginosa

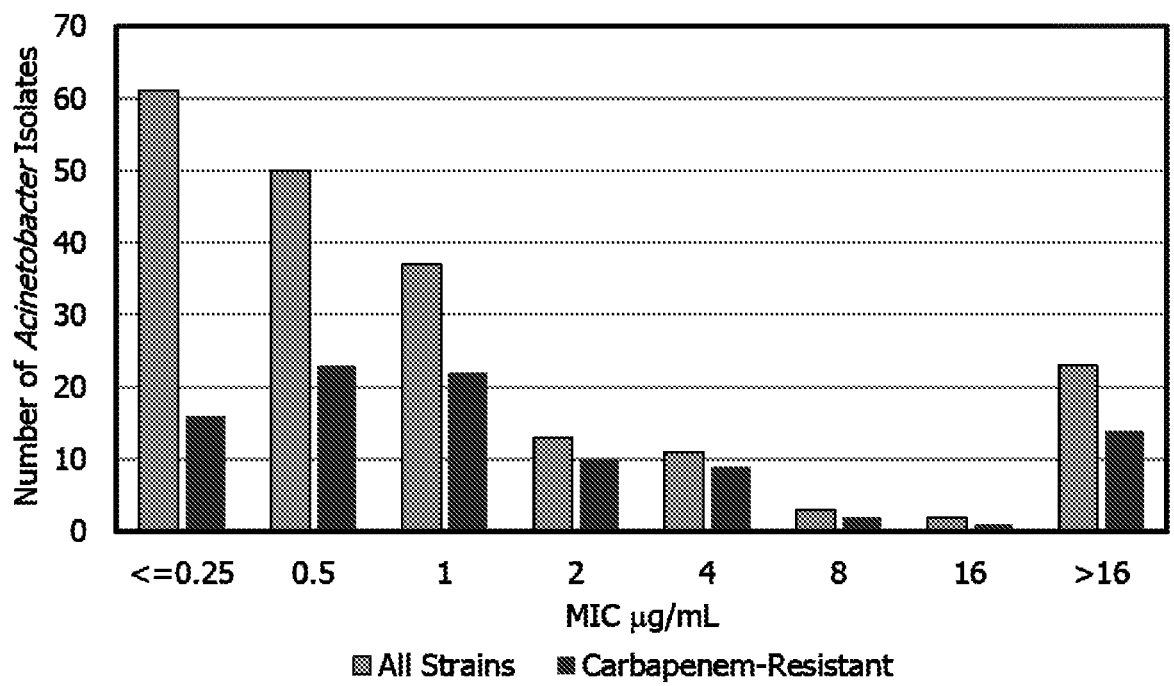

SIDEROPHORE CONJUGATED PYRAZOLIDINONES, AND ANALOGUES THEREOF

CROSS-REFERENCE TO RELATED APPLICATIONS

The present application is a 35 U.S.C. § 371 national phase application from, and claims priority to, PCT International Patent Application No. PCT/US2019/042643, filed Jul. 19, 2019, which claims priority under 35 U.S.C. § 119(e) to U.S. Provisional Application No. 62/701,249, filed Jul. 20, 2018, all of which are incorporated herein by reference in their entireties.

BACKGROUND OF THE INVENTION

Gram-negative pathogens possessing pan-drug resistance or extreme drug resistance (PDR or XDR) are becoming more prevalent, with strains already identified that are resistant to all known antibiotics and are effectively untreatable. These include WHO priority 1 pathogens such as *Acinetobacter baumannii* (Ab), *Pseudomonas aeruginosa* (Pa), *Klebsiella pneumoniae* (Kp), and Enterobacteriaceae which possess plasmid-mediated carbapenemases (β-lactamases: NDM-1, KPC and OXA-type class D carbapenemases), making their infections nearly untreatable with β-lactam antibiotics such as carbapenems and 3$^{rd}$ generation cephalosporins.

Two million infections each year in the United States are caused by antibiotic resistant bacteria, resulting in approximately 25,000 deaths and $20 billion in healthcare costs. The World Health Organization (WHO) projects this global crisis will continue to grow and cause 10 million deaths per year and a cumulative cost of $100 trillion by 2050. New antibacterial agents are needed to effectively treat infections caused by these multi-drug resistant (MDR) pathogens.

Gram-negative bacteria are characterized by cell envelopes composed of a thin peptidoglycan cell wall sandwiched between an inner cytoplasmic cell membrane and a bacterial outer membrane. This outer membrane protects Gram-negative bacteria from many antibiotics (including penicillin) due to its high negative charge and low permeability.

There is thus a need in the art for such new and potent treatments for antibiotic resistant Gram negative microbial infections. The present invention addresses this need.

SUMMARY OF THE INVENTION

In one aspect, the invention provides a compound of formula (I), or a salt, solvate, enantiomer, diastereoisomer, tautomer, or geometric isomer thereof:

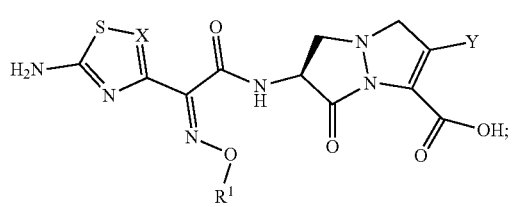

wherein $R^1$ is selected from the group consisting of:

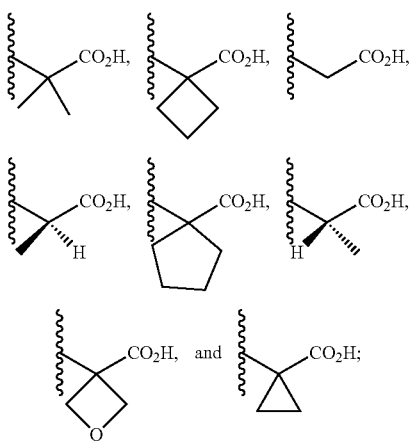

X is selected from the group consisting of CH, CF, CCl, and N;

Y is selected from the group consisting of:

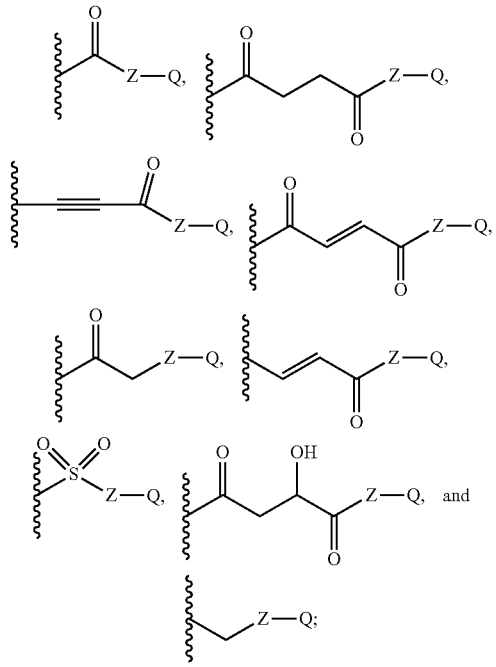

Z is a divalent group selected from the group consisting of —NH—, —NMe-, —O— and —S—;

and Q is a siderophore or a siderophore mimic.

In various embodiments, Q is selected from the group consisting of:

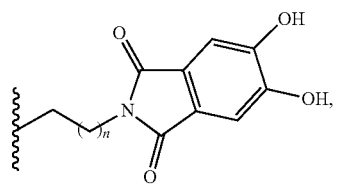

-continued
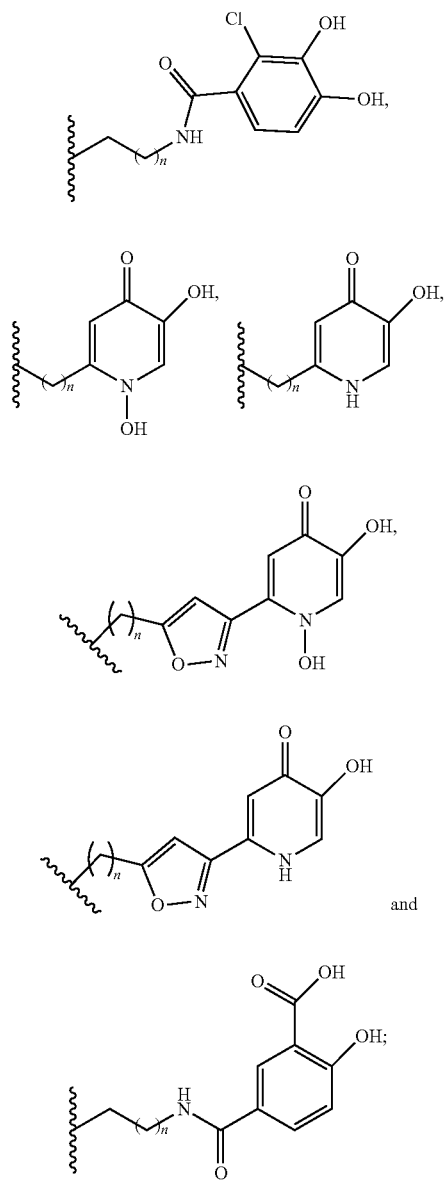
wherein each occurrence of n is independently selected from the group consisting of 0-3; or a salt, solvate, enantiomer, diastereoisomer, or tautomer thereof.
In various embodiments, $R^1$ is selected from the group consisting of:
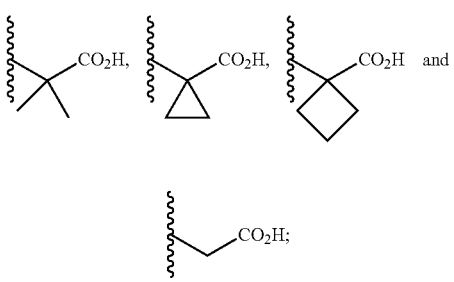
wherein Y is selected from the group consisting of:
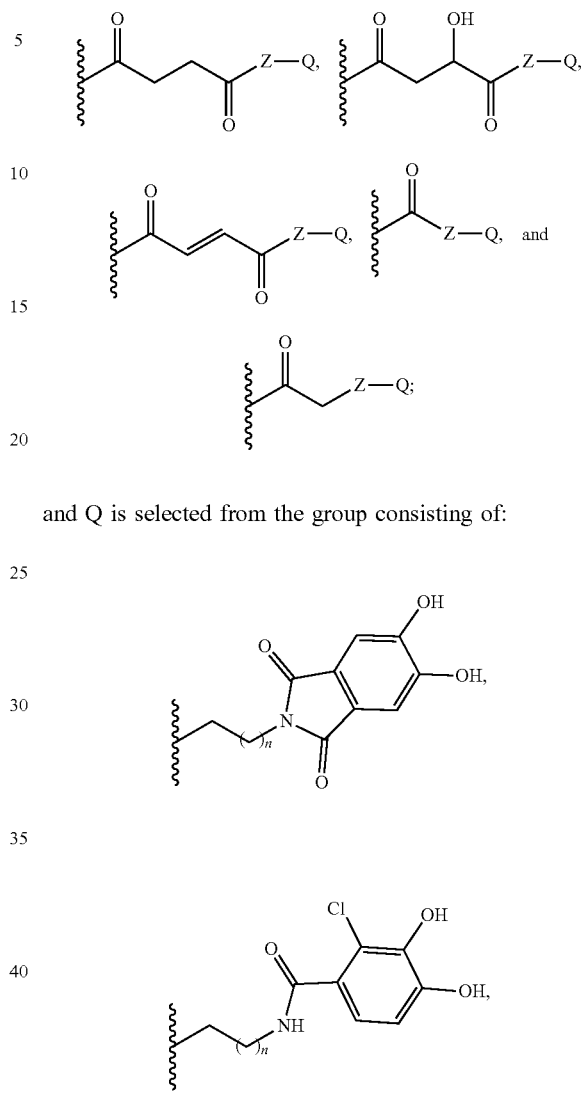
and Q is selected from the group consisting of:
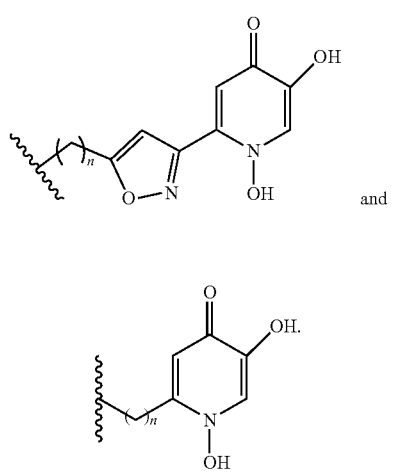

In various embodiments, the compound is selected from the group consisting of:

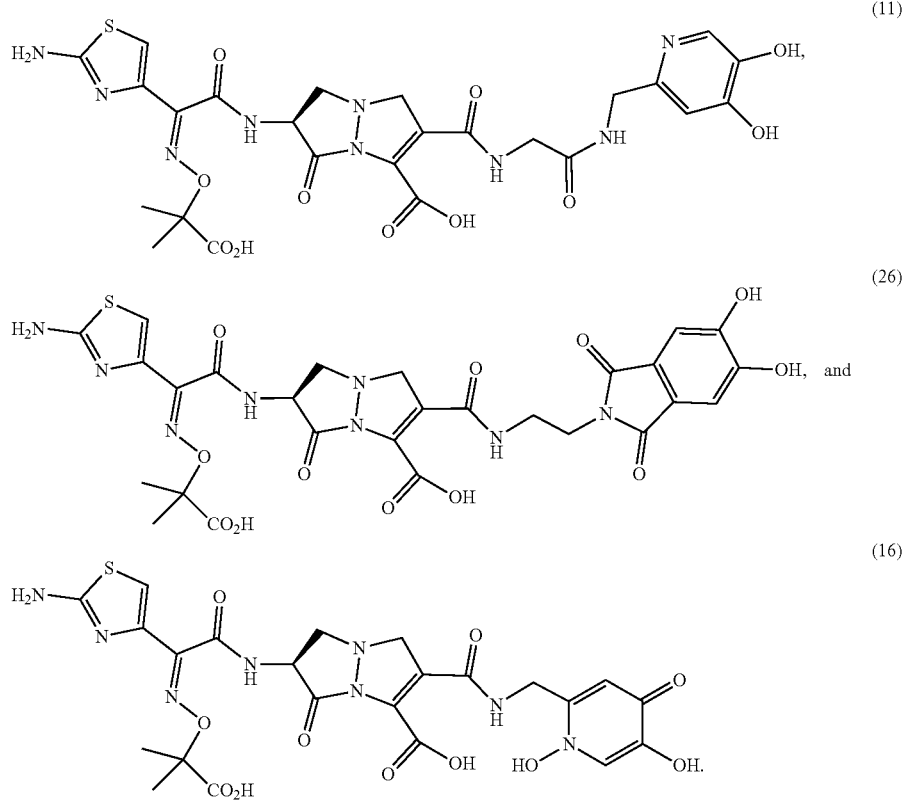

In various embodiments, the compound is:

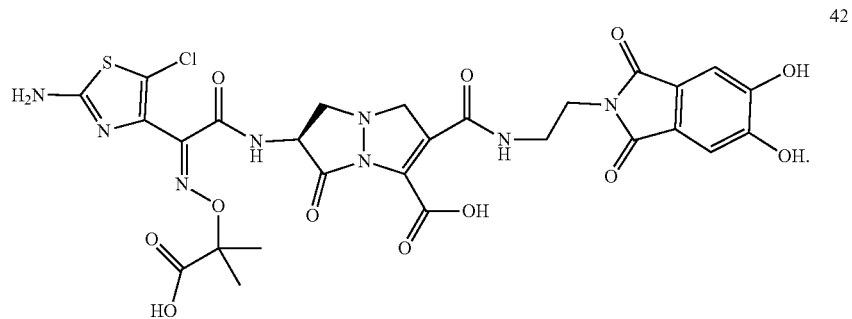 [SMILES: CC(C)(O/N=C(\C(=O)N[C@H]1CN2CC(C(=O)NCCN3C(=O)c4cc(O)c(O)cc4C3=O)=C(C(=O)O)N2C1=O)c1nc(N)sc1Cl)C(=O)O]

In various embodiments, the invention provides a pharmaceutical composition comprising a compound of the invention and at least one pharmaceutically acceptable carrier. In various embodiments, the pharmaceutical composition is formulated for intravenous injection.

In various embodiments, the invention provides a method of treating or preventing a bacterial infection in a subject in need thereof, comprising administering to the subject an effective amount of a compound of the invention.

In various embodiments, the bacterial infection is caused by a Gram negative bacterium.

In various embodiments, the bacterial infection is caused by an antibiotic resistant bacterium.

In various embodiments, the bacterial infection is caused by at least one selected from the group consisting of *Acinetobacter baumannii*, *Pseudomonas aeruginosa*, and *Klebsiella pneumoniae*.

In various embodiments, the bacterial infection is a nosocomial infection.

In various embodiments, the compound is administered to the subject as part of a pharmaceutical composition. In various embodiments, the pharmaceutical composition is formulated for intravenous injection.

In various embodiments, the subject is further administered at least one additional agent to treat or prevent the bacterial infection.

In various embodiments, the subject is administered the compound intravenously.

In various embodiments, the subject is a mammal.

BRIEF DESCRIPTION OF THE DRAWINGS

The following detailed description of illustrative embodiments of the invention will be better understood when read in conjunction with the appended drawings. For the purpose of illustrating the invention, certain illustrative embodiments are shown in the drawings. It should be understood, however, that the invention is not limited to the precise arrangements and instrumentalities of the embodiments shown in the drawings.

FIGS. 3A-3B comprise a table depicting antimicrobial activity of compounds of the invention. Legend: [1] CLSI QC range listed in parenthesis; [2] Growth was significantly lower at the concentration in parenthesis; [3] Concentrations of 4, 8 and 16 micrograms/mL showed clear wells; growth returned from 32 up to 128 micrograms/mL; [4] significantly lighter growth without iron; BLA: beta lactamase; underlined values indicate 4-fold or greater decrease in the MIC

FIG. 7 is a table of beta lactamase genes presented by species with comparison of fraction susceptible to compound 26 (YU253434) versus ceftazidime and imipenem.

FIGS. 8A-8B show YU253911 (compound 42) $MIC_{50}$ and $MIC_{90}$ values derived from 200 *Acenitobacter baumannii* isolates (FIG. 8A) compared to clinical agents (FIG. 8B).

DETAILED DESCRIPTION OF THE INVENTION

Figure 1:
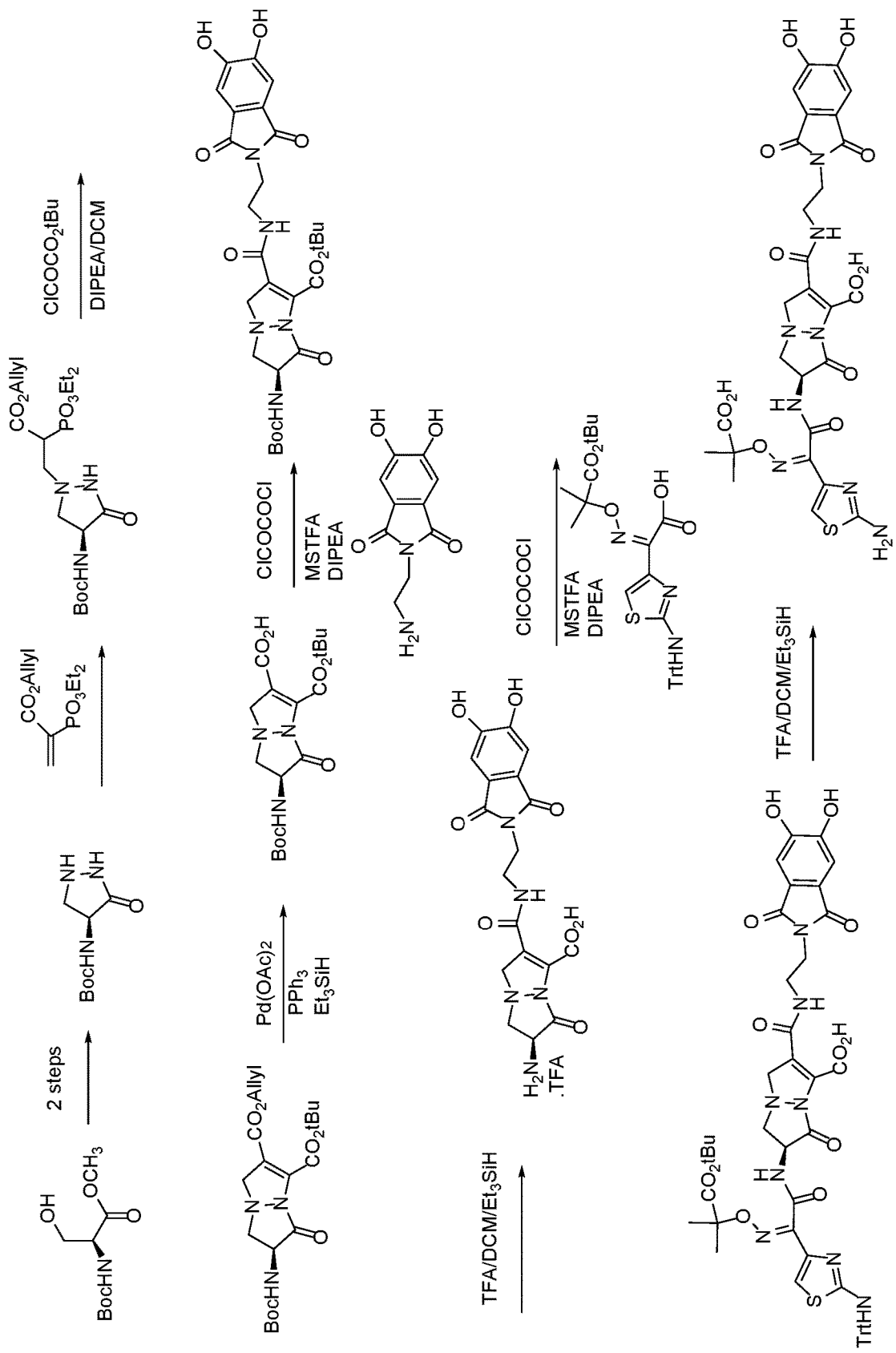
FIG. 1 is a synthetic scheme illustrating synthesis of compounds of the invention.

The invention provides novel compounds that are useful for treating bacterial infections, such as but not limited to Gram-negative bacterial infections. In certain embodiments, the compounds of the invention comprise conjugates of a pyrazolidinone and a siderophore.

Without wishing to be limited by theory, conjugating pyrazolidinones to a siderophore using novel linkers allows for active transport of the pyrazolidinone into the periplasmic space of Gram negative bacteria, where the compound inhibits penicillin binding proteins, while also greatly mitigating beta lactamase hydrolytic liability. Accordingly, in various aspects and embodiments the invention provides novel antibacterial agents and methods of treating antibacterial infection using the same.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, selected methods and materials are described. As used herein, each of the following terms has the meaning associated with it in this section.

Generally, the nomenclature used herein and the laboratory procedures in cell culture, molecular genetics, pharmacology, and organic chemistry are those well-known and commonly employed in the art.

Standard techniques are used for biochemical and/or biological manipulations. The techniques and procedures are generally performed according to conventional methods in the art and various general references (e.g., appropriate methods and standards as maintained by the Clinical and Laboratory Studies Institute: clsi dot org/), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "analog," "analogue," or "derivative" are meant to refer to a chemical compound or molecule made from a parent compound or molecule by one or more chemical reactions. As such, an analog can be a structure having a structure similar to that of the small molecules described herein or can be based on a scaffold of a small molecule described herein, but differing from it in respect to certain components or structural makeup, which may have a similar or opposite action metabolically.

As used herein, the term "binding" refers to the adherence of molecules to one another, such as, but not limited to, enzymes or any other proteins to substrates, antibodies to antigens, DNA strands to their complementary strands. Binding occurs because the shape and chemical nature of parts of the molecule surfaces are complementary. A common metaphor is the "lock-and-key" used to describe how enzymes fit around their substrate.

A "disease" is a state of health of an animal, such as a human subject, wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" of a compound, as used herein, is that amount of compound which is sufficient to achieve the intended effect, typically, treatment or prevention of a disease or disorder, when provided to the patient by a particular method of administration.

An appropriate effective amount in any individual case may be determined by one of ordinary skill in the art using routine experimentation and the material disclosed herein.

As used herein, the phrase "a first compound is essentially free of a second compound" in a composition indicates that the ratio of the second compound to the first second compound in the composition is about 10:90, 5:95, 4:96, 3:97, 2:98, 1:99, 0.5:99.5, 0.25:99.75, 0.1:99.9, 0.05:99.95, 0.025:99.975, 0.01:99.99 or 0:100.

As used herein, the term "halide" refers to a halogen atom bearing a negative charge. The halide anions are fluoride ($F^-$), chloride ($Cl^-$), bromide ($Br^-$), and iodide ($I^-$).

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

As used herein, the terms "pharmaceutically acceptable carrier" and "pharmaceutically acceptable excipient" are used interchangeably and mean a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compounds prepared from pharmaceutically acceptable non-toxic acids, including inorganic acids or bases, organic acids or bases, solvates, hydrates, or clathrates thereof.

By the term "specifically binds," as used herein, is meant a molecule, such as an antibody, which recognizes and binds to another molecule or feature, but does not substantially recognize or bind other molecules or features in a sample.

As used herein, the term "substituted" refers to that an atom or group of atoms has replaced hydrogen as the substituent attached to another group.

As used herein, the term "substituted alkyl," "substituted cycloalkyl," "substituted alkenyl" or "substituted alkynyl" refers to alkyl, cycloalkyl, alkenyl or alkynyl, as defined elsewhere herein, substituted by one, two or three substituents independently selected from the group consisting of halogen, —OH, alkoxy, tetrahydro-2-H-pyranyl, —$NH_2$, —$NH(C_1$-$C_6$ alkyl), —$N(C_1$-$C_6$ alkyl)$_2$, 1-methyl-imidazol-2-yl, pyridin-2-yl, pyridin-3-yl, pyridin-4-yl, —C(=O)OH, —C(=O)O($C_1$-$C_6$)alkyl, trifluoromethyl, —C≡N, —C(=O)$NH_2$, —C(=O)NH($C_1$-$C_6$)alkyl, —C(=O)N(($C_1$-$C_6$)alkyl)$_2$, —$SO_2NH_2$, —$SO_2$NH($C_1$-$C_6$ alkyl), —$SO_2$N($C_1$-$C_6$ alkyl)$_2$, —C(=NH)$NH_2$, and —$NO_2$, in certain embodiments containing one or two substituents independently selected from halogen, —OH, alkoxy, —$NH_2$, trifluoromethyl, —N($CH_3$)$_2$, and —C(=O)OH, in certain embodiments independently selected from halogen, alkoxy and —OH. Examples of substituted alkyls include, but are not limited to, 2,2-difluoropropyl, 2-carboxycyclopentyl and 3-chloropropyl.

Unless otherwise noted, when two substituents are taken together to form a ring having a specified number of ring atoms (e.g., two groups taken together with the nitrogen to which they are attached to form a ring having from 3 to 7 ring members), the ring can have carbon atoms and optionally one or more (e.g., 1 to 3) additional heteroatoms independently selected from nitrogen, oxygen, or sulfur. The ring can be saturated or partially saturated, and can be optionally substituted.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 and so forth, as well as individual numbers within that range, for example, 1, 2, 2.7, 3, 4, 5, 5.3, and 6. This applies regardless of the breadth of the range.

Disclosure

One method for overcoming the issue of penetration into Gram-negative bacteria is to hijack active transport mechanisms of the bacteria. For example, the active transport of iron is fundamental to bacterial survival. Although iron is an abundant element in nature, it is extremely insoluble, and within the body it is tightly regulated and bound to heme or proteins. To access iron during an infection, since there is no free iron available for bacteria to use for growth, bacteria produce siderophores. These small organic compounds chelate and scavenge iron from the host's body and are then actively transported, by numerous transporters, into the bacteria. Currently there are over 500 known bacterial siderophores that generally contain structures like hydroxamates, catechols, carboxylates, and various heterocycles.

It is not necessary for a siderophore to have chelated iron to be recognized by transporters and imported, as one bacterial species can pirate the siderophores of another bacterial species as a method of self-defense and selfpromotion. It has also been found that complete siderophores from bacteria are not needed for transporter recognition and passage into the bacteria. Thus, simple siderophore fragments and mimics are transported. Siderophores, or any fragments and/or mimics thereof, have been covalently linked to antibacterial agents fostering transport of the agent into the bacteria, increasing its effectiveness in a so called "Trojan horse" strategy. Nature already uses this defense strategy with the sideromycins produced by some bacteria.

Pyrazolidinones are synthetic antibacterial agents first described by Eli Lilly company in the 1980's. These compounds bind and inhibit penicillin binding proteins (PBPs), the target of all penicillin, cephalosporin and carbapenem antibiotics. The pyrazolidinones described by Lilly contain no siderophore and were found to inhibit Gram positive bacterial growth with only weak activity against Gram negative pathogens while being susceptible to beta-lactamase hydrolysis. In contrast this work uses a siderophore, or any fragment and/or mimic thereof, to promote Gram negative penetration and mitigate beta lactamase hydrolysis. When a siderophore, or a fragment and/or mimic thereof, are appended appropriately, one can promote the penetration of a pyrazolidinone into Gram negative bacteria by >100 fold. In certain embodiments, siderophores, or fragments and/or mimics thereof, are substituted in such a manner as to allow covalent linking to the pyrazolidinone core. In certain embodiments, the siderophores, or any fragments and/or mimics, that are contemplated in the invention can be derivatives of siderophores found in nature that are suitably substituted to provide a covalent link to the pyrazolidinone core. Often less than a fully elaborated natural siderophore is required for receptor recognition and transport; such active fragments are useful within the invention when covalently linked to the pyrazolidinone. Likewise, fully synthetic and/or unnatural siderophore mimics can be covalently linked to the pyrazolidinone core resulting in enhanced transport into the periplasmic space of the Gram negative bacteria.

Additionally, the siderophore, or a fragment or mimic thereof, appended to the pyrazolidinone via a rigid linker attachment results in avoidance of beta-lactamase hydrolysis, the major resistance mechanism by which PBP inhibitors are disabled. For avoiding beta lactamase hydrolysis, in various embodiments the siderophore or mimic is appended to the appropriate location on the pyrazolidinone with a rigid linker. The siderophore combined with the pyrazolidinone then is unable to bind to and be hydrolyzed by beta lactamases due to their rather closed active site. However, such compounds can bind to the target PBPs due to the open active site of the PBP which are transpeptidases. The significant increase in penetration, combined with mitigation of beta-lactamase hydrolysis, is the result of judicious and optimized structure based design producing pyrazolidinones with previously unknown growth inhibition of WHO priority 1 pathogens. In addition to these remarkable advantages, pyrazolidinone with an appended siderophore, or any fragment and/or mimic thereof, are fully tunable allowing the practitioner to optimize stability, reactivity and bacterial permeability.

Compounds

In one aspect, the invention provides a compound of formula (I), or a salt, solvate, enantiomer, diastereoisomer, tautomer, or geometric isomer thereof:

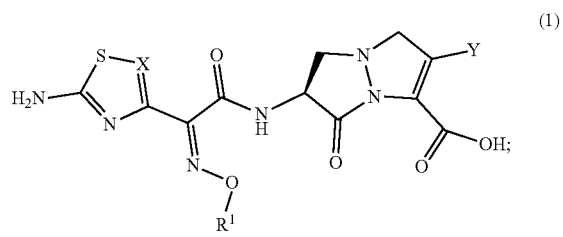

wherein:
$R^1$ is selected from the group consisting of:

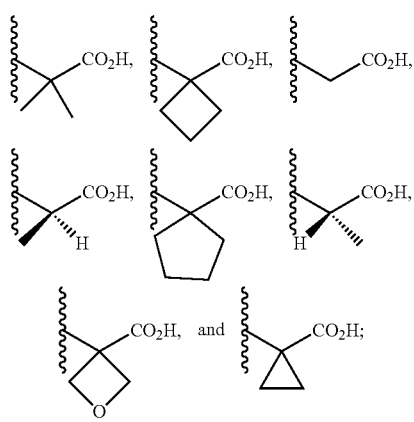

X is selected from the group consisting of CH, CF, CCl and N;
Y is selected from the group consisting of:

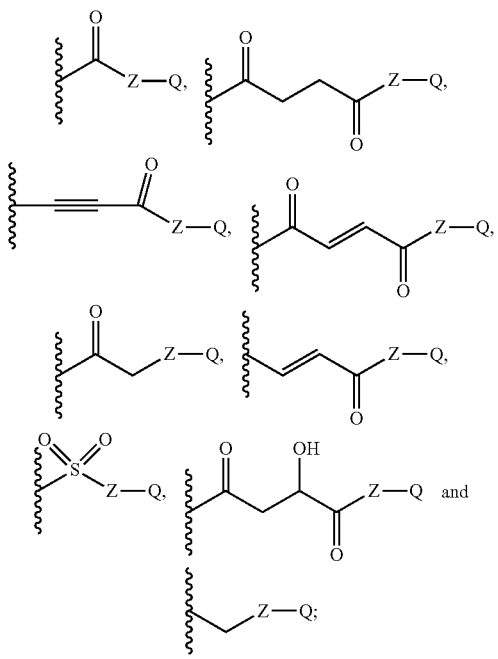

Z is a divalent group selected from the group consisting of —NH—, —NMe-, —O— and —S—; and
Q is a Gram negative bacteria siderophore, a mimic thereof, or any biologically active substructures thereof. As used herein, "siderophore" refers to a low molecular weight iron chelator that is synthesized by a microbe for the purpose of sequestering iron and delivering iron to the microbe by active transport. Such naturally occurring siderophores can be used for the purposes of enhancing penetration of the pyrazolidinones disclosed in this invention. In various embodiments, natural siderophores are modified so that they can be conjugated to the pyrazolidinone; such modifications include introducing an alcohol, amine, thiol, or carboxylic acid in their structures, thus allowing their conjugation with a pyrazolidinone through an ether, ester, amide, amine, thioether, disulfide, or carboxamide linker. Q is covalently linked to the pyrazolidinone, and acts to increase translocation of the agent into the periplasmic space of Gram negative bacteria. Currently there are over 500 known bacterial siderophores that contain structures like hydroxamates, catechols, carboxylates, and various heterocycles, all of which can be used within the present invention. Accordingly, in various embodiments Q comprises at least one hydroxamate, catechol, carboxylate or heterocycle.

A siderophore mimic is: (a) a low molecular weight molecule that is a "functional" fragment of a natural siderophore, and/or (b) a true synthetic low molecular weight molecule that is not derived from a microbe and serves as a true mimetic. Non-limiting examples of the latter (b) include 2-hydroxypyridones and 2,3 dihydroxyphthalimide derivatives. Accordingly, in various embodiments Q is a 2-hydroxypyridone derivative or a 2,3 dihydroxyphthalimide derivative. In the case of (a) true iron chelation is not fundamental within the present invention; "functional" fragment as defined herein refers to a fragment that is recognized and actively transported into the bacteria. In each case the siderophore mimic has (or is derivatized with) an alcohol, amine, thiol, or carboxylic acid in its structure, thereby allowing for linking with a pyrazolidinone through an ether, ester, amide, amine, thioether, disulfide, or carboxamide linker.

In various embodiments, Q is selected from the group consisting of:

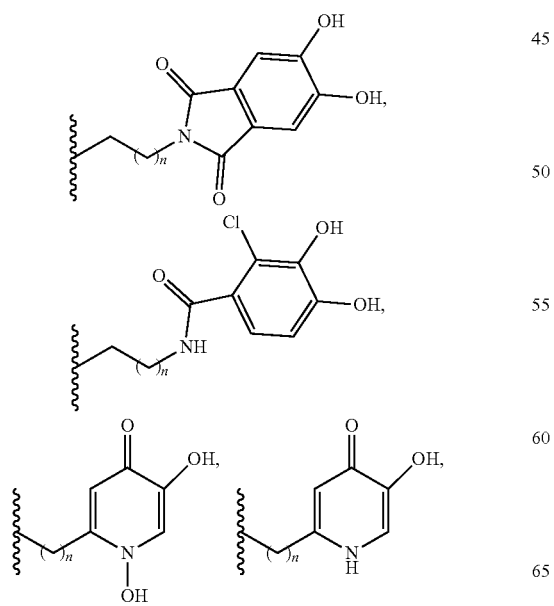

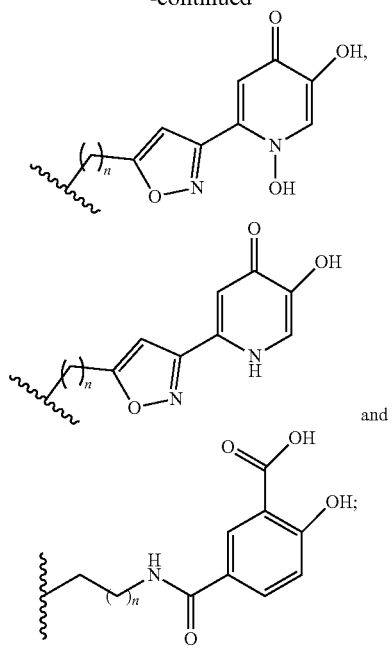

wherein each occurrence of n is independently selected from the group consisting of 0-3; or a salt, solvate, enantiomer, diastereoisomer, or tautomer thereof.

In various embodiments, Y is selected from the group consisting of:

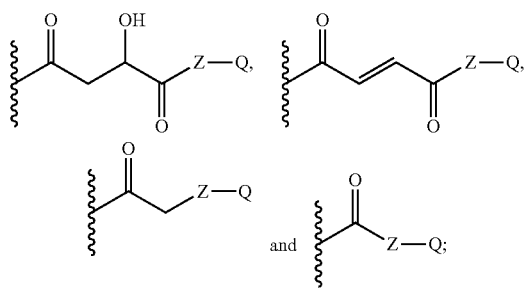

wherein Z is defined as above; and Q is selected from the group consisting of:

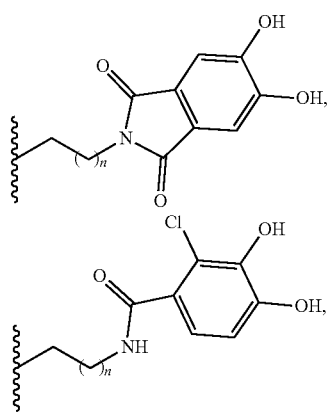

-continued

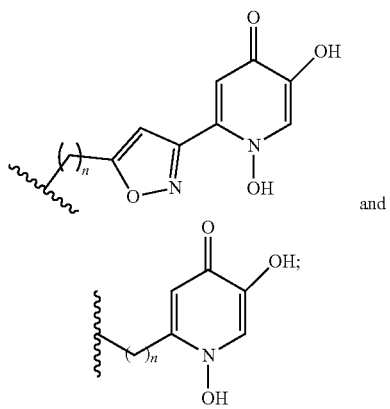

and wherein each occurrence of n is independently selected from the group consisting of 0-3;
or a salt, solvate, enantiomer, diastereoisomer, or tautomer thereof.

In various embodiments, the compound is selected from the group consisting of:

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced (11)

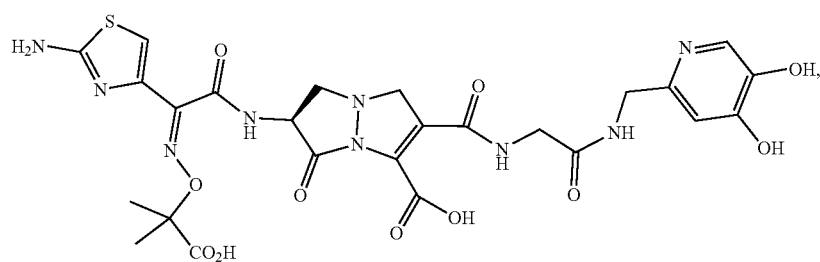

(26)

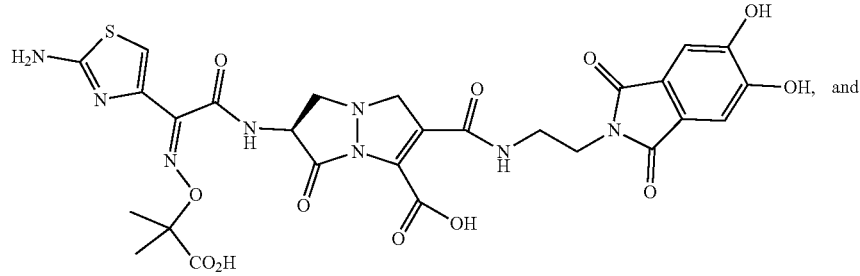

(16)

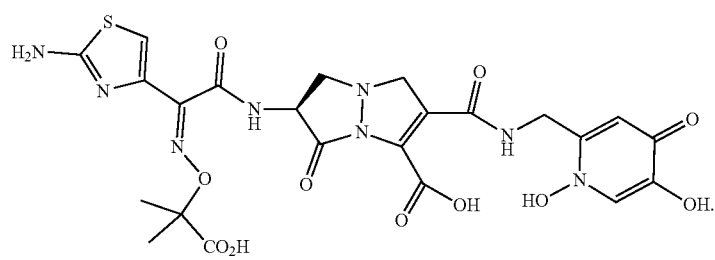

The compounds of the invention may be incorporated into a variety of pharmaceutical compositions for administration by a variety of routes of administration. A pharmaceutical composition according to the invention can comprise a compound of the invention, and at least one pharmaceutically acceptable carrier. In various embodiments, the pharmaceutical composition is formulated for intravenous injection.

by an atom having the same atomic number, but an atomic mass or mass number different from the atomic mass or mass number usually found in nature. Examples of isotopes suitable for inclusion in the compounds described herein include and are not limited to $^2H$, $^3H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

In various embodiments, the compounds of the invention may be incorporated into a pharmaceutical composition comprising at least one pharmaceutically acceptable excipient. In various embodiments, the pharmaceutical composition is formulated for intravenous injection. Dosage, administration and formulation is discussed elsewhere herein.

Salts

The compounds described herein may form salts with acids or bases, and such salts are included in the present invention. The term "salts" embraces addition salts of free acids or bases that are useful within the methods of the invention. The term "pharmaceutically acceptable salt" refers to salts that possess toxicity profiles within a range that affords utility in pharmaceutical applications. In certain embodiments, the salts are pharmaceutically acceptable salts. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable base addition salts of compounds of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from tertiary amines. All of these salts may be prepared from the corresponding compound by reacting, for example, the appropriate acid or base with the compound.

Methods

In another aspect, the invention provides a method of treating or preventing a bacterial infection in a subject in need thereof, comprising administering to the subject an effective amount of at least one compound of the invention. The compound may be administered to the subject as part of a pharmaceutical composition by any appropriate route of administration, as discussed in further detail below, depending on the nature and severity of the bacterial infection. In various embodiments, the subject is administered the compound by at least one route selected from the group consisting of oral, nasal, rectal, parenteral, sublingual, transdermal, transmucosal, intravesical, intrapulmonary, intraduodenal, intragastrical, intrathecal, epidural, intrapleural, intraperitoneal, subcutaneous, intramuscular, intradermal, intra-arterial, intravenous, intrabronchial, inhalation, and topical.

The compounds of the invention are effective against a wide variety of bacteria. In various embodiments, the bacterial infection is caused by a Gram negative bacterium. In various embodiments, the bacterial infection is caused by a Gram positive bacterium. The compounds may bypass certain mechanisms of bacterial antibiotic resistance, including but not limited to hydrolysis by beta lactamases. In various embodiments, the bacterial infection is caused by an antibiotic resistant bacterium. In various embodiments, the bacterial infection is caused by at least one bacteria selected from the group consisting of *Acinetobacter baumannii*, *Pseudomonas aeruginosa*, and *Klebsiella pneumoniae*. Antibiotic resistant bacterial infections are a significant and growing problem in a hospital setting and the compounds of the invention are useful for treating such infections. In various embodiments, the bacterial infection is a nosocomial infection.

Combination Therapies

In one aspect, the compounds of the invention are useful within the methods of the invention in combination with one or more additional agents useful for treating diseases or disorders disclosed herein. These additional agents may comprise compounds or compositions identified herein, or compounds (e.g., commercially available compounds) known to treat, prevent, or reduce the symptoms of diseases or disorders disclosed herein.

In certain embodiments, the compounds of the invention can be used in combination with other antibacterial agents. In various embodiments, the subject is further administered at least one additional agent to treat or prevent the bacterial infection.

The compounds of the invention may also be administered in combination with other agents to promote the health or comfort of the patient, by way of non-limiting example pain killers or anti-inflammatory agents.

The compounds of the invention may be used effectively on a wide variety of subjects. In various embodiments, the subject is a mammal. In various embodiments, the subject is a human. In various embodiments the subject is a hospital patient.

Administration/Dosage/Formulations

Administration of the compounds and/or compositions of the present invention to a patient, preferably a mammal, more preferably a human, may be carried out using known procedures, at dosages and for periods of time effective to perform the methods contemplated in the invention. An effective amount of the compound necessary may vary according to factors such as the state of a disease or disorder in the patient; the age, sex, and weight of the patient. One of ordinary skill in the art would be able to study the relevant factors and make the determination regarding the effective amount of the compound without undue experimentation.

Actual dosage levels of the active ingredients in the pharmaceutical compositions of this invention may be varied so as to obtain an amount of the active ingredient that is effective to achieve successful treatment for a particular patient, composition, and mode of administration, without being toxic to the patient.

In certain embodiments, the compositions of the invention are formulated using one or more pharmaceutically acceptable excipients or carriers. In certain embodiments, the pharmaceutical compositions of the invention comprise an effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments therebetween.

In certain embodiments, the dose of a compound of the invention is from about 1 mg and about 2,500 mg. In certain embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., anti-fibrotic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 2003/0147952; 2003/0104062; 2003/0104053; 2003/0044466; 2003/0039688; and 2002/0051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Those skilled in the art will recognize, or be able to ascertain using no more than routine experimentation, numerous equivalents to the specific procedures, embodiments, claims, and examples described herein. Such equivalents are considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Figure 2:
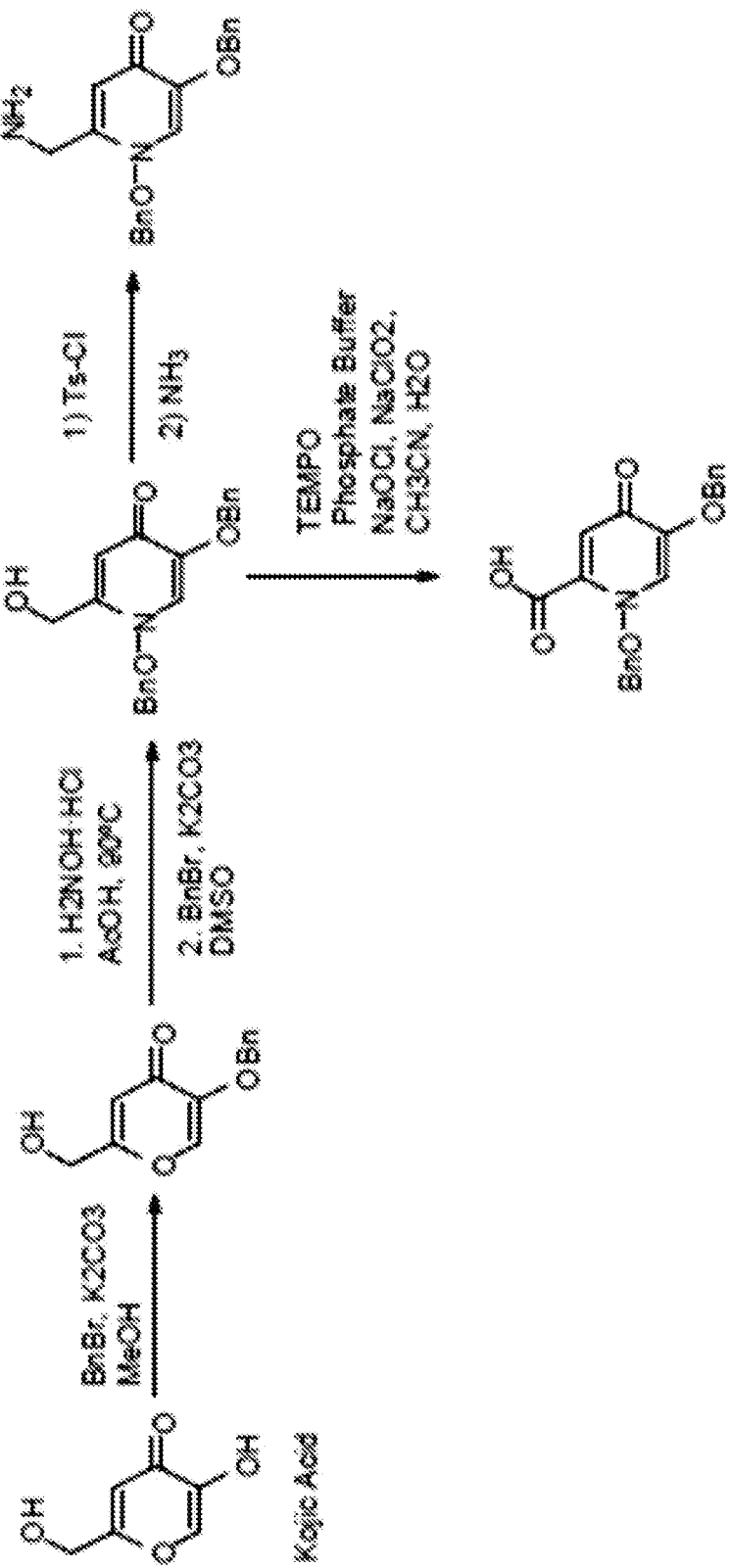
FIG. 2 is a synthetic scheme depicting pyridone based siderophore mimetics.

A representative synthetic scheme is shown in FIG. 1. C(3) siderophore linked pyrazolidinone agents were synthesized using rigid linkers and known active C(3) substituents as connections. The synthesis of the pyrazolidinone agents is convergent and can be achieved through a 1,3-dipolar cycloaddition or through an intramolecular Wadsworth-Horner-Emmons condensation. The latter method is most versatile and is exemplified with a C(3) carboxy group allowing the final compound to be synthesized efficiently with the longest linear sequence being nine steps (FIG. 1). Pyridone-based siderophore mimetics are readily synthesized from kojic acid as illustrated (FIG. 2) and both amine and a carboxy attachment points are known. This allows rapid exploration of SAR and chain length including, but not limited to, urea, carboxamide, and amino acid linkers. Other C(3) groups such as a sulfone or a sulfonamide can be synthesized using routes similar to those illustrated for the C(3) carboxy group.

Figure 4:
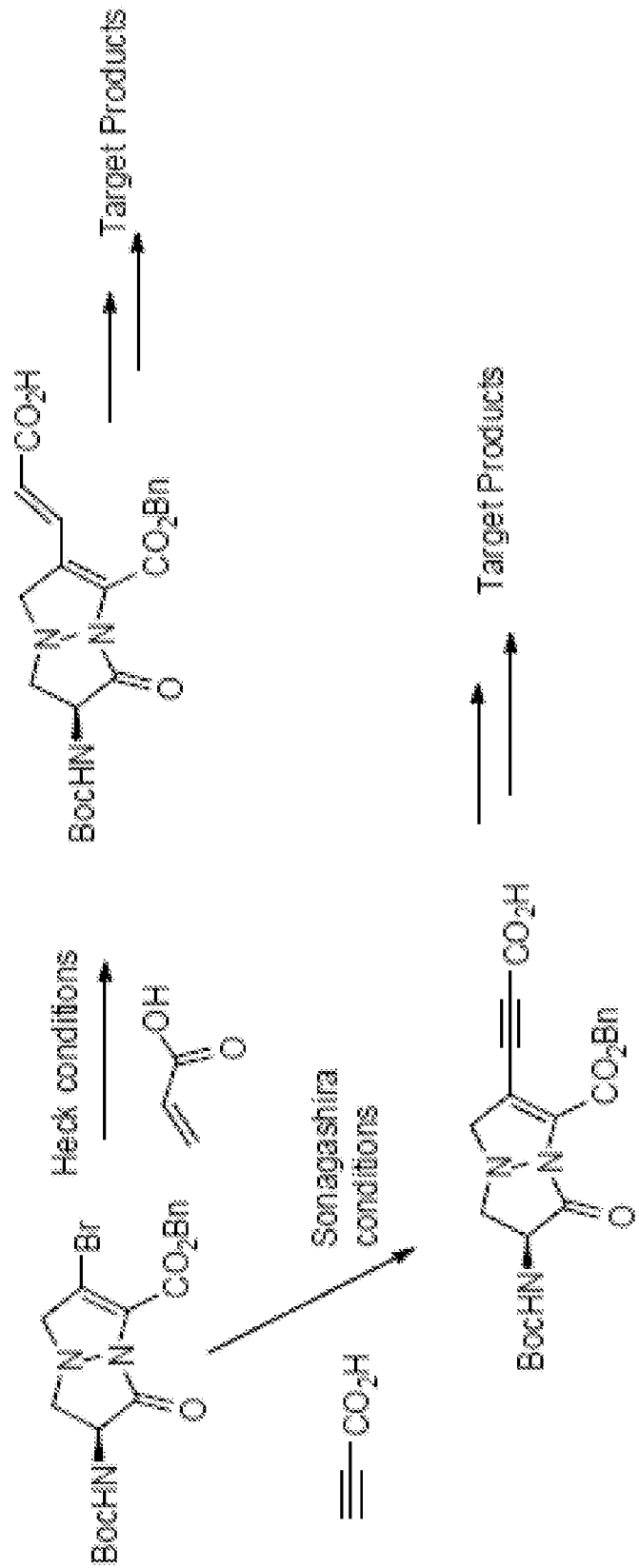
FIG. 4 is a synthetic scheme depicting synthesis of pyrazolidinone agents with extended C(3) attachment points.
Figure 5:
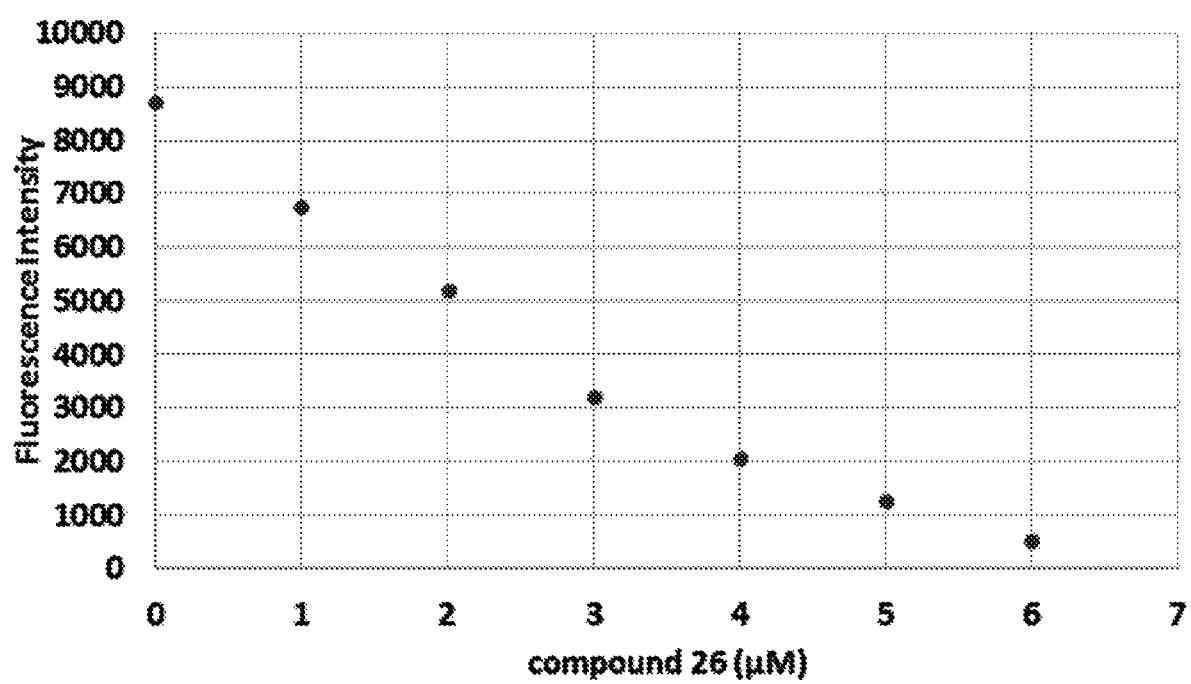
FIG. 5 is a graph showing compound 26 inhibiting *Pseudomonas aeruginosa* penicillin binding protein 3 (PBP3). $IC_{50}=2.5\pm0.5$ µM
Figure 6A:
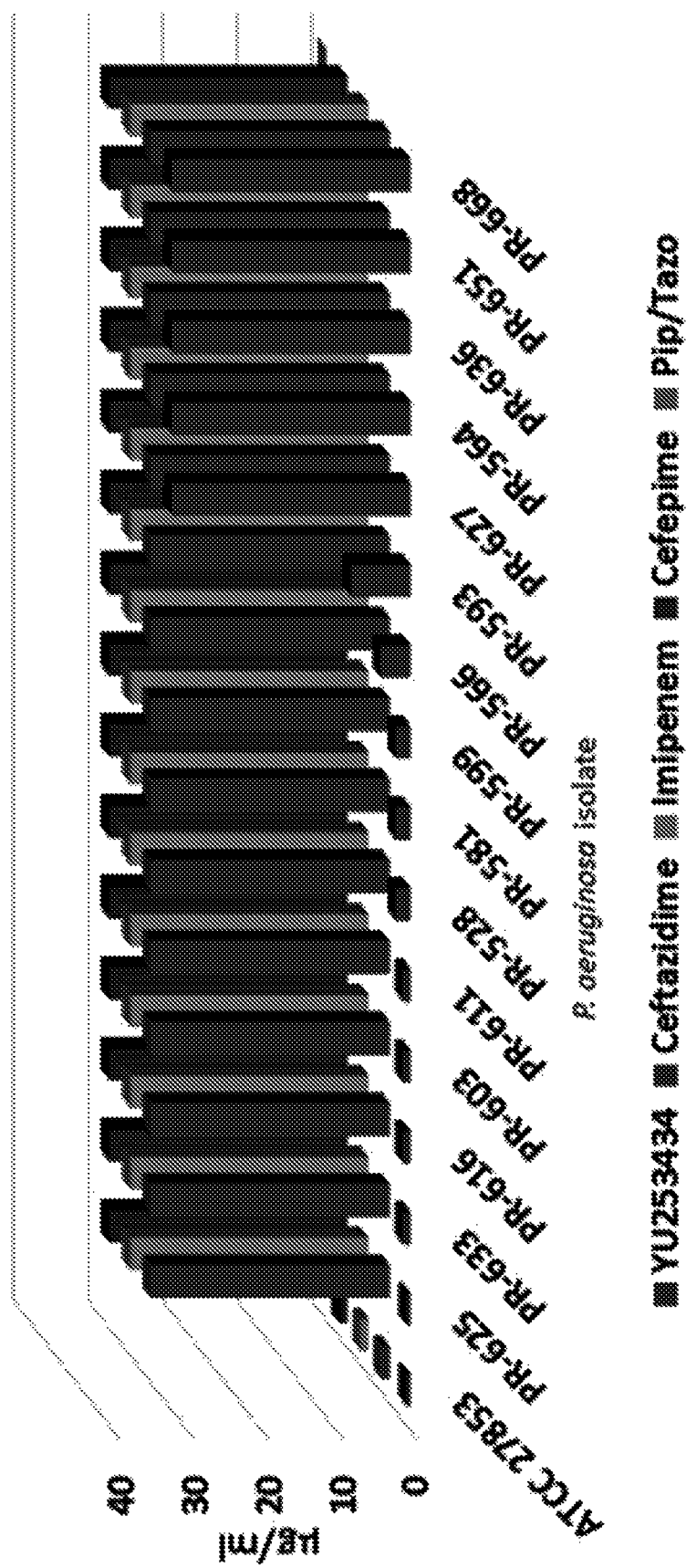
FIGS. 6A-6C are summaries of MIC values of compound 26 (YU253434) against *P. aeruginosa* (FIG. 6A), *E. coli* (FIG. 6B), and *K. pneumoniae* (FIG. 6C). From front row to back row: for FIG. 6A, YU253434, Ceftazidine, Imipenem, Cefepime, Pip/Tazo; for FIG. 6B, YU253434, Imipenem, Ceftazidine, Ampicillin; for FIG. 6C, YU253434, Imipenem, Ceftazidine, Ampicillin.
Figure 6B:
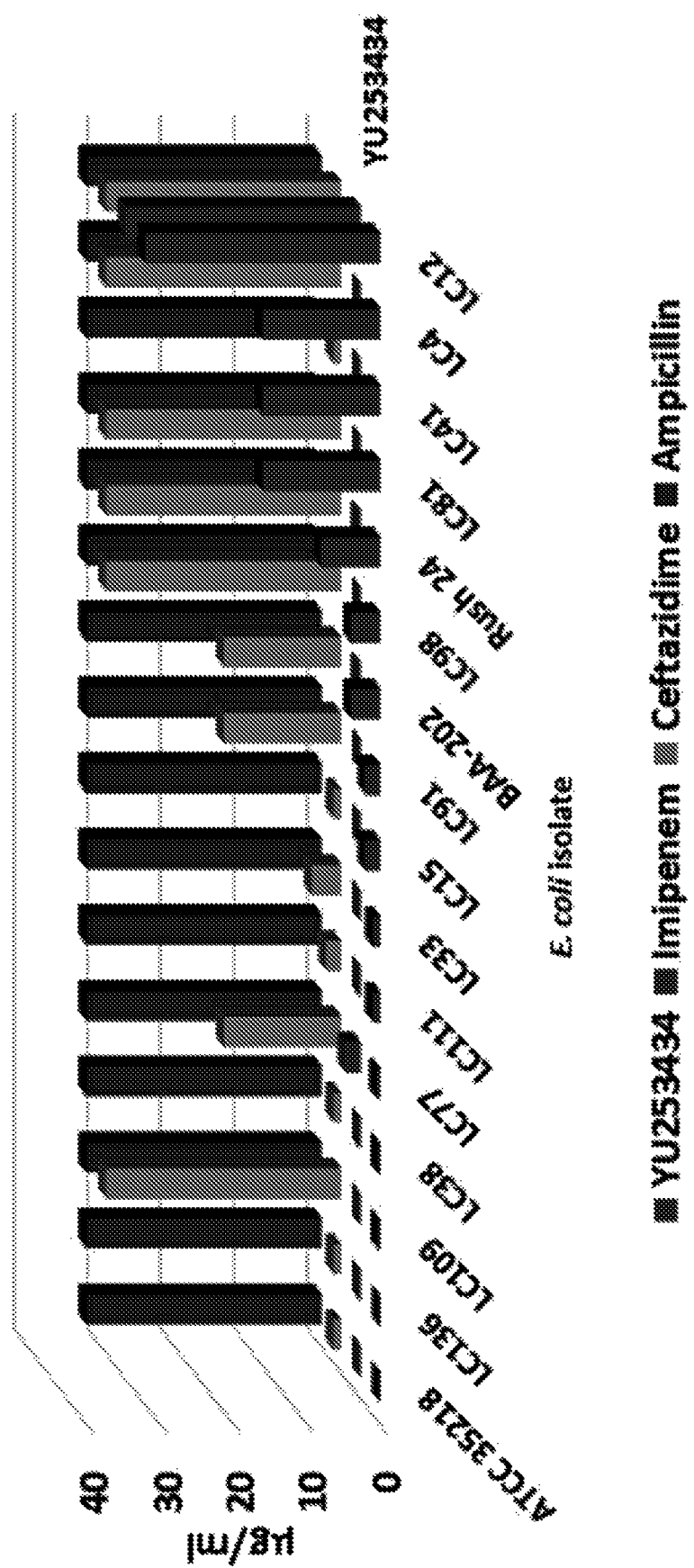
Figure 6C:
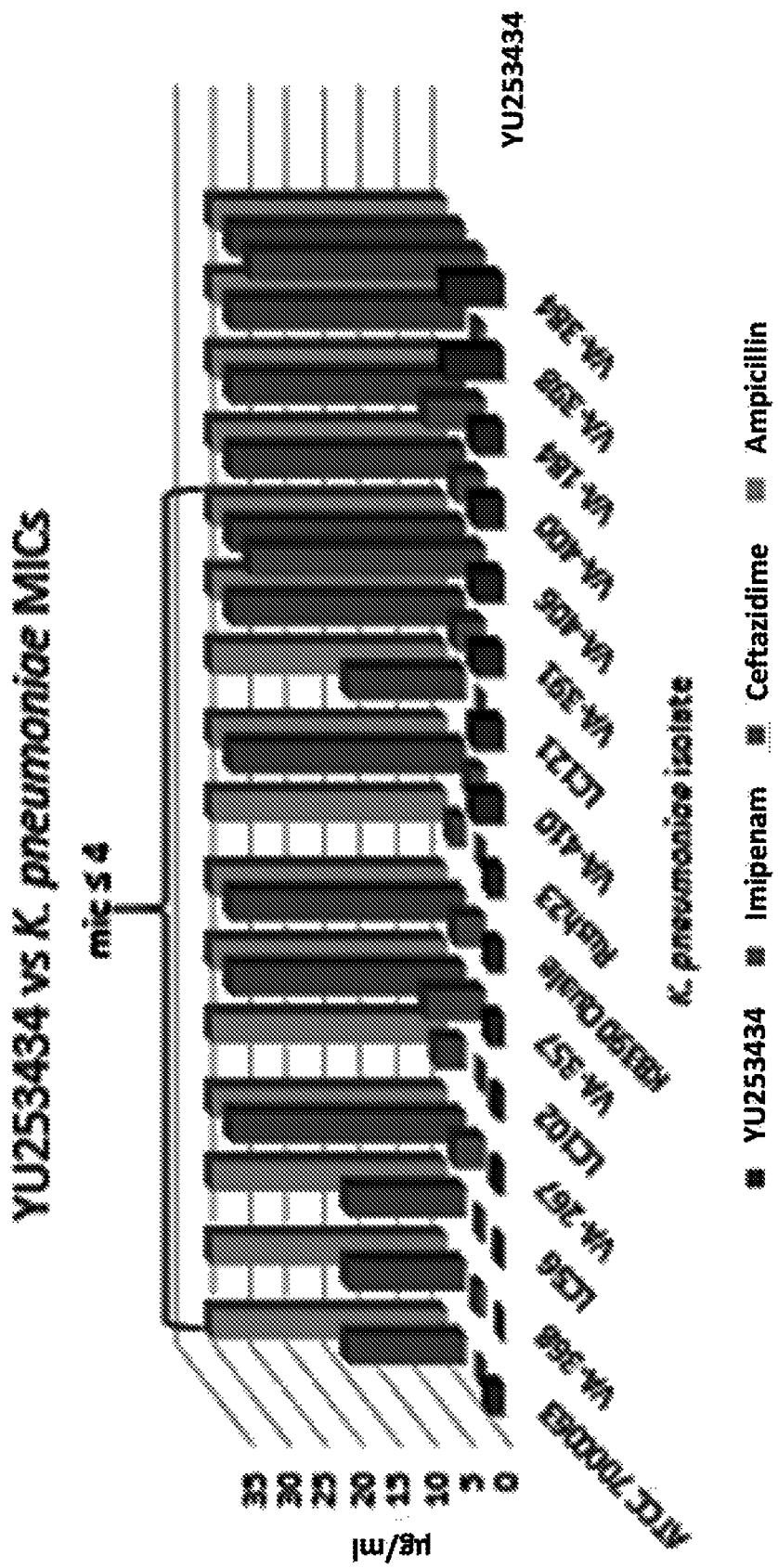
Figure 9:
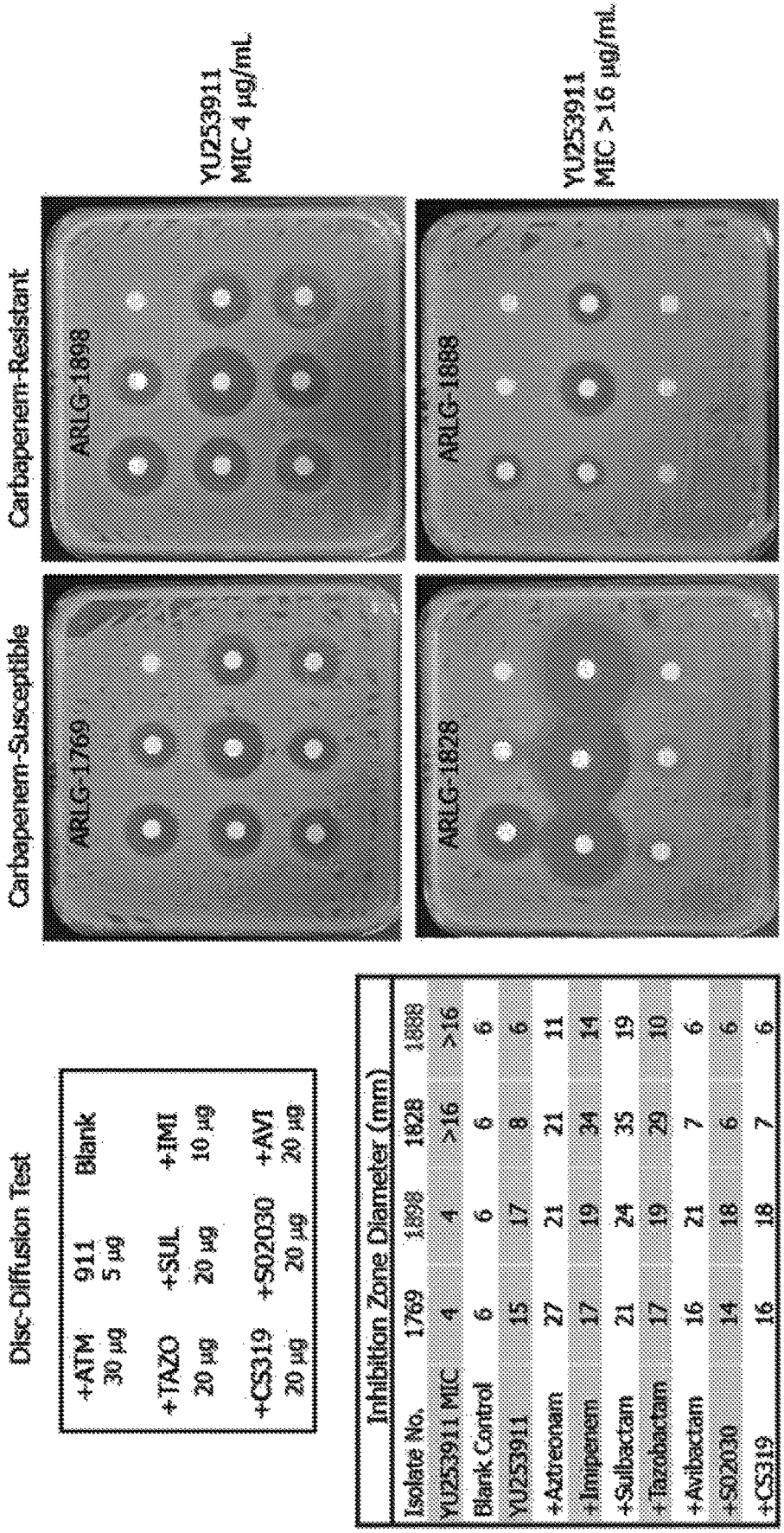
FIG. 9 is a disc diffusion test showing the efficacy of compound 42 YU253911 with partner agents such as sulbactam.

Synthesis of pyrazolidinone agents with extended C(3) attachment points applies Heck and Sonagashira reactions to the pyrazolidinone core to make novel target compounds, as depicted for the acrylate case (FIG. 4). The bromo intermediate serves as a branch point and provides access to the alkyne analogs through Sonagashira coupling. This allows for rapid exploration of extensions in the context of urea, amide, heteroaromatic and other linkers. Other C(3) groups such as a vinyl sulfone or a vinyl sulfonamide may be synthesized using routes similar to those illustrated for the C(3) acrylate.

Scheme 1 Synthesis of tert-butyl (S)-3-oxopyrazolidin-4-yl)carbamate 27

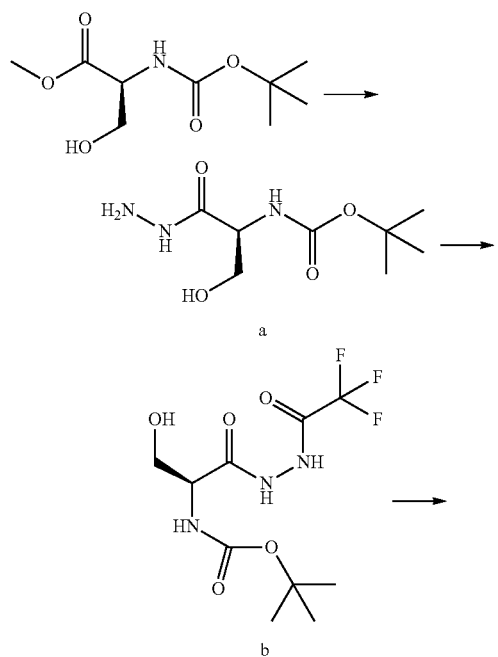

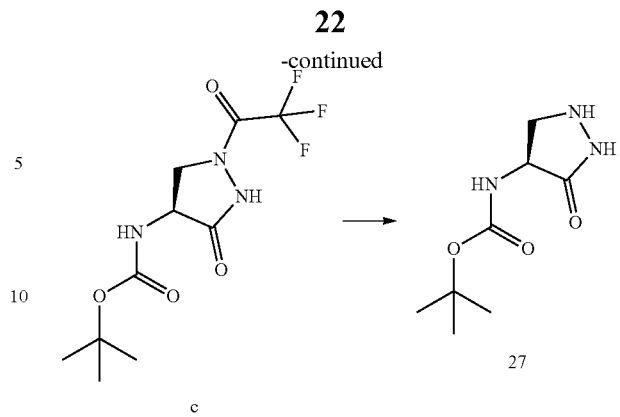

Synthesis of tert-butyl (S)-(1-hydrazineyl-3-hydroxy-1-oxopropan-2-yl)carbamate

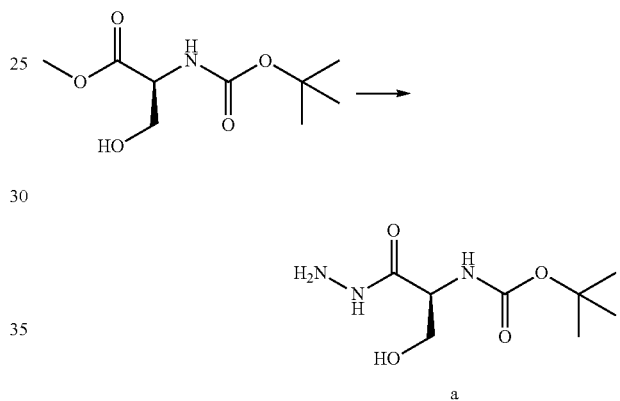

To L-Boc-Ser-OMe (25 g, 114 mmol) in methanol (100 mL) was added hydrazine hydrate (25 mL, 402 mmol). The solution was stirred at 50° C. overnight. The following day the solvent was removed under reduced pressure and the resulting solid dried under hi-vac to a constant weight to give tert-butyl (S)-(1-hydrazineyl-3-hydroxy-1-oxopropan-2-yl)carbamate (23.4 g, 93.7%). NMR DMSO 9.0 (s, 1H), 6.5 (d, 1H), 4.8 (s, 1H), 4.2 (s, 2H), 3.9 (m, 1H), 3.5 (s, 2H), 1.4 (s, 9H).

Synthesis of tert-butyl (S)-(3-hydroxy-1-oxo-1-(2-(2,2,2-trifluoroacetyl)hydrazineyl)propan-2-yl)carbamate

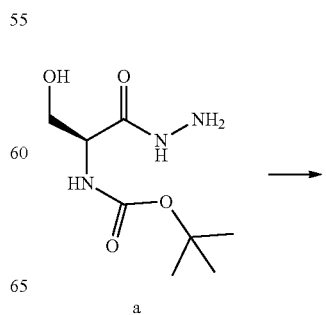

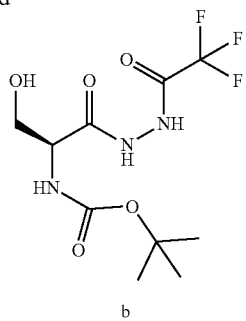

b tert-Butyl (S)-(1-hydrazineyl-3-hydroxy-1-oxopropan-2-yl)carbamate (25 g, 114 mmol) and S-ethyl trifluorothioacetate (22 mL, 171 mmol) were combined in ethanol (150 mL). The reaction was stirred at room temperature overnight under a stream of nitrogen. The reaction was concentrated further to a thick residue, which was crystallized from Et₂O/hexanes to give tert-butyl (S)-(3-hydroxy-1-oxo-1-(2-(2,2,2-trifluoroacetyl)hydrazineyl)propan-2-yl)carbamate (27.5 g, 76.4%). 1H-NMR DMSO 11.5 (s, 1H), 10.3 (s, 1H), 6.8 (d, 1H), 4.9 (s, 1H), 4.1 (m, 1H), 3.6 (d, 2H), 1.4 (s, 9H).

Synthesis of tert-butyl (S)-(3-oxo-1-(2,2,2-trifluoroacetyl)pyrazolidin-4-yl)carbamate

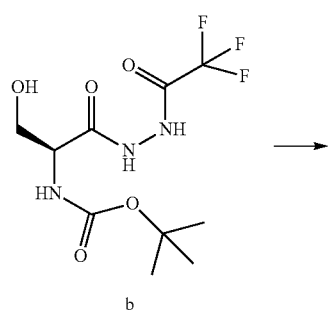

b

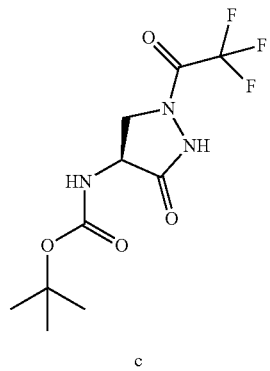

c tert-Butyl (S)-(3-hydroxy-1-oxo-1-(2-(2,2,2-trifluoroacetyl)hydrazineyl)propan-2-yl)carbamate (20.0 g, 63.4 mmol) and triphenylphosphine (20.0 g, 76.1 mmol) in THF (200 mL) were cooled in an ice bath. Diethyl azodicarboxylate (31.8 mL, 69.8 mmol, 40% solution in toluene) was added dropwise, keeping internal temperature below 10° C. The reaction was allowed to slowly come to room temperature and stirred overnight. The following day the solvent was removed under reduced pressure and the residue was taken up in 300 mL EtOAc. This was extracted with 3×100 mL saturated NaHCO₃ solution. The combined aqueous layers were washed with 3×100 mL EtOAc. The aqueous layer was carefully brought to pH 5.0 with 4 M HCl solution to give a white precipitate, which was filtered and air dried to give tert-butyl (S)-(3-oxo-1-(2,2,2-trifluoroacetyl)pyrazolidin-4-yl)carbamate (17.6 g, 93% yield). Mass spectrum M+H⁺(-tBu)=242.0.

Synthesis of tert-butyl (S)-(3-oxopyrazolidin-4-yl)carbamate 27

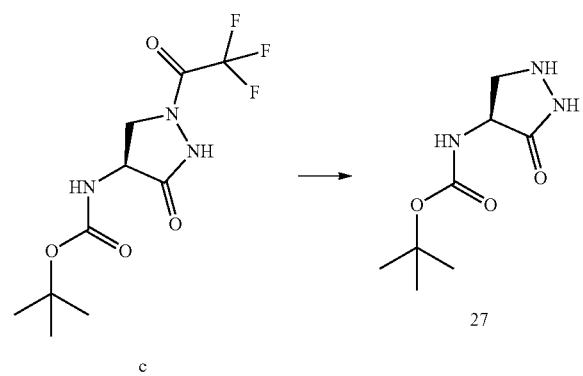 [SMILES: CC(C)(C)OC(=O)N[C@H]1CN(C(=O)C(F)(F)F)NC1=O ; CC(C)(C)OC(=O)N[C@H]1CNNC1=O]

c tert-butyl (S)-(3-oxo-1-(2,2,2-trifluoroacetyl)pyrazolidin-4-yl)carbamate (25.7 g, 86.6 mmol) was suspended in 50 mL H₂O and NaOH solution (124 mL, 1 M solution) was added. The reaction was stirred at room temperature for 5 h, at which point all material was in solution. The reaction was neutralized to between pH 6-7 using 4 M HCl solution. Solid began to precipitate and the solution was cooled in an ice bath to facilitate precipitation. The solid was filtered, washed with cold water, and air dried to give tert-butyl (S)-(3-oxopyrazolidin-4-yl)carbamate (7.3 g, 41.7% yield). Mass spectrum M+H⁺=202.1.

Synthesis of allyl 2-(diethoxyphosphoryl)acrylate 28

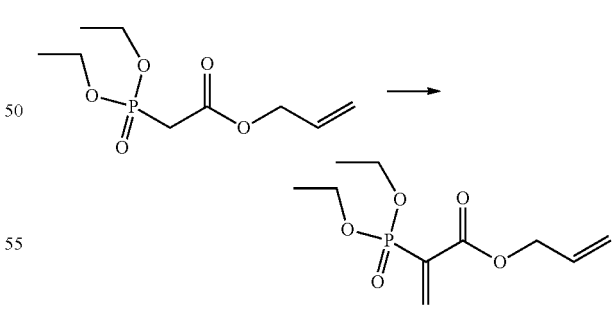

A solution of paraformaldehyde (2.24 g, 74.5 mmol) and piperidine (184 μL, 1.86 mmol) in ethanol (50 mL) was heated at reflux for 1 h. To this was added allyl 2-(diethoxyphosphoryl)acetate (11.0 g, 46.6 mmol) and the solution was refluxed for 72 hours, adding additional piperidine (184 μL, 1.86 mmol) and paraformaldehyde (250 mg, 8.3 mmol) after 24 and 48 hours. The solvent was removed under reduced pressure and the reaction was taken up in toluene (60 mL). To this was added p-toluenesulfonic acid monohydrate (140 mg, 0.81 mmol). The reaction was distilled to remove ethanol and toluene. Kugelrohr distillation of the remaining material provided allyl 2-(diethoxyphosphoryl)acrylate (7.37 g, 64% yield), which was stored as a 0.5 M solution in benzene at 0° C. NMR CDCl3 7.02 (d, 1H), 6.77 (d, 1H), 5.95 (m, 1H), 5.40 (d, 1H), 5.27 (d, 1H), 4.72 (m, 2H) 4.17 (q, 4H), 1.34 (t, 6H).

Synthesis of allyl 3-((S)-4-((tert-butoxycarbonyl)amino)-3-oxopyrazolidin-1-yl)-2-(diethoxyphosphoryl)propanoate 29

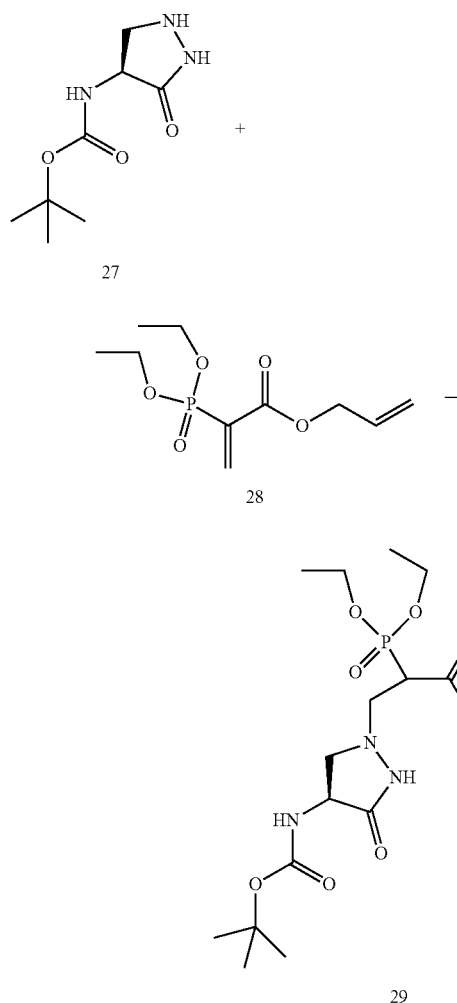

To a suspension of tert-butyl (S)-(3-oxopyrazolidin-4-yl) carbamate (5.0 g, 24.8 mmol) in DCM (40 mL) was added allyl 2-(diethoxyphosphoryl)acrylate (7.40 g, 29.8 mmol, 0.5 M solution in benzene). The reaction was stirred for 1 h at room temperature. The reaction solution was directly injected onto a silica gel column equilibrated with DCM. The column was run at 0-10% MeOH/DCM to give allyl 3-((S)-4-((tert-butoxycarbonyl)amino)-3-oxopyrazolidin-1-yl)-2-(diethoxyphosphoryl)propanoate (11.0 g, 98% yield). Mass spectrum M+H$^+$=450.2.

Synthesis of 2-allyl 3-(tert-butyl) (S)-6-((tert-butoxycarbonyl)amino)-5-oxo-6,7-dihydro-1H,5H-pyrazolo[1,2-a]pyrazole-2,3-dicarboxylate 30

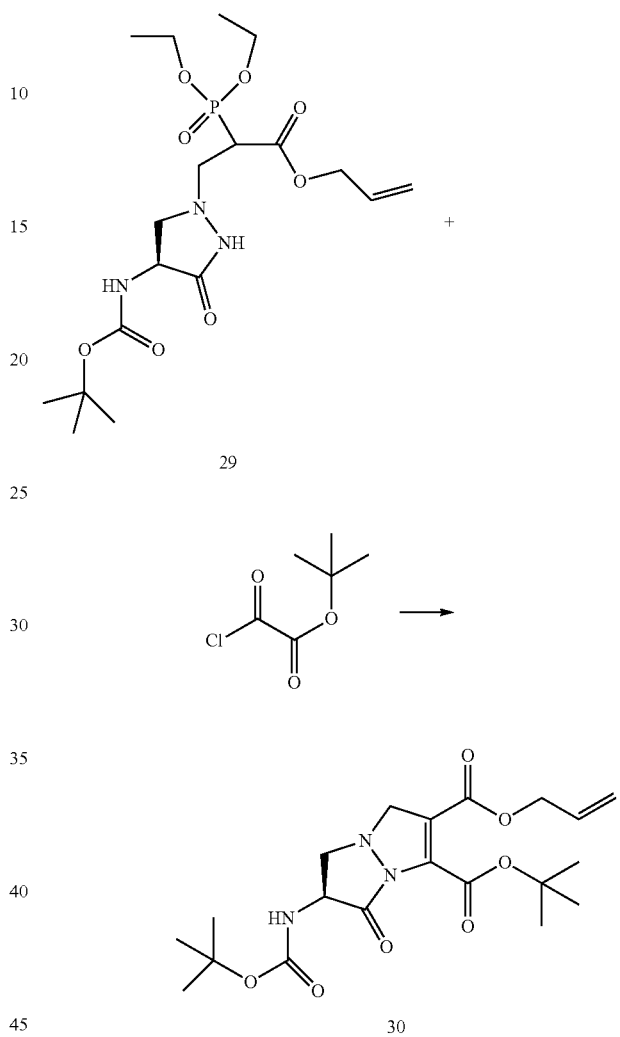

Allyl 3-((S)-4-((tert-butoxycarbonyl)amino)-3-oxopyrazolidin-1-yl)-2-(diethoxyphosphoryl)propanoate (4.0 g, 8.94 mmol) was dissolved in anhydrous DCM (55 mL) and cooled to 0° C. A solution of tert-butyl 2-chloro-2-oxoacetate (1.91 g, 11.6 mmol) in anhydrous DCM (5 mL) was added dropwise. After 5 minutes, Hunig's base (4.22 mL, 24.2 mmol) was added dropwise. The reaction was slowly warmed to room temperature. After 2 h, additional tert-butyl 2-chloro-2-oxoacetate (250 mg, 1.5 mmol) was added as a solution in DCM (0.5 mL). The reaction was left to stir at room temperature overnight. The following day the reaction was diluted with DCM (100 mL) and the reaction was washed with 1 M H$_2$SO$_4$ (75 mL) solution, water (75 mL) and brine (50 mL). The organic layer was dried over MgSO$_4$, filtered, and concentrated under reduced pressure to give crude 2-allyl 3-(tert-butyl) (S)-6-((tert-butoxycarbonyl)amino)-5-oxo-6,7-dihydro-1H,5H-pyrazolo[1,2-a]pyrazole-2,3-dicarboxylate, which was used as is for the subsequent reaction. Mass spectrum M+H$^+$=424.1.

Synthesis of (S)-3-(tert-butoxycarbonyl)-6-((tert-butoxycarbonyl)amino)-5-oxo-6,7-dihydro-1H,5H-pyrazolo[1,2-a]pyrazole-2-carboxylic acid 1

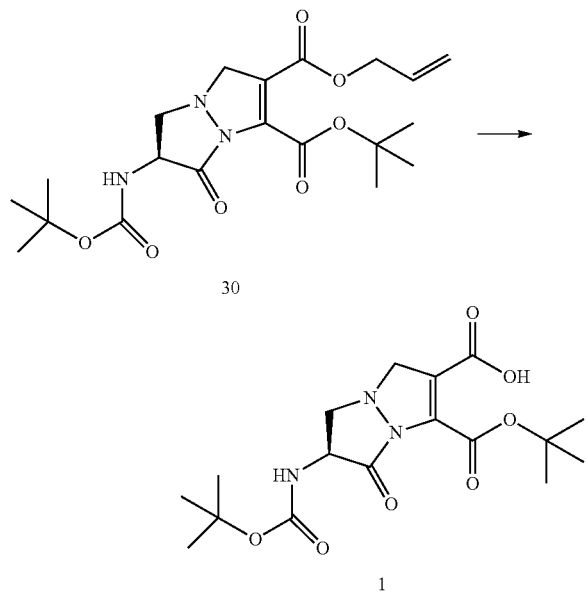

2-allyl 3-(tert-butyl) (S)-6-((tert-butoxycarbonyl)amino)-5-oxo-6,7-dihydro-1H,5H-pyrazolo[1,2-a]pyrazole-2,3-dicarboxylate (3.79 g, 8.95 mmol) was dissolved in ACN (100 mL), flushed with $N_2$, and cooled to 0° C. Triethylsilane (1.72 mL, 10.7 mmol) was added dropwise, followed by $Pd(PPh_3)_4$ (827 mg, 0.7 mmol). The reaction was stirred at 0° C. for 30 minutes, then warmed to room temperature and stirred an additional 4 hours. The reaction was quenched by addition of 0.1 M HCl solution (10 mL) and stirred for 30 minutes. The reaction was diluted with EtOAc (250 mL) and the aqueous layer was discarded. The organics were extracted with 50% saturated $NaHCO_3$ solution (2×100 mL). The combined aqueous layers were neutralized with 1 M $H_2SO_4$ and extracted with EtOAc (3×100 mL). The combined organics were washed with brine, dried over $MgSO_4$, and concentrated under reduced pressure to give (S)-3-(tert-butoxycarbonyl)-6-((tert-butoxycarbonyl)amino)-5-oxo-6,7-dihydro-1H,5H-pyrazolo[1,2-a]pyrazole-2-carboxylic acid (2.22 g, 65% yield). Mass spectrum M+H$^+$=384.2.

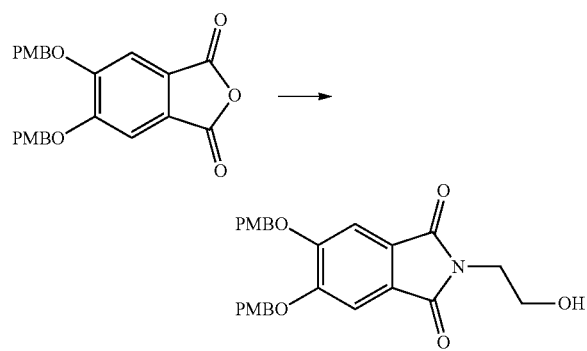

A solution of 750 mg (1.78 mmol) 5,6-bis((4-methoxybenzyl)oxy)isobenzofuran-1,3-dione and 218 mg (3.57 mmol) of ethanolamine in 10 mL EtOH was heated at 80° C. for 4 h. As the reaction is allowed to come to room temperature a white solid crashed out. The mixture was cooled in an ice bath to facilitate precipitation, then filtered and washed with cold ethanol to give 692 mg (84% yield) of 2-(2-hydroxyethyl)-5,6-bis((4-methoxybenzyl)oxy)isoindoline-1,3-dione. Mass spectrum M+H$^+$=464.0.

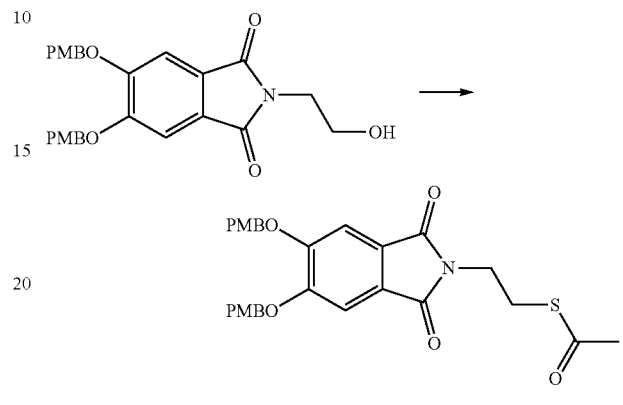

To an ice-cooled solution of 781 mg (2.98 mmol) triphenylphosphine in 10 mL THF was added 1.17 ml (2.98 mmol) 40% diethyl azodicarboxylate solution. After stirring for 10 minutes, a solution of 627 mg (1.35 mmol) 2-(2-hydroxyethyl)-5,6-bis((4-methoxybenzyl)oxy)isoindoline-1,3-dione in 3 mL THF was added dropwise. After stirring for 10 minutes, a solution of 211 μL (2.98 mmol) thioacetic acid in 1 mL THF was added dropwise. The solution is stirred for 1.5 h at 0° C. The solvent was removed under reduced pressure and the residue was purified via flash chromatography (0-100% EtOAc/hexanes). The impure product was subjected to a second purification via flash chromatography (0-30% EtOAc/DCM) to give 637 mg (90% yield) S-(2-(5,6-bis((4-methoxybenzyl)oxy)-1,3-dioxoisoindolin-2-yl)ethyl) ethanethioate. Mass spectrum M+H$^+$=522.0.

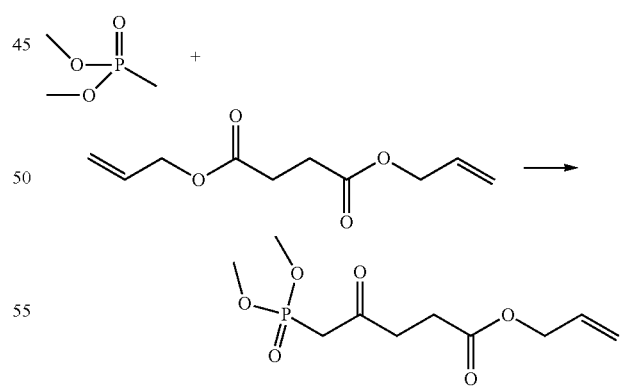

A solution of 2.33 g (18.8 mmol) dimethyl methylphosphonate in 20 mL THF was cooled to −78° C. and 14.7 mL (23.5 mmol, 1.6 M solution) n-BuLi solution was added dropwise. The reaction was stirred 15 minutes then 3.1 g (15.6 mmol) diallyl succinate was quickly added. The reaction was stirred 15 minutes at −78° C., then quenched with 5 mL sat. $NH_4Cl$ solution and brought to room temperature. The reaction was poured into 75 mL sat. $NH_4Cl$ solution and extracted ×3 50 mL EtOAc. The combined organics were washed with brine, dried over MgSO₄, and concentrated under reduced pressure to give 7.45 g of 48% pure allyl 5-(dimethoxyphosphoryl)-4-oxopentanoate (86% yield) as a mixture with unreacted diallyl succinate. Mass spectrum M+H⁺=323.1.

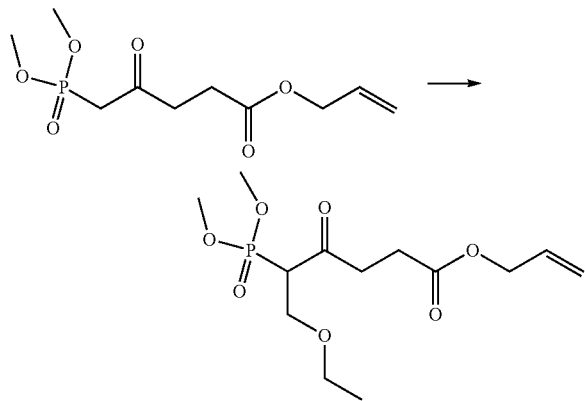

A solution of 650 mg (21.7 mmol) paraformaldehyde and 46 mg piperidine (0.54 mmol) were refluxed in 150 mL EtOH for 1 h. A solution of 7.45 g (13.5 mmol) allyl 5-(dimethoxyphosphoryl)-4-oxopentanoate in 20 mL EtOH was added via syringe pump over 90 minutes. The reaction was stirred for an additional 1 h at reflux. The reaction was concentrated under reduced pressure onto silica gel, then purified via flash chromatography (0-10% MeOH/DCM) to give 3.65 g (84% yield) allyl 5-(dimethoxyphosphoryl)-6-ethoxy-4-oxohexanoate. Mass spectrum M+H⁺=323.1.

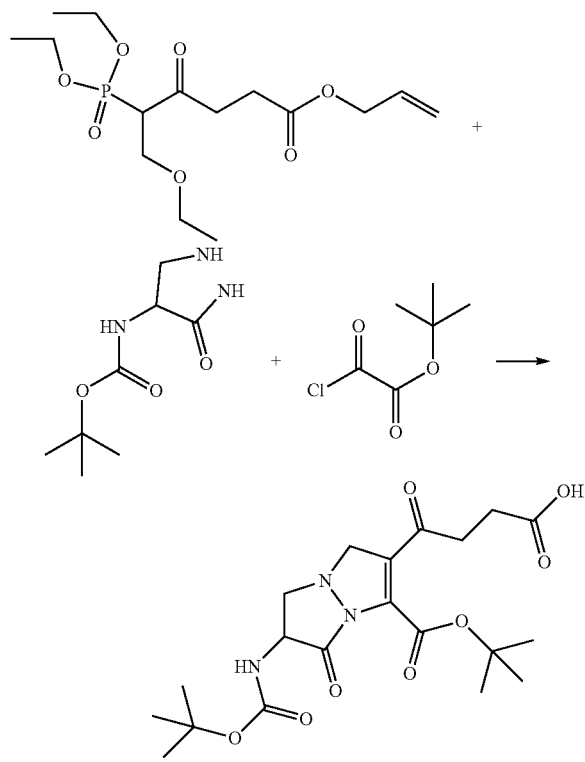

599 mg (1.86 mmol) allyl 5-(diethoxyphosphoryl)-6-ethoxy-4-oxohexanoate and 343 mg (1.70 mmol) tert-butyl (3-oxopyrazolidin-4-yl)carbamate were combined in 10 mL EtOH and heated at 50° C. for 1 h. The reaction was concentrated under reduced pressure, chased with toluene, and taken up in 18 mL DCM and cooled to 0° C. To this was added 309 mg (1.88 mmol) tert-butyl 2-chloro-2-oxoacetate. After 10 minutes, 0.62 mL (3.58 mmol) Hunig's base was added. The reaction was warmed to room temperature and stirred for 2 h. The reaction was diluted with 50 mL DCM and the reaction wash washed with 25 mL 1M H₂SO₄ solution, 25 mL water and 10 mL brine. The organic layer was dried over MgSO₄, filtered, and concentrated under reduced pressure to give the crude product. This was taken up 10 mL ACN and cooled to 0° C. To this was added 0.33 mL triethylsilane (2.04 mmol) followed by 157 mg (0.14 mmol) Pd(PPh₃)₄. This was stirred at 0° C. for 30 min, then 1 hour at room temperature. The reaction was quenched by addition of 10 mL 0.1 M HCl solution and stirred for 30 minutes. This was then diluted with 60 mL EtOAc and the aqueous layer was discarded. The organics are extracted with 2×25 mL 50% saturated NaHCO₃ solution. The combined aqueous layers were neutralized with 1 M H₂SO₄ and extracted with 3×25 mL EtOAc. The combined organics are washed with brine, dried over MgSO₄, and concentrated under reduced pressure to give 250 mg (33% yield) 4-(3-(tert-butoxycarbonyl)-6-((tert-butoxycarbonyl)amino)-5-oxo-6,7-dihydro-1H,5H-pyrazolo[1,2-a]pyrazol-2-yl)-4-oxobutanoic acid. Mass spectrum M+H⁺=440.2.

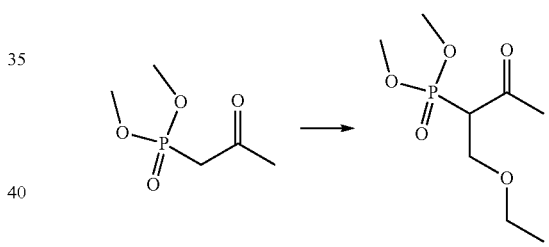

A solution of 1.74 mg (57.8 mmol) paraformaldehyde and 123 mg piperidine (1.44 mmol) were refluxed in 150 mL EtOH for 1 h. A solution of 6.0 g (36.1 mmol) dimethyl (2-oxopropyl)phosphonate in 20 mL EtOH was added via syringe pump over 90 minutes. The reaction was stirred for an additional 1 h at reflux. The reaction was concentrated under reduced pressure onto silica gel, then purified via flash chromatography (0-20% MeOH/DCM) to give 5.08 g (63% yield) dimethyl (1-ethoxy-3-oxobutan-2-yl)phosphonate. Mass spectrum M+H⁺=225.1.

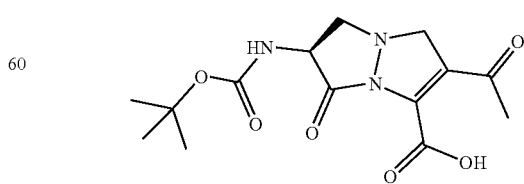

Made analogous to above M+382.1.

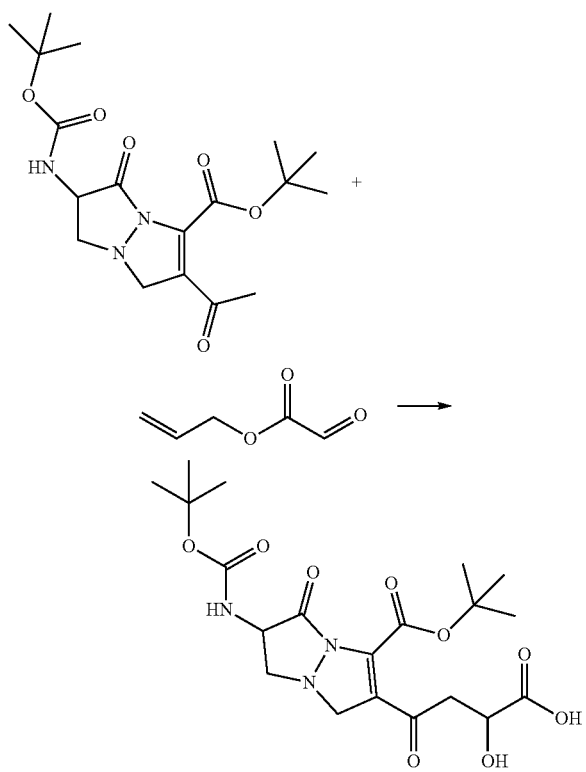

To 9 mL THF cooled to −78° C. was added 3.13 mL LiHMDS (6.26 mmol, 1 M in THF). A solution of 545 mg (2.85 mmoltert-butyl 2-acetyl-6-((tert-butoxycarbonyl)amino)-5-oxo-6,7-dihydro-1H,5H-pyrazolo[1,2-a]pyrazole-3-carboxylate in 3 mL THF was added dropwise to the LiHMDS solution. This was stirred at −78° C. for 10 min, at which point 810 mg (3.42 mmol) allyl 2-oxoacetate was added dropwise. The reaction was stirred at −78 C for 15 min, then quenched with THF/AcOH. The reaction was diluted with EtOAc, washed with 1 M $H_2SO_4$ solution, brine, dried over $MgSO_4$, and concentrated. The material was taken up 25 mL ACN and cooled to 0° C. To this was added 0.30 mL triethylsilane (1.89 mmol) followed by 145 mg (0.13 mmol) Pd(PPh$_3$)$_4$. This was stirred at 0° C. for 30 min, then 1 hour at room temperature. The reaction was quenched by addition of 10 mL 0.1 M HCl solution and stirred for 30 minutes. This was then diluted with 60 mL EtOAc and the aqueous layer was discarded. The organics are extracted with 2×25 mL 50% saturated $NaHCO_3$ solution. The combined aqueous layers were neutralized with 1 M $H_2SO_4$ and extracted with 3×25 mL EtOAc. The combined organics were washed with brine, dried over $MgSO_4$, and concentrated under reduced pressure to give 254 mg (36% yield) 4-(3-(tert-butoxycarbonyl)-6-((tert-butoxycarbonyl)amino)-5-oxo-6,7-dihydro-1H,5H-pyrazolo[1,2-a]pyrazol-2-yl)-2-hydroxy-4-oxobutanoic acid. Mass spectrum M+H$^+$=456.1.

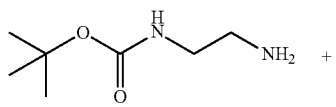

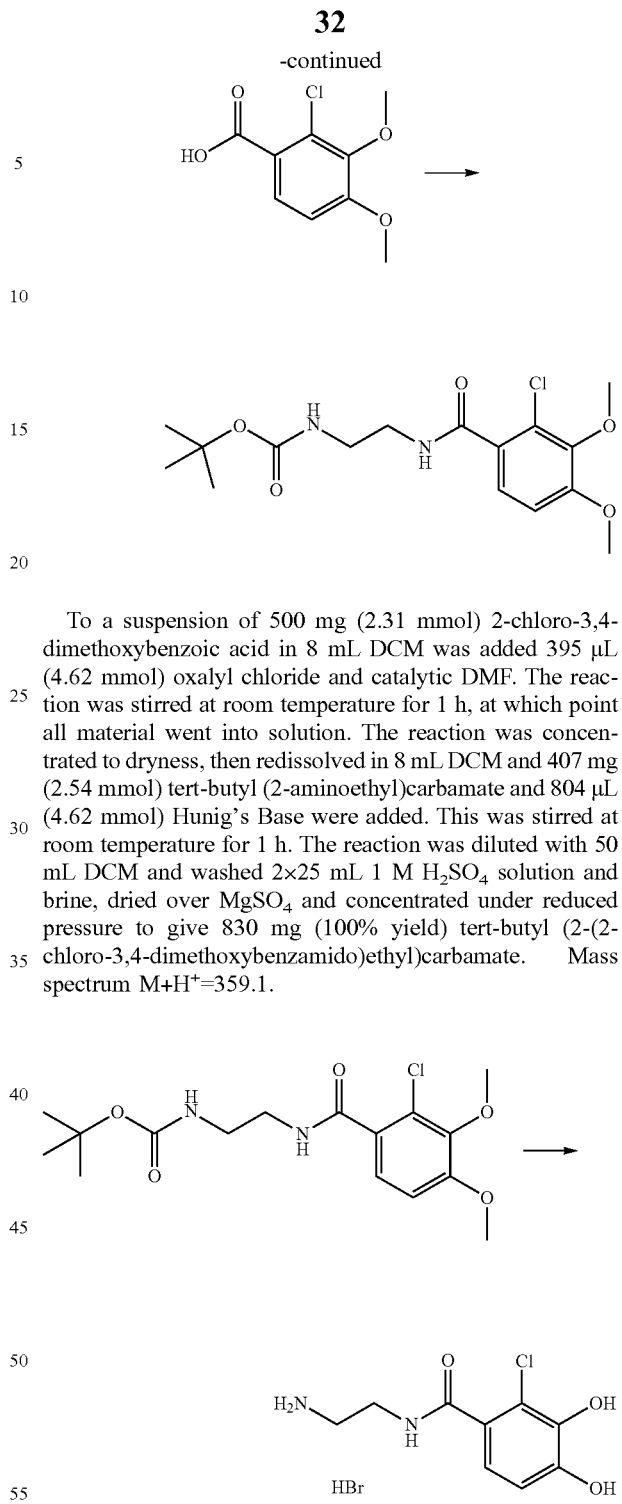

To a suspension of 500 mg (2.31 mmol) 2-chloro-3,4-dimethoxybenzoic acid in 8 mL DCM was added 395 µL (4.62 mmol) oxalyl chloride and catalytic DMF. The reaction was stirred at room temperature for 1 h, at which point all material went into solution. The reaction was concentrated to dryness, then redissolved in 8 mL DCM and 407 mg (2.54 mmol) tert-butyl (2-aminoethyl)carbamate and 804 µL (4.62 mmol) Hunig's Base were added. This was stirred at room temperature for 1 h. The reaction was diluted with 50 mL DCM and washed 2×25 mL 1 M $H_2SO_4$ solution and brine, dried over $MgSO_4$ and concentrated under reduced pressure to give 830 mg (100% yield) tert-butyl (2-(2-chloro-3,4-dimethoxybenzamido)ethyl)carbamate. Mass spectrum M+H$^+$=359.1.

To a solution of 440 mg (1.23 mmol) starting material in 10 mL DCM at −78° C. was added 3.68 mL BBr$_3$ solution (3.68 mmol, 1 M solution) dropwise. The mixture was stirred at −78° C. for 1 h, then warmed to room temperature and stirred for 1 h. The reaction was slowly quenched with MeOH at 0° C. The resulting solution was concentrated. Ether was added to the residue and the solution left to stand for 48 h, at which point the resulting solids were filtered to give 337 mg (88% yield) of the desired product as the HBr salt. Mass spectrum M+H$^+$=231.0.

Synthesis of (S,Z)-6-(2-(2-aminothiazol-4-yl)-2-(((2-carboxypropan-2-yl)oxy)imino)acetamido)-5-oxo-2-(phenethylcarbamoyl)-6,7-dihydro-1H,5H-pyrazolo[1,2-a]pyrazole-3-carboxylic acid 6

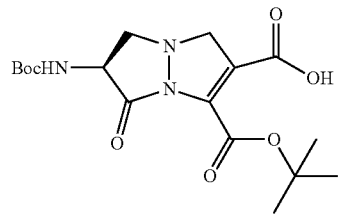

1

+

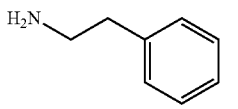

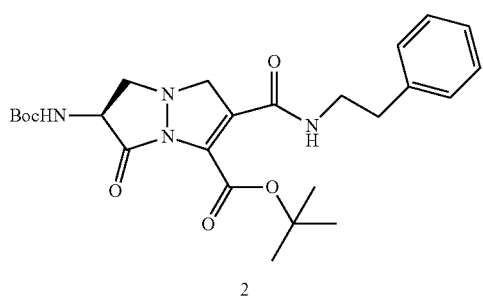

2

Synthesis of intermediate tert-butyl (S)-6-((tert-butoxycarbonyl)amino)-5-oxo-2-(phenethylcarbamoyl)-6,7-dihydro-1H,5H-pyrazolo[1,2-a]pyrazole-3-carboxylate 2

(S)-3-(tert-butoxycarbonyl)-6-((tert-butoxycarbonyl)amino)-5-oxo-6,7-dihydro-1H,5H-pyrazolo[1,2-a]pyrazole-2-carboxylic acid 1 (109 mg, 0.28 mmol) in acetonitrile (2.5 mL) was treated with DCC (70 mg, 1.2 equiv) and hydroxy azabenztriazole (HOAT, 46 mg, 1.2 equiv). The reaction was stirred one hour at room temperature and phenethyl amine (39 uL, 1.1 equiv.) was added. The reaction was stirred for 2 hours and diluted with ethyl acetate, washed with 0.1 N sulfuric acid, water, saturated sodium bicarbonate and then brine. After drying over magnesium sulfate the solvent was removed under reduced pressure to give 2 as a yellow glass 153 mg. Mass Spectrum M+H⁺(-tBu) 431.1.

Synthesis of intermediate (S)-6-amino-5-oxo-2-(phenethylcarbamoyl)-6,7-dihydro-1H,5H-pyrazolo[1,2-a]pyrazole-3-carboxylic acid 3

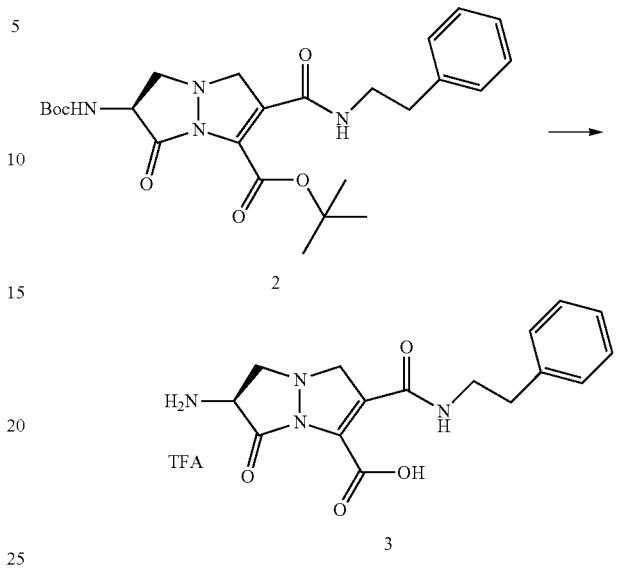

tert-Butyl (S)-6-((tert-butoxycarbonyl)amino)-5-oxo-2-(phenethylcarbamoyl)-6,7-dihydro-1H,5H-pyrazolo[1,2-a]pyrazole-3-carboxylate 2 (190 mg, 0.39 mmol) in dry DCM 6 mL and triethylsilane (0.187 mL, 3 equiv.) was cooled in an ice bath and TFA (3.0 mL, 100 equiv.) was added. The reaction was warmed to room temperature after 1 hour and stirred 2.5 hours more. Toluene (20 mL) was added and the solvent was removed under reduced pressure to give 3 as a yellow solid presumed to be the TFA salt that was used without purification. Mass spectrum M+H⁺331.1.

Synthesis of intermediate (S,Z)-6-(2-(((1-(tert-butoxy)-2-methyl-1-oxopropan-2-yl)oxy)imino)-2-(2-(tritylamino)thiazol-4-yl)acetamido)-5-oxo-2-(phenethylcarbamoyl)-6,7-dihydro-1H,5H-pyrazolo[1,2-a]pyrazole-3-carboxylic acid 5

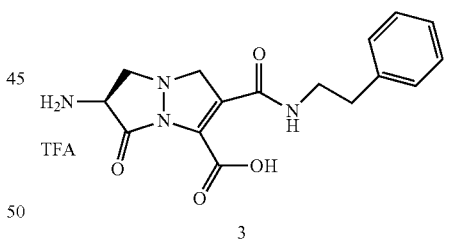

3

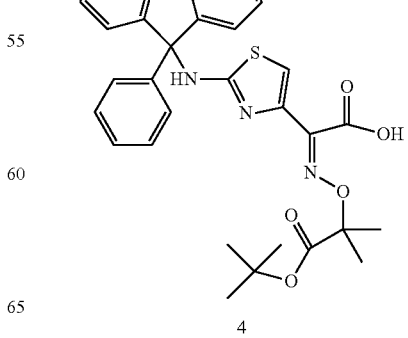

4

-continued

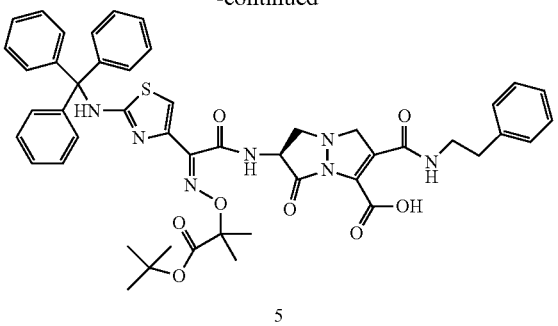

5

The commercial carboxylic acid 4 (361 mg, 0.63 mmol) in DCM (3.5 mL) with a catalytic amount of DMF was cooled in an ice bath and treated with oxalyl chloride (0.054 mL, 1.1 equiv.) for 1 hour. The solvent was blown away under a stream of nitrogen and the residue was put on a high vacuum for 30 minutes. The resulting intermediate acid chloride was dissolved in DCM (3.5 mL) and added to a solution of 3 (0.58 mmol) in DCM (3.5 mL) cooled in an ice bath. After the addition Hunig's base the reaction was stirred for 3 hours. Ethyl acetate was added and the reaction was washed with 0.1N sulfuric acid, water and then brine. After drying over magnesium sulfate the solvent was removed under reduced pressure to give 5 as a yellow foam. That was directly deprotected to give the final compound.

Synthesis of (S,Z)-6-(2-(2-aminothiazol-4-yl)-2-(((2-carboxypropan-2-yl)oxy)imino)acetamido)-5-oxo-2-(phenethylcarbamoyl)-6,7-dihydro-1H,5H-pyrazolo[1,2-a]pyrazole-3-carboxylic acid 6

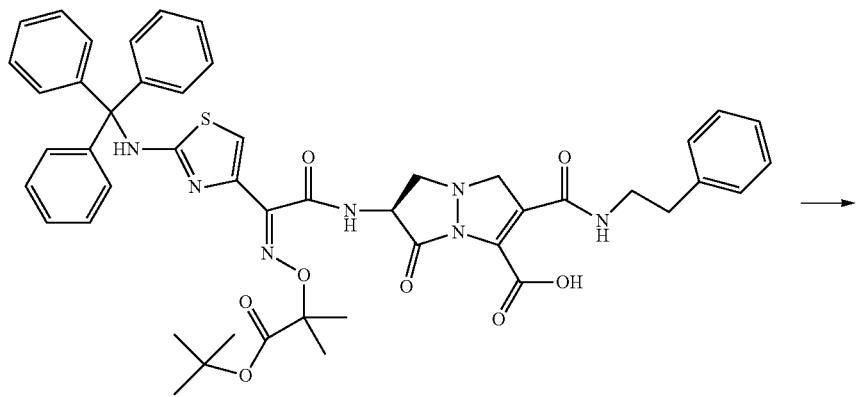

5

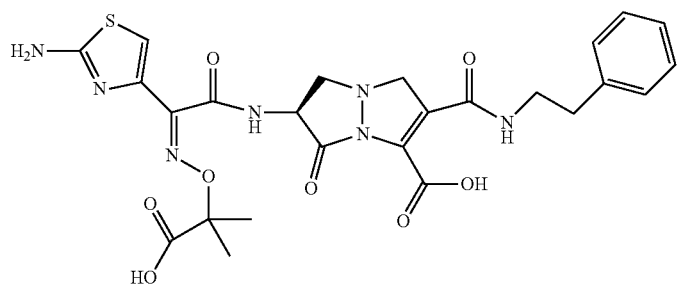

6

Starting material (S,Z)-6-(2-(((1-(tert-butoxy)-2-methyl-1-oxopropan-2-yl)oxy)imino)-2-(2-(tritylamino)thiazol-4-yl)acetamido)-5-oxo-2-(phenethylcarbamoyl)-6,7-dihydro-1H,5H-pyrazolo[1,2-a]pyrazole-3-carboxylic acid 5 (250 mg, 0.28 mmol) in dry DCM (4.4 mL) was treated with triethylsilane (135 uL, 3 equiv) and cooled in an ice bath. To this was added trifluoroacetic acid (2.2 mL, 100 equiv), and the reaction was warmed to room temperature. After 1.5 hours toluene (20 mL) was added and the reaction was evaporated to dryness and triturated with hexanes to remove trityl byproducts. The remaining yellow solid was chromatographed reverse phase C18 MPLC eluting with 0 to 60% acetonitrile with 0.1% formic acid in water with 0.10% formic acid to give the product, 6, as a yellow powder after lyophilization (42 mg, 25%) Mass spectrum M+H$^+$=586.1.

Other compounds were synthesized in a similar fashion, shown specifically below:

Synthesis of (S,Z)-6-(2-(2-aminothiazol-4-yl)-2-(((2-carboxypropan-2-yl)oxy)imino)acetamido)-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid 11

Synthesis of intermediate tert-butyl (S)-2-((2-(((4,5-bis((4-methoxybenzyl)oxy)pyridin-2-yl)methyl)amino)-2-oxoethyl)carbamoyl)-6-((tert-butoxycarbonyl)amino)-5-oxo-6,7-dihydro-1H,5H-pyrazolo[1,2-a]pyrazole-3-carboxylate 8

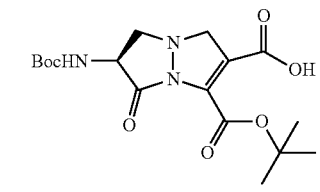

1

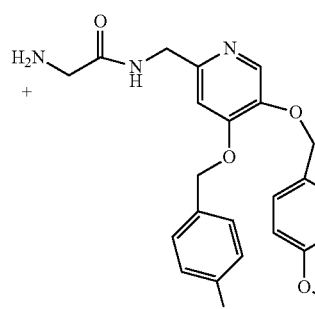

7

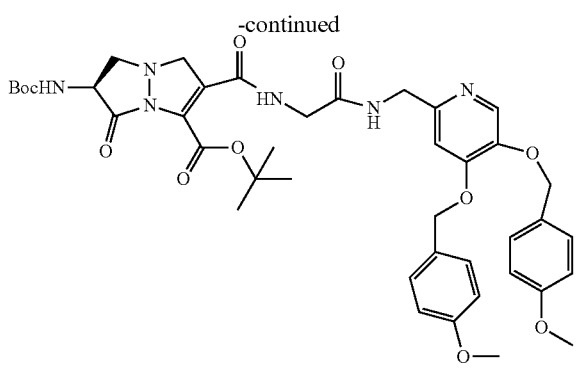

8

Starting acid 1 (260 mg 0.678 mmol) in dry acetonitrile (5 mL) was added DCC (168 mg 1.2 equiv) and HOAT (111 mg, 1.2 equiv) and stirred for 1 hour. To the reaction was added the known amine, 2-amino-N-((4,5-bis((4-methoxybenzyl)oxy)pyridin-2-yl)methyl)acetamide 7 (311 mg, 1.05 equiv) and the reaction was stirred 2 hours and poured into ethyl acetate. The reaction was washed with saturated sodium bicarbonate and brine then back extracted with ethyl acetate. The combined organic layers were dried over magnesium sulfate to give a yellow oil. Purification by MPLC on silica eluting with 0 to 7% ethanol in DCM gave product, 8, (151 mg, 28%) as a foam. Mass spectrum M+H$^+$=803.2.

Synthesis of intermediate (S)-6-amino-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid 9

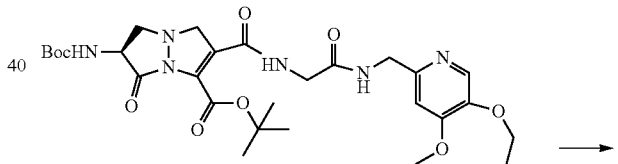

8

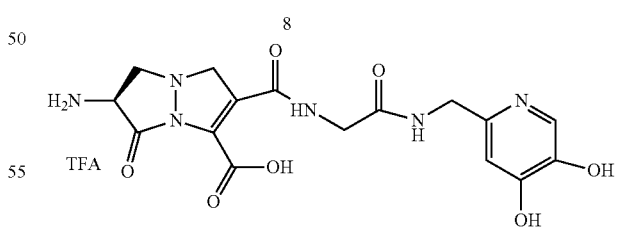

9

Starting material 8 (130 mg, 0.16 mmol) was deprotected as described above for the conversion of 2 to 3 to give product (S)-6-amino-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid, 9, as a yellow foam that was used crude in the next reaction. Mass spectrum M+H$^+$=407.0.

Synthesis of intermediate (S,Z)-6-(2-(((1-(tert-butoxy)-2-methyl-1-oxopropan-2-yl)oxy)imino)-2-(2-(tritylamino)thiazol-4-yl)acetamido)-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid 10

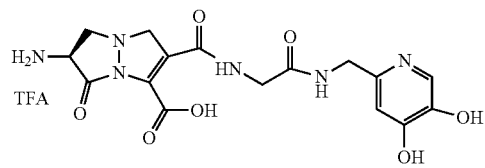

9

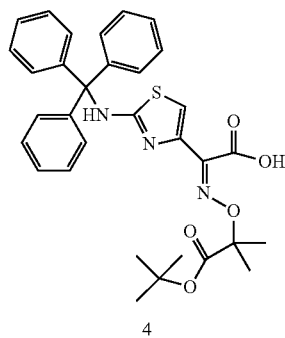

4

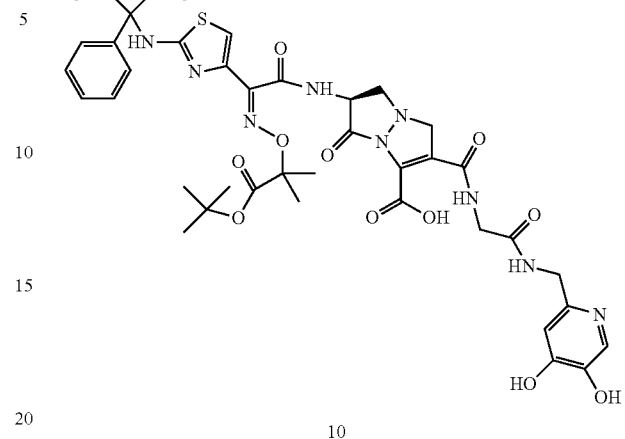

10

The coupling of 9, presumed to be obtained in quantitative yield, and 4 to furnish (S,Z)-6-(2-(((1-(tert-butoxy)-2-methyl-1-oxopropan-2-yl)oxy)imino)-2-(2-(tritylamino)thiazol-4-yl)acetamido)-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid, 10, is as described above for the synthesis of 5. Giving 10 as a yellow foam. Mass spectrum M+H$^+$=960.2.

Synthesis of (S,Z)-6-(2-(2-aminothiazol-4-yl)-2-(((2-carboxypropan-2-yl)oxy)imino)acetamido)-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid 11

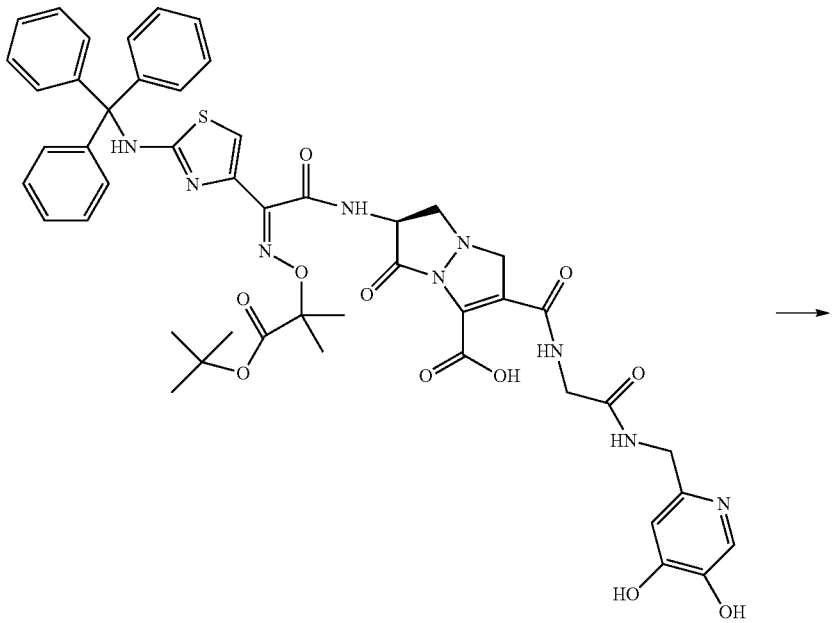

10

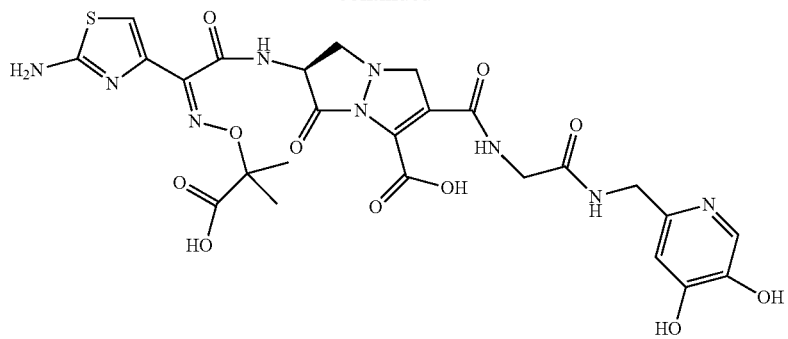

11

Starting material 10 used crude from the previous reaction was deprotected to 11 in a manner similar to the deprotection to give 6. Chromatography using reverse phase C18 MPLC eluting with 10 to 50% acetonitrile with 0.1% formic acid in water with 0.1% formic acid to give the product (S,Z)-6-(2-(2-aminothiazol-4-yl)-2-(((2-carboxypropan-2-yl)oxy)imino)acetamido)-2-((2-(((4,5-dihydroxypyridin-2-yl)methyl)amino)-2-oxoethyl)carbamoyl)-5-oxo-6,7-dihydro-1H,5H-pyrazolo[1,2-a]pyrazole-3-carboxylic acid, 11, as a yellow powder after lyophilization (13 mg, 11%) Mass spectrum M+H$^+$=662.0.

Synthesis of (S,Z)-6-(2-(2-aminothiazol-4-yl)-2-(((2-carboxypropan-2-yl)oxy)imino)acetamido)-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid 16

Synthesis of intermediate tert-butyl (S)-2-(((1,5-bis((4-methoxybenzyl)oxy)-4-oxo-1,4-dihydropyridin-2-yl)methyl)carbamoyl)-6-((tert-butoxycarbonyl)amino)-5-oxo-6,7-dihydro-1H,5H-pyrazolo[1,2-a]pyrazole-3-carboxylate 13

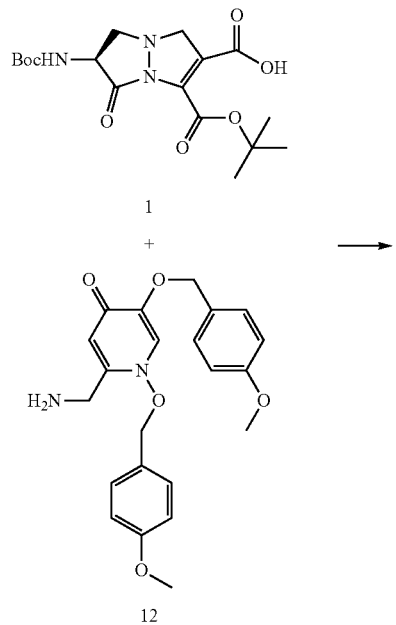

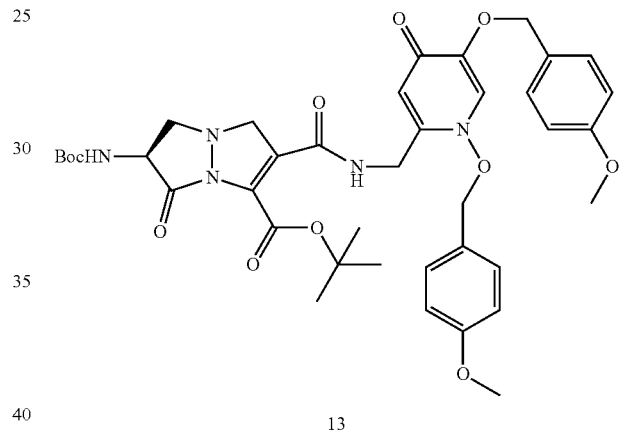

13

The acid 1 (210 mg, 0.55 mmol) in dry dichloromethane (3 mL) and dimethyl formamide (5 uL) was cooled in an ice bath oxalyl chloride (278 uL of 2.0M solution, 1 equiv.) was added. The reaction was stirred for 30 minutes and then added to a solution of the known amine 12 (217 mg, 1.0 equiv.) in DCM (3.0 mL) and Hunig's base (274 uL, 2.5 equiv.). The reaction was stirred for 1 hour, judged complete by TLC and poured into dichloromethane. The reaction was washed with 0.1 N sulfuric acid, water and then saturated sodium bicarbonate. After drying over magnesium sulfate the organics were evaporated to give a yellow foam. Chromatography by MPLC eluting with 0 to 10% ethanol in dichloromethane provided tert-butyl (S)-2-(((1,5-bis((4-methoxybenzyl)oxy)-4-oxo-1,4-dihydropyridin-2-yl)methyl)carbamoyl)-6-((tert-butoxycarbonyl)amino)-5-oxo-6,7-dihydro-1H,5H-pyrazolo[1,2-a]pyrazole-3-carboxylate 13 as a yellow foam (120 mg, 29%). Mass spectrum M+H$^+$=762.2.

Synthesis of intermediate (S)-6-amino-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid 14

Synthesis of intermediate (S,Z)-6-(2-(((1-(tert-butoxy)-2-methyl-1-oxopropan-2-yl)oxy)imino)-2-(2-(tritylamino)thiazol-4-yl)acetamido)-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid 15

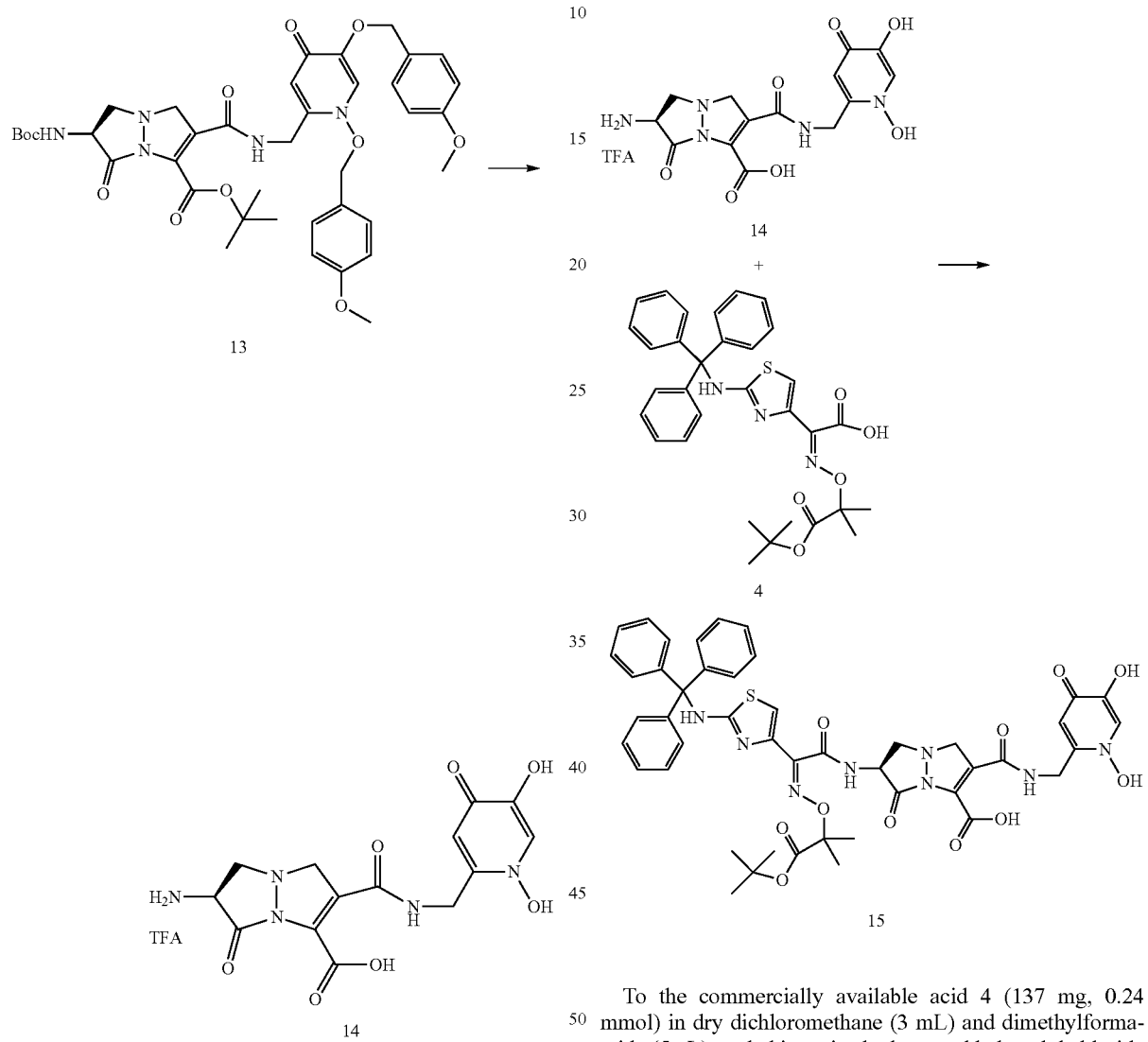

Starting material 13 (120 mg, 0.157 mmol) was deprotected as described above for the synthesis of 9 to give product (S)-6-amino-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid, 14, as a yellow foam that was used crude in the next reaction. Mass spectrum M+H$^+$=366.0.

To the commercially available acid 4 (137 mg, 0.24 mmol) in dry dichloromethane (3 mL) and dimethylformamide (5 uL) cooled in an ice bath was added oxalyl chloride (120 uL, of a 2.0 M solution, 0.24 mmol). The reaction was stirred for 1 hour. In a second flask to the amine 4 (80 mg, 0.22 mmol) was added acetonitrile (2.0 mL), cooled in an ice bath and followed by addition of MSTFA (242 uL, 1.31 mmol) and Hunig's base (149 uL, 0.85 mmol). After stirring for 1 hour the acid chloride solution was added to the cold amine solution, and then allowed to warm to room temperature and stirred 1.5 hours. The reaction was quenched by the addition of methanol and evaporated to dryness. The crude (S,Z)-6-(2-(((1-(tert-butoxy)-2-methyl-1-oxopropan-2-yl)oxy)imino)-2-(2-(tritylamino)thiazol-4-yl)acetamido)-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid 15 was used in the final deprotection. Mass spectrum M+H$^+$=919.2.

Synthesis of (S,Z)-6-(2-(2-aminothiazol-4-yl)-2-(((2-carboxypropan-2-yl)oxy)imino)acetamido)-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid 16

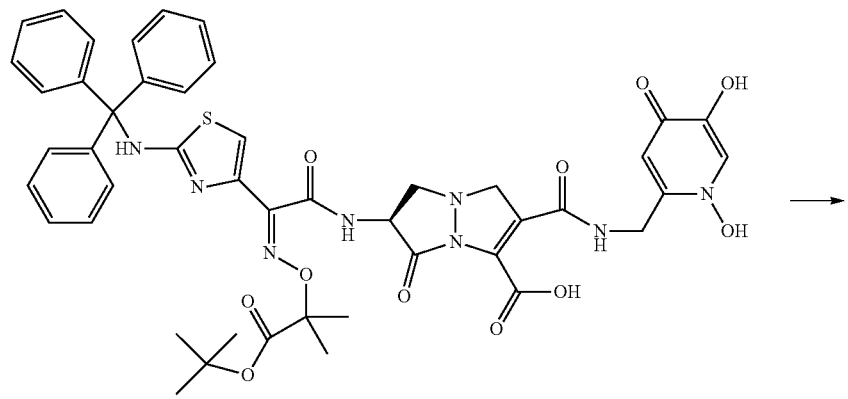

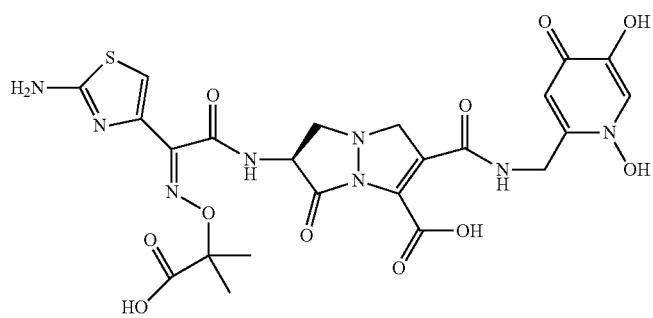

The starting material 15 (221 mg, 0.24 mmol) crude from the previous reaction, was deprotected to 16 in a manner similar to the deprotection to give 6. Chromatography using reverse phase C18 MPLC eluting with 0 to 25% acetonitrile with 0.1% formic acid in water with 0.1% formic acid to give the product (S,Z)-6-(2-(2-aminothiazol-4-yl)-2-(((2-carboxypropan-2-yl)oxy)imino)acetamido)-2-(((1,5-dihydroxy-4-oxo-1,4-dihydropyridin-2-yl)methyl)carbamoyl)-5-oxo-6,7-dihydro-1H,5H-pyrazolo[1,2-a]pyrazole-3-carboxylic acid, 16, as a yellow powder after lyophilization (35 mg, 23%). Mass spectrum M+H$^+$=621.1.

Synthesis of (S,Z)-6-(2-(2-aminothiazol-4-yl)-2-(((2-carboxypropan-2-yl)oxy)imino)acetamido)-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid 21

Synthesis of intermediate tert-butyl (S)-2-(((3-(4,5-bis((4-methoxybenzyl)oxy)pyridin-2-yl)isoxazol-5-yl)methyl)carbamoyl)-6-((tert-butoxycarbonyl)amino)-5-oxo-6,7-dihydro-1H,5H-pyrazolo[1,2-a]pyrazole-3-carboxylate 18

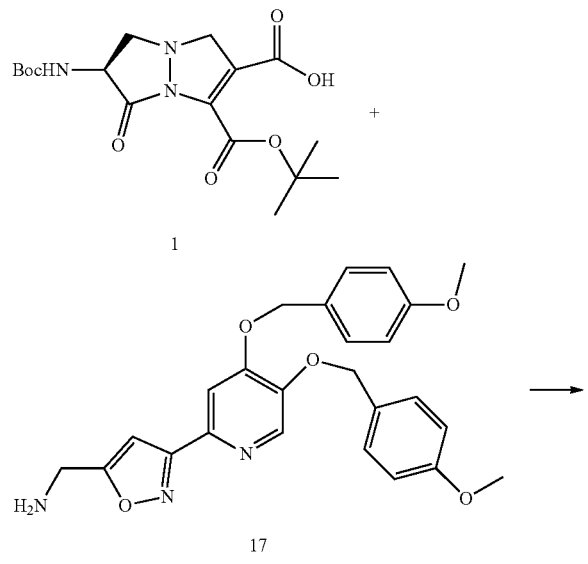

The synthesis of 18 was accomplished in a manner similar to the synthesis of 13 using the acid chloride derived from 1 (200 mg, 0.52 mmol) and the known amine 17 (233 mg, 0.52 mmol). The product tert-butyl (S)-2-(((3-(4,5-bis((4-methoxybenzyl)oxy)pyridin-2-yl)isoxazol-5-yl)methyl)carbamoyl)-6-((tert-butoxycarbonyl)amino)-5-oxo-6,7-dihydro-1H,5H-pyrazolo[1,2-a]pyrazole-3-carboxylate 18 was obtained as a yellow foam (351 mg, 82%). Mass Spectrum M+H$^+$=813.2.

Synthesis of intermediate (S)-6-amino-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid 19

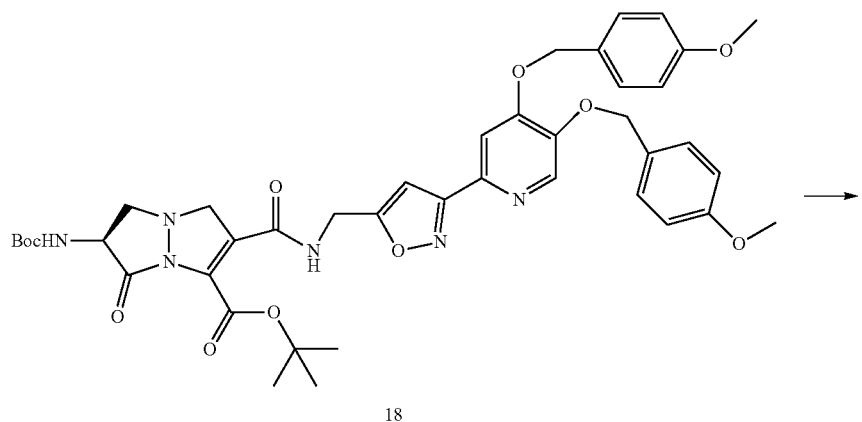

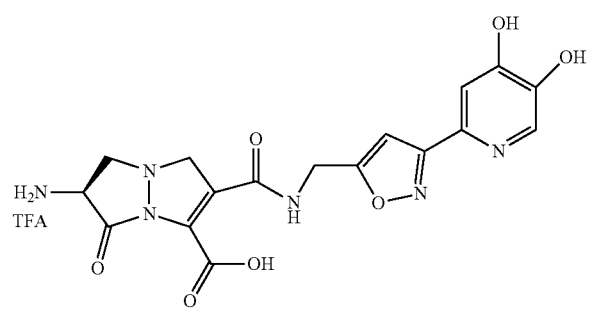

Starting material 18 (320 mg, 0.43 mmol) was deprotected as described above for the synthesis of 9 to give product (S)-6-amino-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid, 19, as a yellow foam that was used crude in the next reaction. Mass spectrum M+H$^+$=417.0.

Synthesis of intermediate (S,Z)-6-(2-(((1-(tert-butoxy)-2-methyl-1-oxopropan-2-yl)oxy)imino)-2-(2-(tritylamino)thiazol-4-yl)acetamido)-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid 20

The synthesis of 20 was accomplished in a manner similar to the synthesis of 15 using the acid chloride derived from 4 (272 mg, 0.48 mmol) and the amine 19 (180 mg, 0.43 mmol). The product (S,Z)-6-(2-(((1-(tert-butoxy)-2-methyl-1-oxopropan-2-yl)oxy)imino)-2-(2-(tritylamino)thiazol-4-yl)acetamido)-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid 20 was obtained as a yellow foam (420 mg, 100%). Mass Spectrum M+H$^+$ (-trityl)=728.0.

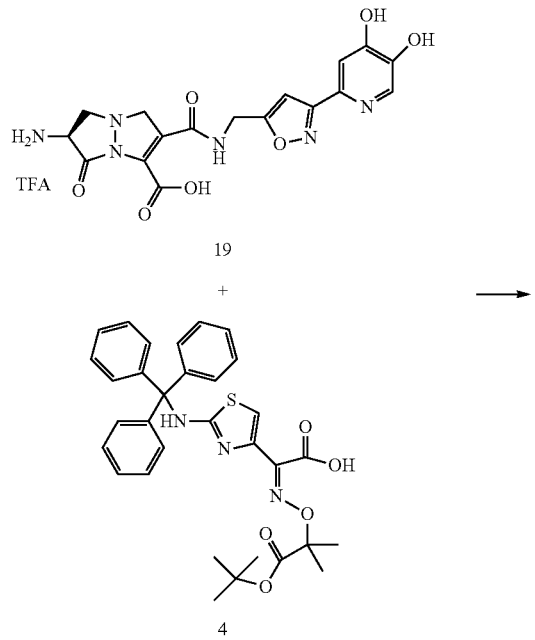

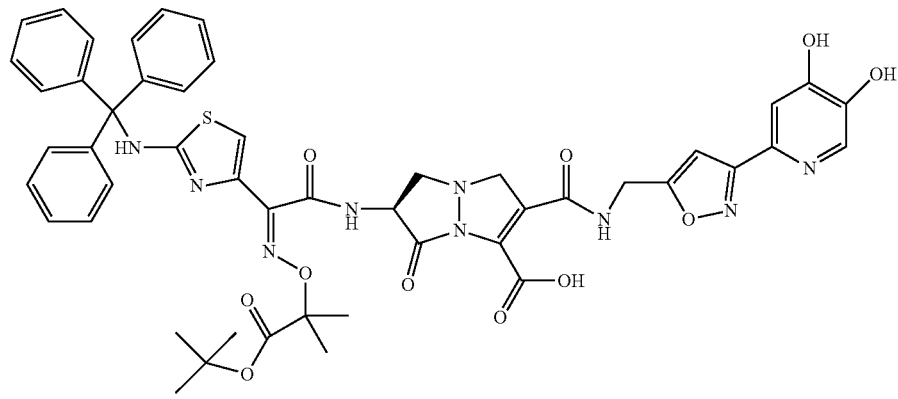

Synthesis of (S,Z)-6-(2-(2-aminothiazol-4-yl)-2-(((2-carboxypropan-2-yl)oxy)imino) acetamido)-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid 21

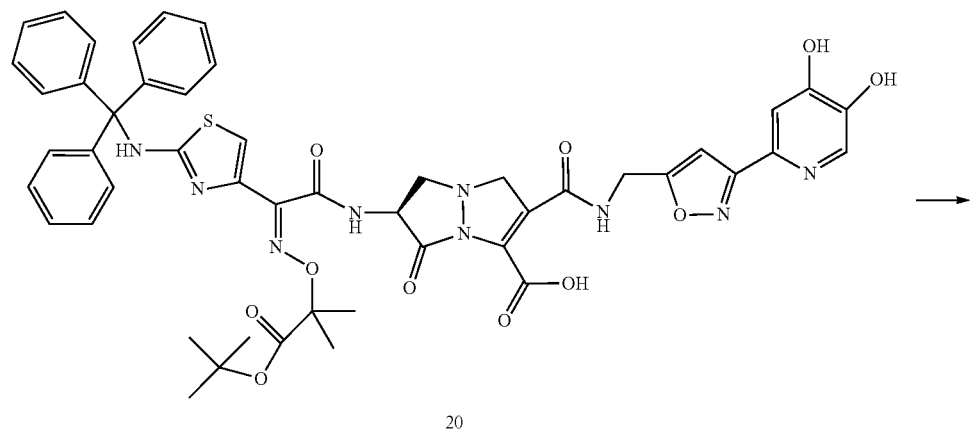

20

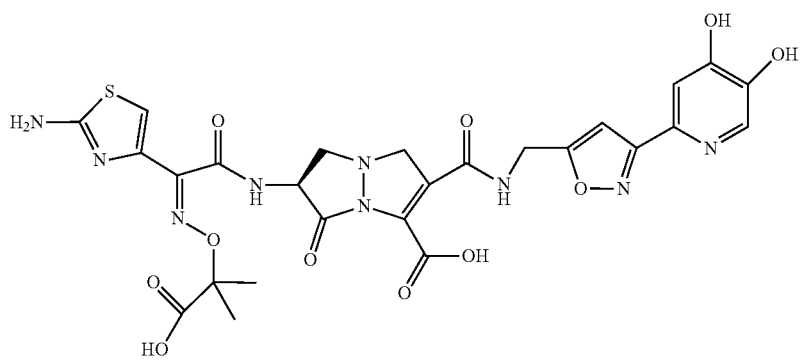

21

The starting material 20 (420 mg, 0.43 mmol) crude from the previous reaction, was deprotected to 21 in a manner like the deprotection to give 6. Chromatography using reverse phase C18 MPLC eluting with 0 to 35% acetonitrile with 0.1% formic acid in water with 0.1% formic acid to give the product (S,Z)-6-(2-(2-aminothiazol-4-yl)-2-(((2-carboxypropan-2-yl)oxy)imino)acetamido)-2-(((3-(4,5-dihydroxypyridin-2-yl)isoxazol-5-yl)methyl)carbamoyl)-5-oxo-6,7-dihydro-1H,5H-pyrazolo[1,2-a]pyrazole-3-carboxylic acid 21 as a yellow powder after lyophilization (57 mg, 19%). Mass spectrum M+H$^+$=672.0.

Synthesis of (S,Z)-6-(2-(2-aminothiazol-4-yl)-2-(((2-carboxypropan-2-yl)oxy)imino)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 26

Synthesis of give tert-butyl (2-(5,6-bis((4-methoxybenzyl)oxy)-1,3-dioxoisoindolin-2-yl)ethyl)carbamate 31

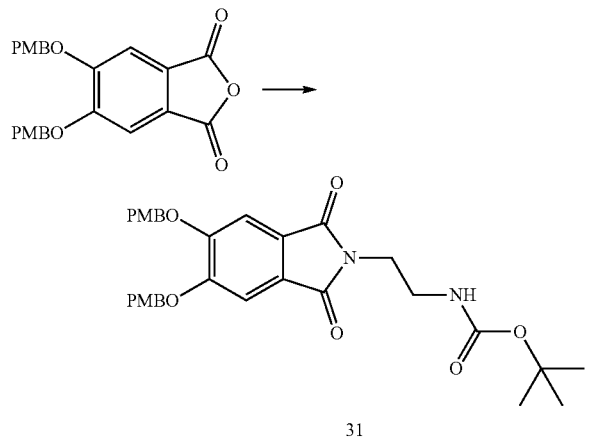

To a solution of 5,6-bis((4-methoxybenzyl)oxy)isobenzofuran-1,3-dione (5.0 g, 11.9 mmol) in EtOH (50 mL) was added N-Boc-ethylenediamine (3.81 g, 23.8 mmol). The solution was heated to reflux for 3 h. The reaction was cooled to room temperature to yield a white precipitate. Water (25 mL) was added to the reaction, the mixture was cooled to 0° C. and the solid was filtered and air-dried to give tert-butyl (2-(5,6-bis((4-methoxybenzyl)oxy)-1,3-dioxoisoindolin-2-yl)ethyl)carbamate (4.26 g, 64% yield). Mass spectrum M+H$^+$=507.2 (-t-butyl).

Synthesis of 2-(2-aminoethyl)-5,6-dihydroxyisoindoline-1,3-dione 22

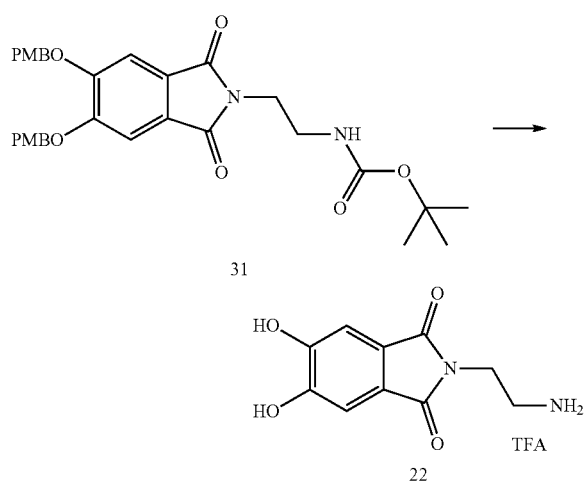

tert-Butyl (2-(5,6-bis((4-methoxybenzyl)oxy)-1,3-dioxoisoindolin-2-yl)ethyl)carbamate (3.85 g, 6.84 mmol) was suspended in DCM (150 mL) and cooled to 0° C. To this was added triethylsilane (5.46 mL, 34.2 mmol) followed by trifluoroacetic acid (26 mL, 340 mmol). Stirring was continued at 0° C. for 1 hour. The reaction was diluted with toluene (50 mL) to give a white solid, which was filtered and air-dried to give 2-(2-aminoethyl)-5,6-dihydroxyisoindoline-1,3-dione (2.11 g, 96% yield) as the TFA salt. Mass spectrum M+H$^+$=223.0.

Synthesis of intermediate tert-butyl (S)-6-((tert-butoxycarbonyl)amino)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylate 23

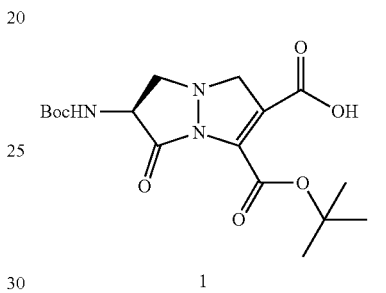

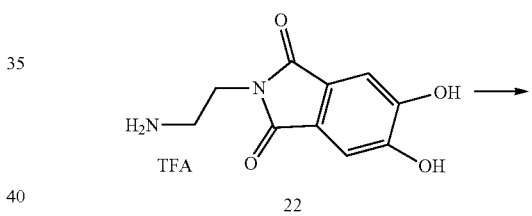

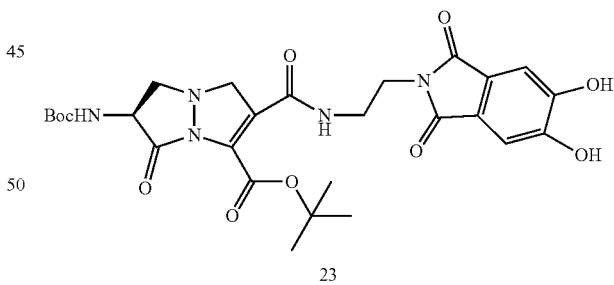

The synthesis of 23 was accomplished in a manner similar to the synthesis of 1 using the acid chloride derived from 1 (694 mg, 1.81 mmol) and amine 22 (336 mg, 1.81 mmol). Prior to reaction with the acid chloride, the amine 22 in acetonitrile (10 mL), was cooled in an ice bath, and then treated with Hunig's base (1.26 mL, 7.24 mmol) and MSTFA (2.0 mL, 10.86 mmol). The product tert-butyl (S)-6-((tert-butoxycarbonyl)amino)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylate 23

Synthesis of Intermediate (S)-6-amino-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 24

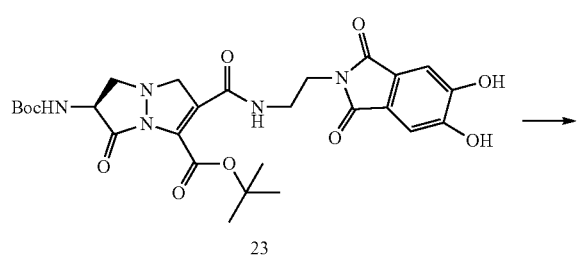

23

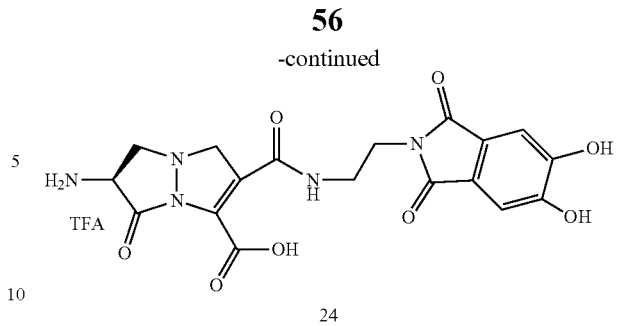

24

Starting material 23 (397 mg, 0.68 mmol) was deprotected as described above for the synthesis of 3 to give product (S)-6-amino-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid, 24, as a yellow foam that was used crude in the next reaction. Mass spectrum M+H$^+$=432.0.

Synthesis of intermediate (S,Z)-6-(2-(((1-(tert-butoxy)-2-methyl-1-oxopropan-2-yl)oxy)imino)-2-(2-(tritylamino)thiazol-4-yl)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 25

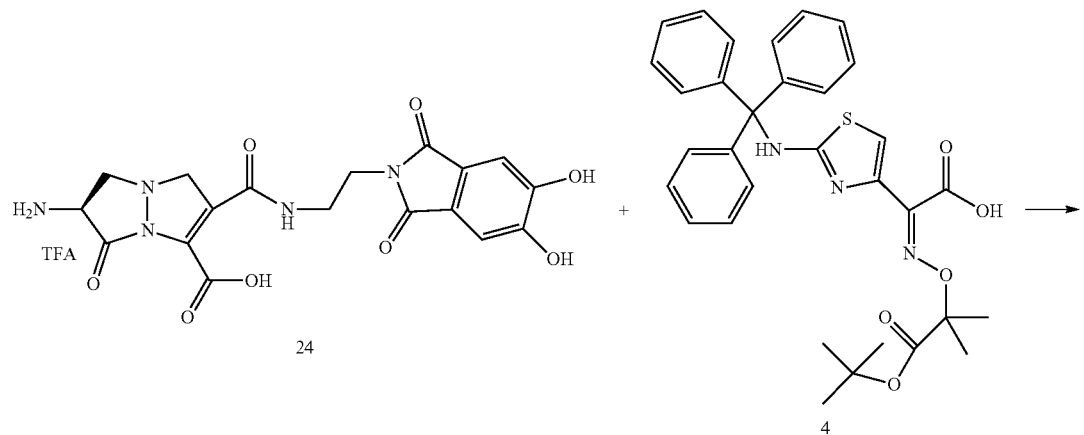

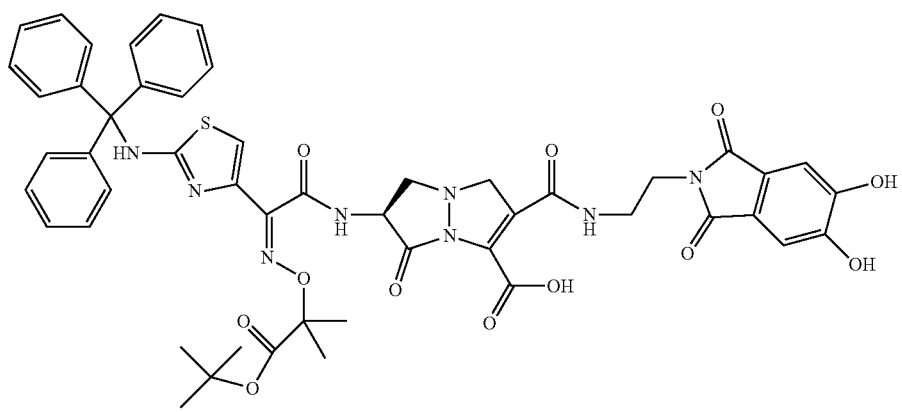

25 was obtained as a yellow foam (408 mg, 38%) after chromatography by MPLC eluting with 40 to 70% (ethyl acetate/methanol/acetic acid, 93.8:6:0.2) in dichloromethane. Mass Spectrum M+H$^+$=588.2.

The synthesis of 25 was accomplished in a manner similar to the synthesis of 1 using the acid chloride derived from 4 (437 mg, 0.76 mmol) and the amine 24 (300 mg, 0.69 mmol). The product (S,Z)-6-(2-(((1-(tert-butoxy)-2-methyl-1-oxopropan-2-yl)oxy)imino)-2-(2-(tritylamino)thiazol-4-yl)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 25 was obtained as a yellow foam that was used directly in the next reaction. Mass Spectrum M+H$^+$=985.2.

Synthesis of (S,Z)-6-(2-(2-aminothiazol-4-yl)-2-(((2-carboxypropan-2-yl)oxy)imino)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 26

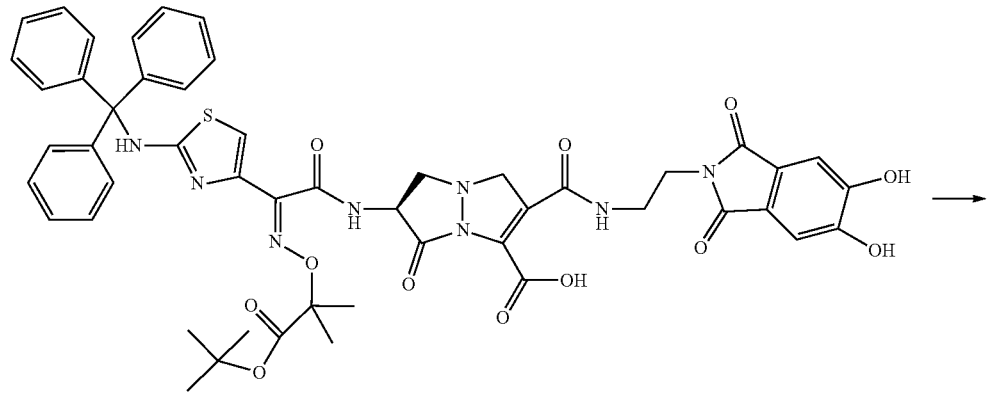

25

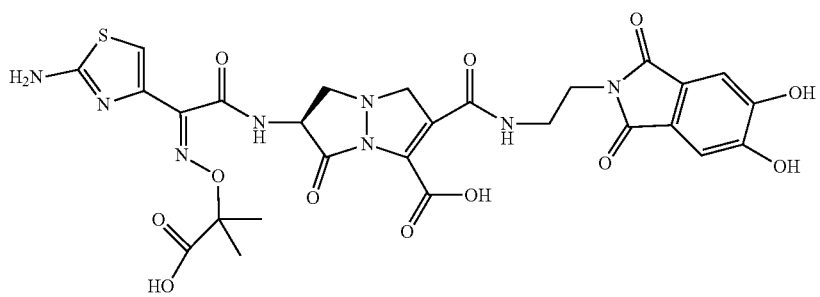

26

The starting material 25 (1.09 g, 1.11 mmol) crude from the previous reaction, was deprotected to 26 in a manner similar to the deprotection to give 6. Chromatography using reverse phase C18 MPLC eluting with 0 to 30% acetonitrile with 0.1% formic acid in water with 0.1% formic acid to give the product (S,Z)-6-(2-(2-aminothiazol-4-yl)-2-(((2-carboxypropan-2-yl)oxy)imino)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid, 26, as a yellow powder after lyophilization (172 mg, 22%). Mass spectrum M+H$^+$=687.1.

Synthesis of allyl 5-(dimethoxyphosphoryl)-4-oxopentanoate 34

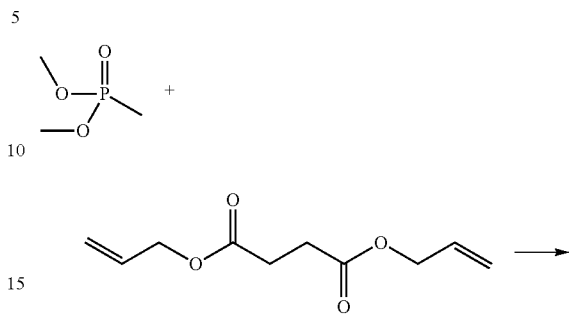

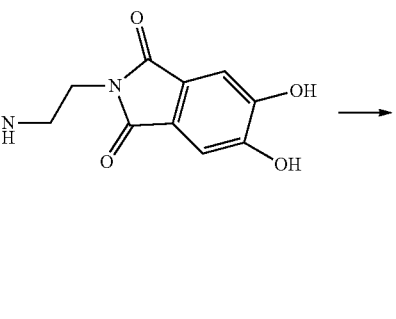

-continued

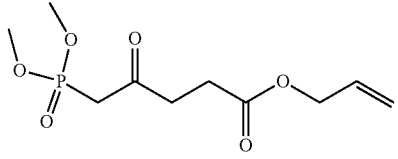

34

A solution of dimethyl methylphosphonate (2.33 g, 18.8 mmol) in THF (20 mL) was cooled to −78° C. and n-BuLi solution (14.7 mL, 23.5 mmol, 1.6 M) was added dropwise.

The reaction was stirred 15 minutes then diallyl succinate (3.1 g, 15.6 mmol) was quickly added. The reaction was stirred 15 minutes at −78° C., then quenched with sat. NH$_4$Cl solution (5 mL) and brought to room temperature. The reaction was poured into sat. NH$_4$Cl solution (75 mL) and extracted with EtOAc (3×50 mL). The combined organics were washed with brine, dried over MgSO$_4$, and concentrated under reduced pressure to give allyl 5-(dimethoxyphosphoryl)-4-oxopentanoate (7.45 g, 86% yield, 48% pure as a mixture with unreacted diallyl succinate). Mass spectrum M+H$^+$=323.1.

Synthesis of allyl 5-(dimethoxyphosphoryl)-6-ethoxy-4-oxohexanoate 35

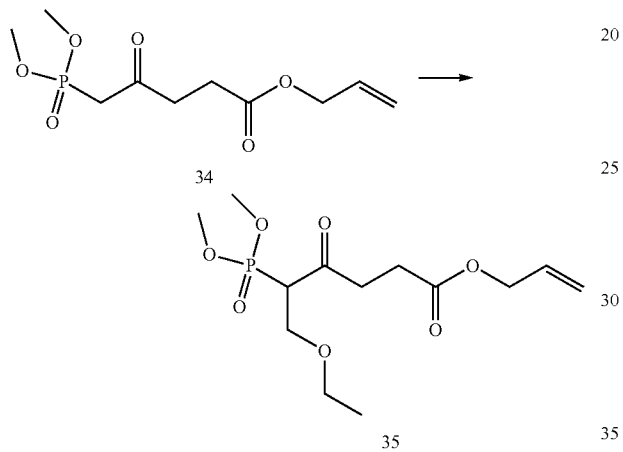

A solution of paraformaldehyde (650 mg, 21.7 mmol) and piperidine (46 mg, 0.54 mmol) were refluxed in EtOH (150 mL) for 1 h. A solution of allyl 5-(dimethoxyphosphoryl)-4-oxopentanoate (7.45 g [48% pure], 13.5 mmol) in EtOH (20 mL) was added via syringe pump over 90 minutes. The reaction was stirred for an additional 1 h at reflux. The reaction was concentrated under reduced pressure onto silica gel, then purified via flash chromatography (0-10% MeOH/DCM) to give allyl 5-(dimethoxyphosphoryl)-6-ethoxy-4-oxohexanoate (3.65 g, 84% yield). Mass spectrum M+H$^+$=323.1.

Synthesis of (S)-4-(3-(tert-butoxycarbonyl)-6-((tert-butoxycarbonyl)amino)-5-oxo-6,7-dihydro-1H,5H-pyrazolo[1,2-a]pyrazol-2-yl)-4-oxobutanoic acid 3

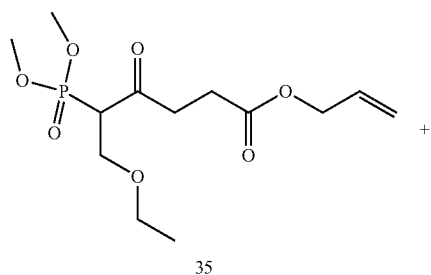

+

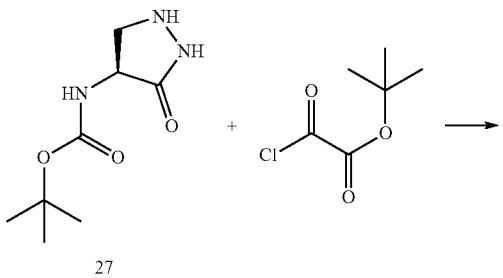

Allyl 5-(diethoxyphosphoryl)-6-ethoxy-4-oxohexanoate (599 mg, 1.86 mmol) and tert-butyl (S)-(3-oxopyrazolidin-4-yl)carbamate (343 mg, 1.70 mmol) were combined in EtOH (10 mL) and heated at 50° C. for 1 h. The reaction was concentrated under reduced pressure, chased with toluene, and taken up in DCM (18 mL) and cooled to 0° C. To this was added tert-butyl 2-chloro-2-oxoacetate (309 mg, 1.88 mmol). After 10 minutes, Hunig's base (0.62 mL, 3.58 mmol) was added. The reaction was warmed to room temperature and stirred for 2 h. The reaction was diluted with DCM (50 mL) and the reaction wash washed with 1 M H$_2$SO$_4$ solution (25 mL), water (25 mL) and brine. The organic layer was dried over MgSO$_4$, filtered, and concentrated under reduced pressure to give the crude product. This was taken up ACN (10 mL) and cooled to 0° C. To this was added triethylsilane (0.33 mL, 2.04 mmol) followed by Pd(PPh$_3$)$_4$ (157 mg, 0.14 mmol). This was stirred at 0° C. for 30 min, then 1 hour at room temperature. The reaction was quenched by addition of 0.1 M HCl solution (10 mL) and stirred for 30 minutes. This was then diluted with EtOAc (60 mL) and the aqueous layer was discarded. The organics are extracted with 50% saturated NaHCO$_3$ solution (2×25 mL). The combined aqueous layers were neutralized with 1 M H$_2$SO$_4$ and extracted with EtOAc (3×25 mL). The combined organics are washed with brine, dried over MgSO$_4$, and concentrated under reduced pressure to give (S)-4-(3-(tert-butoxycarbonyl)-6-((tert-butoxycarbonyl)amino)-5-oxo-6,7-dihydro-1H,5H-pyrazolo[1,2-a]pyrazol-2-yl)-4-oxobutanoic acid (250 mg, 33% yield). Mass spectrum M+H$^+$=440.2.

Synthesis of dimethyl (1-ethoxy-3-oxobutan-2-yl)phosphonate 36

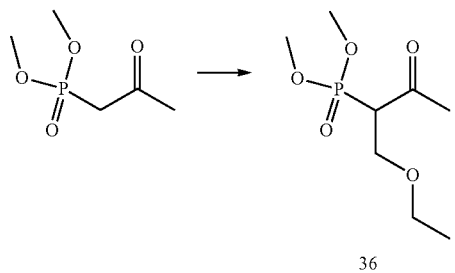

A solution of paraformaldehyde (1.74 g, 57.8 mmol) and piperidine (123 mg, 1.44 mmol) were refluxed in EtOH (150 mL) for 1 h. A solution of dimethyl (2-oxopropyl)phosphonate (6.0 g, 36.1 mmol) in EtOH (20 mL) was added via syringe pump over 90 minutes. The reaction was stirred for an additional 1 h at reflux. The reaction was concentrated under reduced pressure onto silica gel, then purified via flash chromatography (0-20% MeOH/DCM) to give dimethyl (1-ethoxy-3-oxobutan-2-yl)phosphonate (5.08 g, 63% yield). Mass spectrum M+H$^+$=225.1.

Synthesis of (S)-2-acetyl-6-((tert-butoxycarbonyl)amino)-5-oxo-6,7-dihydro-1H,5H-pyrazolo[1,2-a]pyrazole-3-carboxylic acid 38

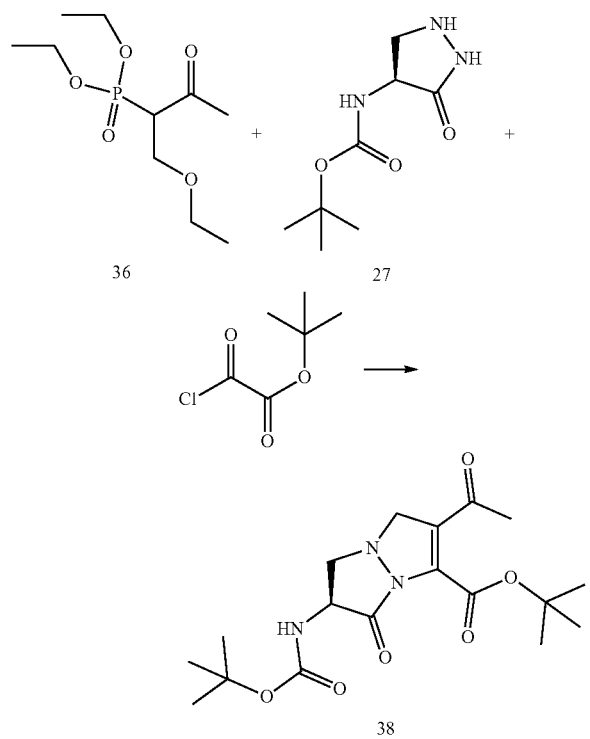

Synthesis of (S)-2-acetyl-6-((tert-butoxycarbonyl)amino)-5-oxo-6,7-dihydro-1H,5H-pyrazolo[1,2-a]pyrazole-3-carboxylic acid was achieved in a manner analagous to 37. Mass spectrum M+H$^+$=382.1.

Synthesis of 4-((S)-3-(tert-butoxycarbonyl)-6-((tert-butoxycarbonyl)amino)-5-oxo-6,7-dihydro-1H,5H-pyrazolo[1,2-a]pyrazol-2-yl)-2-hydroxy-4-oxobutanoic acid 39

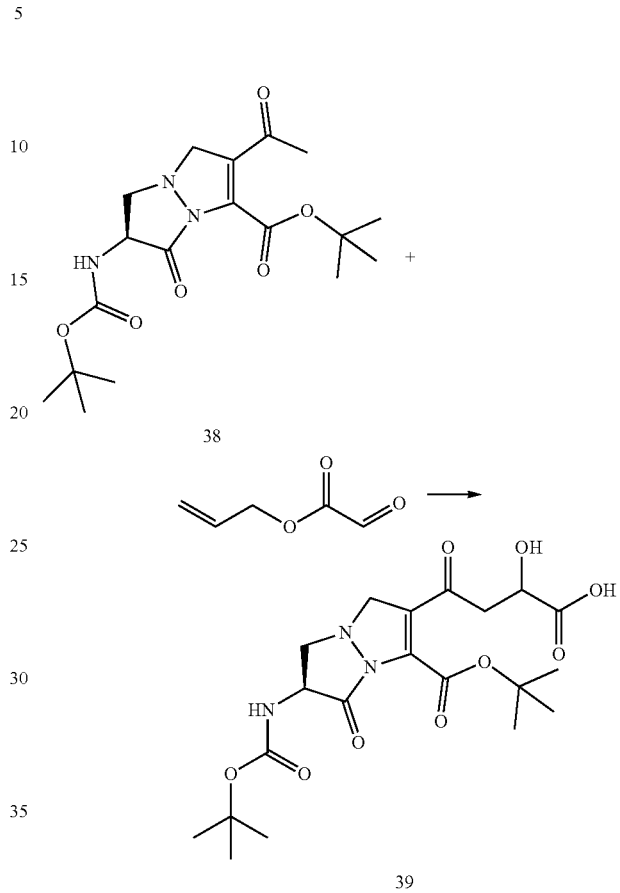

To THF (9 mL) cooled to −78° C. was added LiHMDS (3.13 mL, 3.13 mL, 1 M in THF). A solution of tert-butyl (S)-2-acetyl-6-((tert-butoxycarbonyl)amino)-5-oxo-6,7-dihydro-1H,5H-pyrazolo[1,2-a]pyrazole-3-carboxylate (545 mg, 1.42 mmol) in THF (3 mL) was added dropwise to the LiHMDS solution. This was stirred at −78° C. for 10 min, at which point allyl 2-oxoacetate (810 mg, 1.71 mmol, 24% solution in 1,4-dioxane) was added dropwise. The reaction was stirred at −78° C. for 15 min, then quenched with THF/AcOH. The reaction was diluted with EtOAc, washed with 1 M H$_2$SO$_4$ solution, brine, dried over MgSO$_4$, and concentrated. The material was taken up in ACN (25 mL) and cooled to 0° C. To this was added triethylsilane (0.30 mL, 1.89 mmol) followed by Pd(PPh$_3$)$_4$ (145 mg, 0.13 mmol). This was stirred at 0° C. for 30 min, then 1 hour at room temperature. The reaction was quenched by addition of 0.1 M HCl solution (10 mL) and stirred for 30 minutes. This was then diluted with EtOAc (60 mL) and the aqueous layer was discarded. The organics were extracted with 50% saturated NaHCO$_3$ solution (2×25 mL). The combined aqueous layers were neutralized with 1 M H$_2$SO$_4$ and extracted with EtOAc (3×25 mL). The combined organics were washed with brine, dried over MgSO$_4$, and concentrated under reduced pressure to give 4-((S)-3-(tert-butoxycarbonyl)-6-((tert-butoxycarbonyl)amino)-5-oxo-6,7-dihydro-1H,5H-pyrazolo[1,2-a]pyrazol-2-yl)-2-hydroxy-4-oxobutanoic acid (254 mg, 36% yield). Mass spectrum M+H$^+$=456.1.

Synthesis of Intermediate (S,Z)-6-(2-(((1-(tert-butoxy)-2-methyl-1-oxopropan-2-yl)oxy)imino)-2-(5-chloro-2-(tritylamino)thiazol-4-yl)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 41

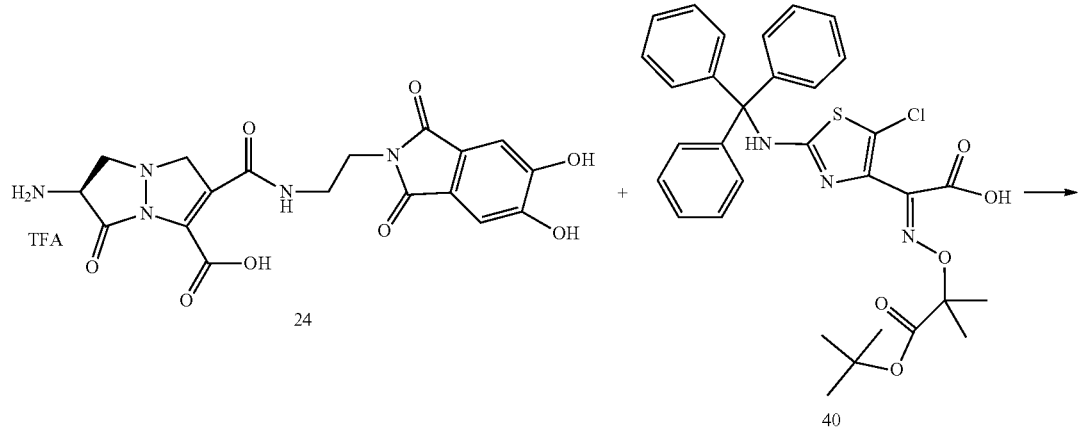

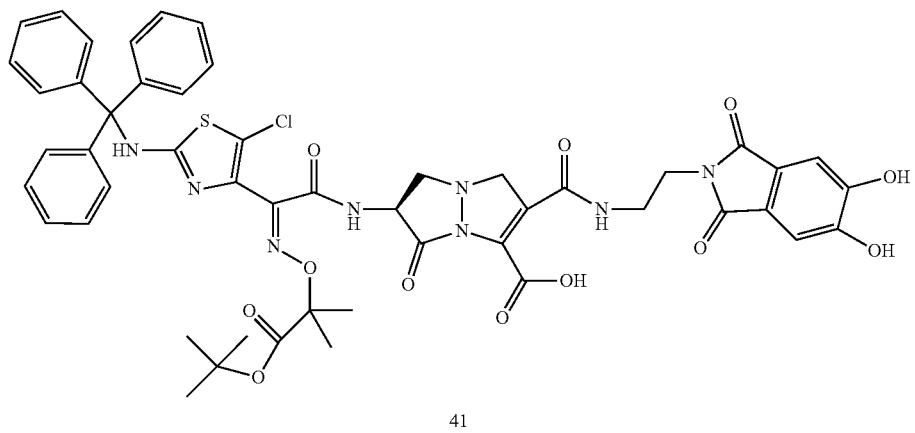

The synthesis of 41 was accomplished in a manner similar to the synthesis of 1 using the acid chloride derived from 40 (434 mg, 0.72 mmol) and the amine 24 (281 mg, 0.65 mmol). The product (S,Z)-6-(2-(((1-(tert-butoxy)-2-methyl-1-oxopropan-2-yl)oxy)imino)-2-(5-chloro-2-(tritylamino)thiazol-4-yl)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 41 was obtained as a yellow foam that was used directly in the next reaction. Mass Spectrum M+H$^+$=1020.4.

Synthesis of (S,Z)-6-(2-(2-amino-5-chlorothiazol-4-yl)-2-(((2-carboxypropan-2-yl)oxy)imino)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 42

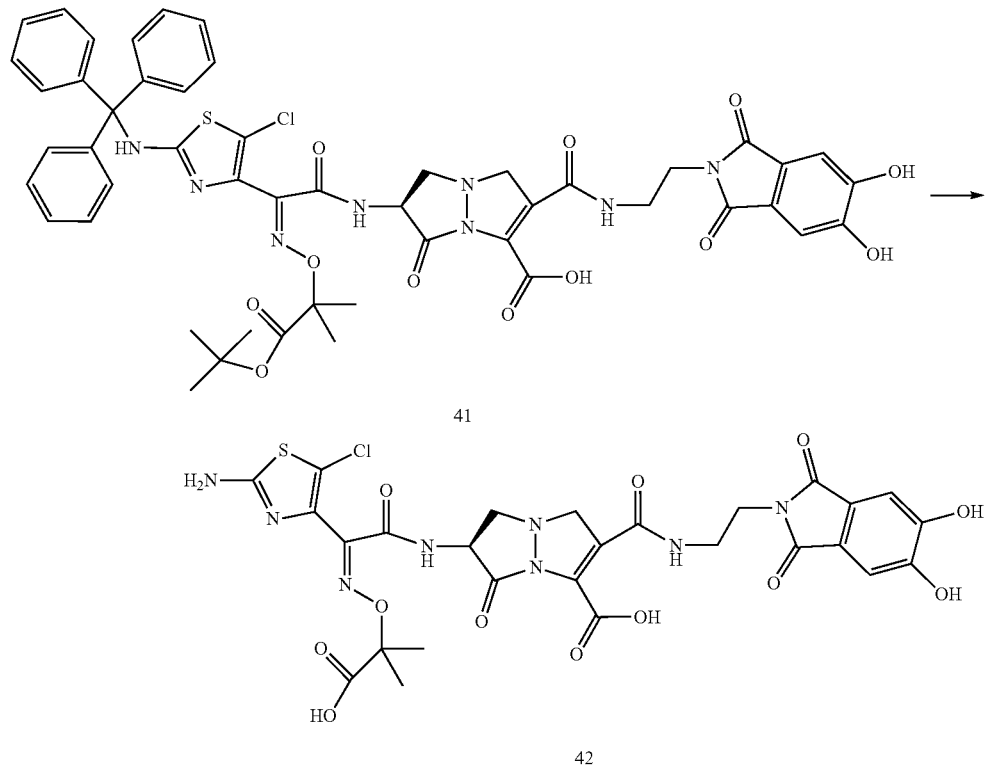

The starting material 41 (665 mg, 0.652 mmol) crude from the previous reaction, was deprotected to 42 in a manner similar to the deprotection to give 6. Chromatography using reverse phase C18 MPLC eluting with 0 to 40% acetonitrile with 0.1% formic acid in water with 0.1% formic acid to give the product (S,Z)-6-(2-(2-amino-5-chlorothiazol-4-yl)-2-(((2-carboxypropan-2-yl)oxy)imino)acetamido)-2-((2-(5,6-dihydroxy-1,3-dioxoisoindolin-2-yl)ethyl)carbamoyl)-5-oxo-6,7-dihydro-1H,5H-pyrazolo[1,2-a]pyrazole-3-carboxylic acid 41, as a yellow powder after lyophilization (75 mg, 16%). Mass spectrum M+H$^+$=721.0.

Example 2

Quantification of pyrazolidinone activity focused on comparing non-siderophore containing analogs to C(3) conjugated pyrazolidinone analogs, extended C(3) analogs and existing clinical agents such as Aztreonam and Meropenem. MICs were conducted against an isogenic library of Ec DH10B strains expressing 40 different beta lactamases (Blas) cloned in a uniform genetic background from all representative classes (class A, C, D and B), as well as Pa, Ab and Kp strains including PA01, Ab 0057 (complete genome sequence is available), Ab HUMC1 which is a carbapenem-resistant highly virulent clinical bloodstream isolate, and KPCKP1 which is a pan-resistant (including to colistin) virulent clinical bloodstream isolate of KPC *K. pneumonia*.

This panel established initial antibacterial efficacy and stability against BLas with emphasis on ESBLs, AmpCs and KPCs as well as important class D enzymes such as OXA-23, -24, and -48. The use of a Pa TonB KO strain in the primary assay panel also elucidated the transport mechanism of the new agents, as TonB function is required for all $Fe^{3+}$ siderophore uptake routes by providing energy for the transport process via ATPase activity.

Example 3

To assess the affinity of the inhibitors for PBP3 and PBP1a and PBP1b, a Bocillin based assay using PA01 membranes as well as purified proteins is used. Delineation of remarkably active compounds occurs by establishing the $MIC_{90}$ against Ec, Pa, Ab and Kp as well as static time kill measurement. When siderophore linked pyrazolidinone agents show remarkable activity (i.e. activity equal to or greater than current clinical agents Meropenem or Aztreonam) in these latter secondary assays, they are tested in vivo in a mouse septicemia efficacy model after protein binding measurement and will show potent in vivo activity.

Example 3: Activity of Compound (26)

Microdilution Broth Minimum Inhibitory Concentrations (MICs)

MICs were performed in triplicate in cation adjusted Mueller-Hinton (MH) broth 30 according to CLSI guidelines. Firstly, overnight cultures of *E. coli* and *K. pneumoniae* clinical isolates were inoculated into 5 ml MH broth to $OD_{600}$=0.1 and grown to $OD_{600}$=0.224 (approximately 1-2×

10$^8$ CFU/ml). These cultures were diluted (3 μl+4997 μl MH) and 100 μl inoculated into each well of a 96-well plate containing 100 μl of serial dilutions of compound 26 (YU253434), ampicillin, ceftazidime, or imipenem. The plates were placed in a 37° C. incubator for 18-20 hours and wells checked for growth.

TABLE 1

| Strain | β-lactamase | MIC (μg/mL) | | | |
|---|---|---|---|---|---|
| | | 26 | Ampicillin | Ceftazidime | Imipenem |
| K. pneumoniae 7000063 | SHV-18 | 2 | 1024 | 16 | <0.125 |
| K. pneumoniae VA-357 | KPC-2, SHV-11 | 2 | >2048 | 128 | 8 |
| K. pneumoniae VA-184 | KPC-2, SHV-11, SHV-12 | 4 | >2048 | 256 | 8 |
| K. pneumoniae VA-384 | KPC-2, TEM-1, SHV-11, SHV-12, SHV-14 | 8 | >2048 | 256 | 32 |
| K. pneumoniae VA-406 | KPC-2, TEM-1, SHV-11, SHV-12 | 4 | >2048 | 256 | >128 |
| K. pneumoniae VA-400 | KPC-2, TEM-1, SHV-11, SHV-12 | 4 | >2048 | 256 | 4 |
| K. pneumoniae VA-368 | KPC-2, TEM-1, SHV-5, SHV-68 | 0.25 | >2048 | 16 | 1 |
| K. pneumoniae VA-410 | KPC-3, TEM-1, SHV-11 | 4 | >2048 | 128 | 2 |
| K. pneumoniae VA-267 | KPC-3, TEM-1, SHV-11, SHV-12 | 1 | >2048 | 512 | 4 |
| K. pneumoniae VA-398 | KPC-3, TEM-1, SHV-11, SHV-12, SHV-27 | 8 | >2048 | 32 | 1 |
| K. pneumoniae VA-391 | KPC-3, TEM-1, SHV-11, SHV-12, SHV-77 | 4 | >2048 | 256 | 4 |
| K. pneumoniae LC102 | SHV-1 (WT + 238S) | 1 | >2048 | 4 | <0.125 |
| K. pneumoniae LC121 | SHV-1 (WT + 238S + 240K) | 4 | 1024 | 16 | <0.125 |
| K. pneumoniae LC40 | CTX-M-1 grp(15), TEM (164S) | 16 | 512 | <1 | 0.25 |
| K. pneumoniae Rush23 | CTX-M-9 group | 2 | >2048 | 2 | <0.125 |
| K. pneumoniae LC56 | CTX-M-1 grp(15) | 0.5 | >2048 | 16 | 0.5 |
| K. pneumoniae KB390 Quale | TEM-30, TEM-1, KPC-2, SHV-12 | 2 | >2048 | 512 | 4 |
| E. coli 35218 | TEM-1 | 0.125 | 256 | <1 | <0.125 |
| E. coli BAA-202 | SHV-1 | 4 | >2048 | 16 | 0.25 |
| E. coli LC98 | CMY (group II) | 4 | 2048 | 256 | <0.125 |
| E. coli Rush24 | CMY (group II) | 8 | >2048 | 256 | 0.25 |
| E. coli LC91 | CTX-M-1 grp(15), CMY (group II) | 2 | 2048 | 16 | <0.125 |
| E. coli LC109 | CTX-M-9 group, CMY (group II) | 0.25 | 1024 | 32 | <0.125 |
| E. coli LC38 | CTX-M-1 grp(15), PB AmpC (ACT/MIR) | 0.25 | 512 | <1 | <0.125 |
| E. coli LC41 | TEM (238S), PB AmpC (ACT/MIR), CTX-M-1 grp(15) | 16 | 512 | <1 | <0.125 |
| E. coli LC136 | SHV (WT + 238S) | 0.125 | 512 | <1 | <0.125 |
| E. coli LC81 | SHV (238S + 240K) | 16 | 2048 | 128 | <0.125 |
| E. coli LC111 | TEM (164S) | 1 | 1024 | 2 | <0.125 |
| E. coli LC4 | TEM, SHV-12 | 16 | >2048 | 256 | <0.125 |
| E. coli LC77 | TEM, KPC | 0.5 | 2048 | 16 | 2 |
| E. coli LC12 | CTX-M-1 grp(15) | >128 | 2048 | >1024 | 128 |
| E. coli LC33 | CTX-M-9 group | 1 | 512 | 4 | <0.125 |
| E. coli LC15 | CTX-M-9 group, CTX-M-1 grp(15) | 2 | 1024 | <1 | <0.125 |

Tables 2 and 3 show MIC values of compound 26 (YU253434) and 42 YU253911 versus *E. coli* and *P. Aeruginosa* strains containing Class B metallo beta lactamases VIM and NDM compared with Meropenem as a standard.

TABLE 2

*E. coli*

| Isolate # | Organism ID | Resistance/ Beta-lactamases | Date Tested | MIC (µg/ml) Meropenem | MIC (µg/ml) YU253434 | MIC (µg/ml) YU253911 |
|---|---|---|---|---|---|---|
| ATCC 25822 | E. coli | CLSI costrol | May 7, 2019 | ≤0.125 | 2 | >64 |
| J4244 | E. coli | MN | May 7, 2019 | ≤0.125 | 2 | >64 |
| J4245 | E. coli | Michigan | May 7, 2019 | ≤0.125 | 0.25 | >64 |
| AR-1 | E. coli | KPC-3 | May 7, 2019 | 4 | 1 | >64 |
| AR-11 | E. coli | CTX-M-15, OxA-1 | May 7, 2019 | ≤0.125 | 0.5 | 4 |
| AK-114 | E. coli | KPC-3, TEM-18 | May 7, 2019 | 4 | 0.5 | 2 |
| AA-118 | E. coli | NDM | May 7, 2019 | >64 | 4 | >64 |
| AA-119 | E. coli | NDM | May 7, 2019 | 64 | 4 | >64 |
| AA-128 | E. coli | NDM | May 7, 2019 | 64 | 4 | >64 |
| AR-137 | E. coli | NDM-6 | May 7, 2019 | >64 | 4 | >64 |
| AR-145 | E. coli | NDM | May 7, 2019 | >64 | >64 | >64 |

TABLE 3

*Pseudomonas aeruginosa*

| Isolate # | Organism ID | Resistance/ Beta-lactamases | Date Tested | MIC (µg/ml) Meropenem | MIC (µg/ml) YU253434 | MIC (µg/ml) YU253911 |
|---|---|---|---|---|---|---|
| ATCC 27853 | P. aeruginosa | CLSI control | May 7, 2019 | 1 | 0.25 | 0.5 |
| J4242 | P. aeruginosa | UNC-D | May 7, 2019 | 16 | 0.5 | 0.5 |
| AR-229 | P. aeruginosa | OXA-50 | May 7, 2019 | 64 | 0.25 | 0.5 |
| AR-230 | P. aeruginosa | VIM-2 | May 7, 2019 | >64 | 1 | 1 |
| AR-231 | P. aeruginosa | KPC-5 | May 7, 2019 | >64 | 0.5 | 1 |
| AR-232 | P. aeruginosa | OXA-50 | May 7, 2019 | 8 | 0.5 | 0.5 |
| AR-245 | P. aeruginosa | VIM | May 7, 2019 | 32 | 0.5 | 0.5 |
| AR-249 | P. aeruginosa | VIM | May 7, 2019 | >64 | 1 | 1 |
| AR-252 | P. aeruginosa |  | May 7, 2019 | 64 | 1 | 1 |
| AR-254 | P. aeruginosa | VIM | May 7, 2019 | >64 | 2 | 2 |
| AR-270 | P. aeruginosa | OXA-50 | May 7, 2019 | 4 | 0.25 | 0.25 |

Example 5: Neutropenic Thigh Infection Model

Specific pathogen-free female ICR mice weighing approximately 20-22 grams are obtained from Envigo Laboratories, Inc. (Indianapolis, Ind.) and utilized throughout the experiment. Mice are provided food and water ad libitum. Mice are rendered transiently neutropenic by injecting cyclophosphamide via intraperitoneal (IP) injection at a dose of 150 mg/kg of body weight at four days before inoculation and 100 mg/kg of body weight at one day before inoculation. Three days prior to the inoculation, mice also receive a single IP injection of 5 mg/kg of uranyl nitrate. Administration of uranyl nitrate induces a predictable degree of renal impairment to assist with achieving the target exposures of this renally eliminated compound. Isolates to be inoculated into the thighs are previously frozen at −80° C. in skim milk. Two transfers of the organism are performed onto Trypticase Soy Agar plates with 5% sheep blood (Becton, Dickinson & Co.; Sparks, Md.) and placed into an incubator at 37° C. for approximately 24 hours. After an 18-24 hour incubation of the 2nd transfer, a bacterial suspension of approximately 107 CFU/ml is made for inoculation. Final inoculum concentrations are confirmed by serial dilution and plating techniques. Thigh infection with each of the test isolates is produced by intramuscular injection of 0.1 ml of the inoculum into each thigh of the mice 2 hours prior to the initiation of therapy.

Given the likelihood that a percentage of the isolates does not establish a viable infection in vivo, a total of 12 isolates are tested in order to yield the required 6 isolates. For these studies groups of 6 animals per isolate are divided into 0 h and 24 h control groups. The test article is dosed SC at three daily doses with total doses ranging from 30 to 300 mg/kg. For the analysis of the test compound, efficacy is calculated as the change in bacterial density obtained in treated mice after 24 hours compared with the numbers in the starting control animals (time 0). The change in bacterial density in tissues, expressed as change in $\log_{10}$ CFU, for both treated and untreated animals is reported using descriptive statistics.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula (I), or a salt, solvate, enantiomer, diastereoisomer, tautomer, or geometric isomer thereof:

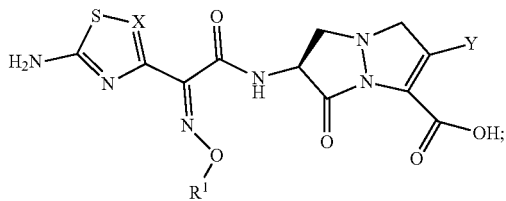

wherein:

R[1] is selected from the group consisting of:

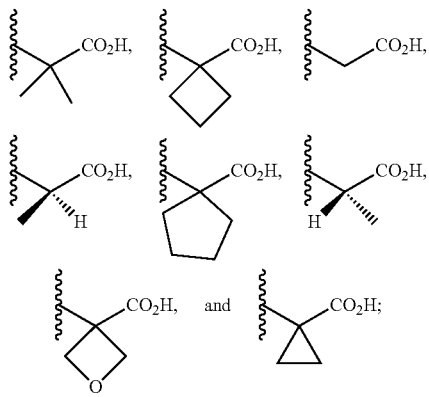

X is selected from the group consisting of CH, CF, CCl, and N;

Y is selected from the group consisting of:

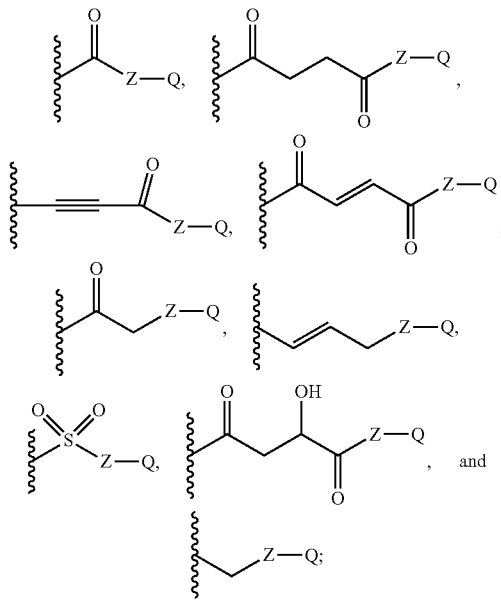

Z is a divalent group selected from the group consisting of —NH—, —NMe-, —O—, and —S—; and Q is a siderophore or a siderophore mimic.

2. The compound of claim 1, wherein Q is selected from the group consisting of:

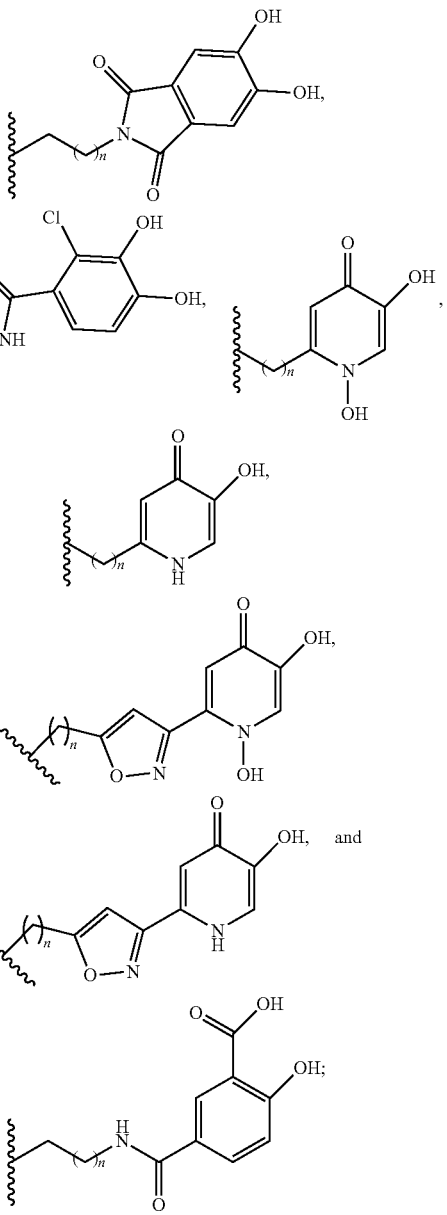

wherein each occurrence of n is independently selected from the group consisting of 0, 1, 2, and 3.

3. The compound of claim 1, wherein:

R[1] is selected from the group consisting of:

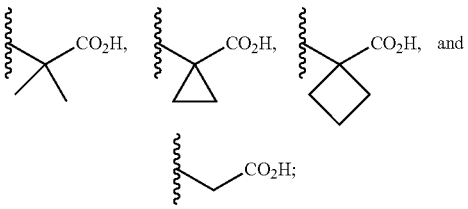

Y is selected from the group consisting of:
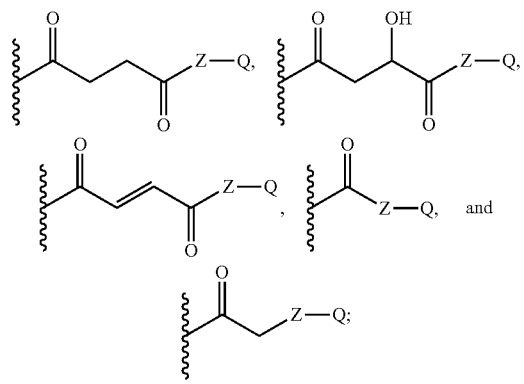
and
Q is selected from the group consisting of:
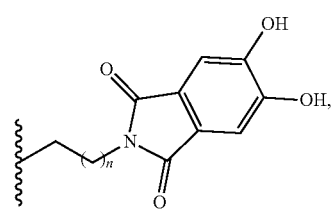
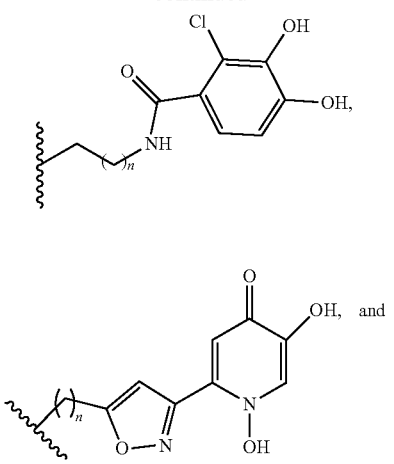
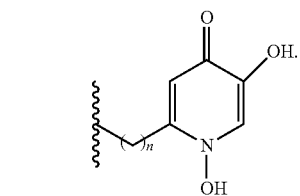
4. The compound of claim 1, which is selected from the group consisting of:
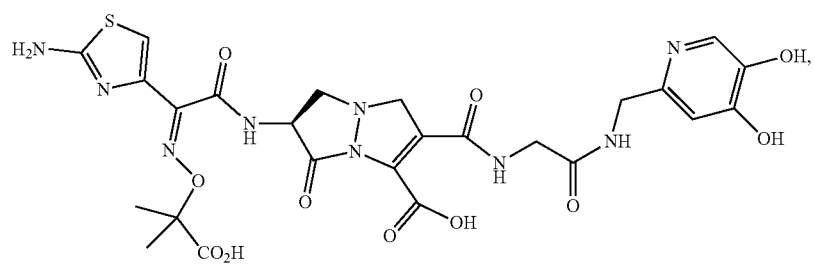
(11)
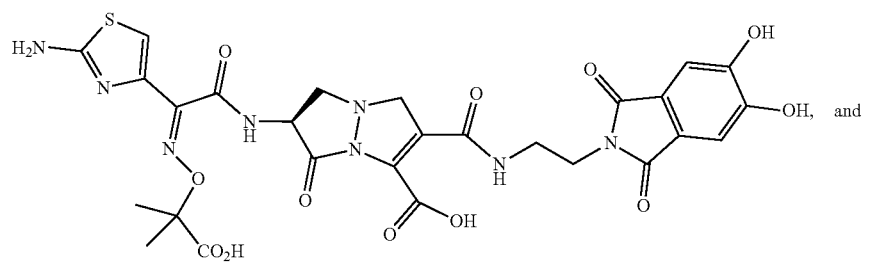
(26)
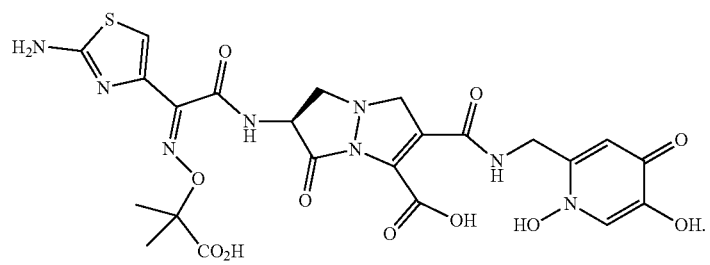
(16)

5. The compound of claim 1, which is:

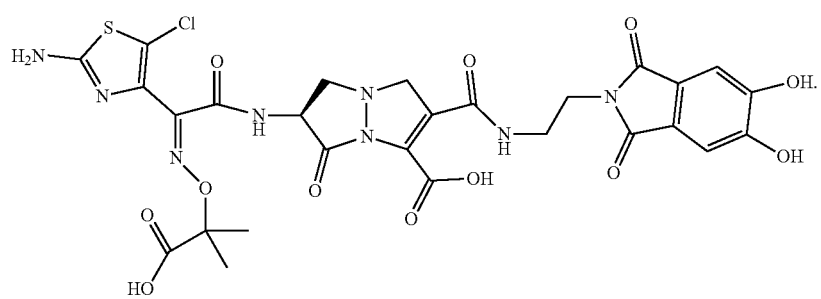

42

6. A pharmaceutical composition comprising the compound of claim 1, and at least one pharmaceutically acceptable carrier.

7. The pharmaceutical composition of claim 6, wherein the pharmaceutical composition is formulated for intravenous administration.

8. A method of treating, ameliorating or preventing a bacterial infection in a subject, the method comprising administering to the subject a therapeutically effective amount of the compound of claim 1.

9. The method of claim 8, wherein the bacterial infection is caused by a Gram negative bacterium.

10. The method of claim 8, wherein the bacterial infection is caused by an antibiotic resistant bacterium.

11. The method of claim 8, wherein the bacterial infection is caused by at least one selected from the group consisting of *Acinetobacter baumannii*, *Pseudomonas aeruginosa*, and *Klebsiella pneumoniae*.

12. The method of claim 8, wherein the bacterial infection is a nosocomial infection.

13. The method of claim 8, wherein the compound is administered to the subject as part of a pharmaceutical composition.

14. The method of claim 13, wherein the pharmaceutical composition is formulated for intravenous administration.

15. The method of claim 8, wherein the subject is further administered at least one additional agent to treat, ameliorate or prevent the bacterial infection.

16. The method of claim 8, wherein the subject is administered the compound intravenously.

17. The method of claim 8, wherein the subject is a mammal.

* * * * *